(12) United States Patent
Subjeck et al.

(10) Patent No.: US 7,976,846 B2
(45) Date of Patent: *Jul. 12, 2011

(54) STRESS PROTEIN COMPOSITIONS AND METHODS FOR PREVENTION AND TREATMENT OF CANCER AND INFECTIOUS DISEASE

(75) Inventors: John R. Subjeck, Williamsville, NY (US); Robert A. Henderson, Seattle, WA (US); Elizabeth A. Repasky, Williamsville, NY (US); Latif Kazim, Amherst, NY (US); Xiang-Yang Wang, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 1672 days.

This patent is subject to a terminal disclaimer.

(21) Appl. No.: 11/103,222

(22) Filed: Apr. 11, 2005

(65) Prior Publication Data
US 2005/0202035 A1 Sep. 15, 2005

Related U.S. Application Data

(62) Division of application No. 09/676,340, filed on Sep. 29, 2000, now Pat. No. 6,984,384.

(60) Provisional application No. 60/156,821, filed on Sep. 30, 1999, provisional application No. 60/163,138, filed on Nov. 2, 1999, provisional application No. 60/215,497, filed on Jun. 30, 2000.

(51) Int. Cl.
A61K 39/00 (2006.01)
A61K 39/02 (2006.01)
A61K 39/04 (2006.01)
A61K 39/12 (2006.01)

(52) U.S. Cl. .................................. 424/193.1; 424/277.1

(58) Field of Classification Search .......................... None
See application file for complete search history.

(56) References Cited

U.S. PATENT DOCUMENTS

| | | | |
|---|---|---|---|
| 5,066,579 A * | 11/1991 | Reyes ................................ | 435/5 |
| 5,550,214 A | 8/1996 | Eberlein et al. | |
| 5,726,023 A | 3/1998 | Cheever et al. | |
| 5,747,332 A | 5/1998 | Wallen et al. | |
| 5,830,464 A | 11/1998 | Srivastava | |
| 5,888,795 A * | 3/1999 | Hamilton ...................... | 435/200 |
| 5,891,432 A | 4/1999 | Hoo | |
| 5,961,979 A | 10/1999 | Srivastava | |
| 5,981,706 A | 11/1999 | Wallen et al. | |
| 6,015,567 A | 1/2000 | Hudziak et al. | |
| 6,017,540 A | 1/2000 | Srivastava et al. | |
| 6,066,716 A | 5/2000 | Wallen et al. | |
| 6,156,302 A | 12/2000 | Srivastava | |
| 6,162,436 A | 12/2000 | Srivastava | |
| 6,187,312 B1 | 2/2001 | Srivastava | |
| 6,268,213 B1 * | 7/2001 | Samulski et al. ........... | 435/320.1 |
| 6,322,790 B1 | 11/2001 | Srivastava | |
| 6,331,299 B1 | 12/2001 | Rothman et al. | |
| 6,403,095 B1 | 6/2002 | Srivastava et al. | |
| 7,157,089 B1 * | 1/2007 | Mizzen et al. ............. | 424/192.1 |

FOREIGN PATENT DOCUMENTS

| | | |
|---|---|---|
| WO | WO 94/29459 | 12/1994 |
| WO | WO 95/24923 | 9/1995 |
| WO | WO 96/10411 | 4/1996 |
| WO | WO 97/06821 | 2/1997 |
| WO | WO 97/10000 | 3/1997 |
| WO | WO 97/10001 | 3/1997 |
| WO | WO 97/10002 | 3/1997 |
| WO | WO 97/26910 | 7/1997 |
| WO | WO 98/23735 | 4/1998 |
| WO | WO 98/34641 | 8/1998 |
| WO | WO 98/35705 | 8/1998 |
| WO | WO 99/07860 | 2/1999 |
| WO | WO 00/44899 | 8/2000 |

OTHER PUBLICATIONS

Donnelly et al (Journal of Immunology, Jul. 15, 2005 175(2):633-639).*
Vanniasinkam et al (Journal of clinical virology, Aug. 2006, 36(4):292-297).*
Welch et al (Journal of Cell biology, 1985, vol. 101, pp. 1198-1211).*
Subjeck et al (Radiation Research, .1992, vol. 2, pp. 986-991).*
Spee et al (Biochemistry, 1999, vol. 38, pp. 10559-10566).*
Hughes et al (Cancer, 1970, vol. 26, pp. 269-278).*
Wang et al, (International Journal of Cancer, 2003, vol. 105, pp. 226-231).*
Kutomi et al (Journal of Immunology, 2009, vol. 183, pp. 5861-5869).*
Young et al (Ann Rev Immunology, 1990, vol. 8, pp. 4012-4200).*
Suto et al (Science, 1995, vol. 269, pp. 1585-1587).*

(Continued)

*Primary Examiner* — Karen A Canella
(74) *Attorney, Agent, or Firm* — Karen S. Canady; canady & lortz LLP

(57) ABSTRACT

Pharmaceutical compositions comprising a stress protein complex and related molecules encoding or cells presenting such a complex are provided. The stress protein complex comprises an hsp110 or grp170 polypeptide complexed with an immunogenic polypeptide. The immunogenic polypeptide of the stress protein complex can be associated with a cancer or an infectious disease. The pharmaceutical compositions of the invention can be administered to a subject, thereby providing methods for inhibiting *M. tuberculosis*-infection, for inhibiting tumor growth, for inhibiting the development of a cancer, and for the treatment or prevention of infectious disease. The invention further provides a method for producing T cells directed against a tumor cell or a *M. tuberculosis*-infected cell, wherein a T cell is contacted with an APC that is modified to present an hsp110 or grp170 polypeptide and an immunogenic polypeptide associated with a tumor or with the *M. tuberculosis*-infected cell. Included in the invention are T cells produced by this method and a pharmaceutical composition comprising such T cells. The T cells can be contacted with a *M. tuberculosis*-infected cell in a method for killing a *M. tuberculosis*-infected cell, or with a tumor cell in a method for killing a tumor cell.

18 Claims, 38 Drawing Sheets

OTHER PUBLICATIONS

A.L. Rakhmilevich et al., "Effective Particle-mediated Vaccination Against Mouse Melanoma by Coadministration of Plasmid DNA Encoding Gp100 and Granulocyte-Macrophage Colony-Stimulating Factor," Cancer Research, 2001, 7: 952-961.

C.I. Bargmann et al., "The neu oncogene encodes an epidermal growth factor receptor-related protein," 1986, Nature. 319(16):226-230.

C.I. Bargmann et al., "Multiple Independent Activations of the neu Oncogene by a Point Mutation Altering the Transmembrane Domain of p. 185." 1986. Cell, 45:649-657.

N.E. Blachere et al., "Heat Shock Protein-Based Cancer Vaccines and Related Thoughts on Immunogenicity of Human Tumors," Cancer Biology, 1995, vol. 6: 349-355.

N.E. Blachere et al., "Heat Shock Protein Vaccines Against Cancer," Jnl. of Immunology, 1993, 14(4): 352-356.

W.R. Boorstein et al., "Molecular Evolution of the HSP70 Multigene Family," 1994, J Mol Evol, 38:1-17.

C-II Chen et aL, "Enhancement of DNA Vaccine Potency by Linkage of Antigen Gene to an HSP70 Gene," Cancer Research, 2000, vol. 60: 1035-1042.

X. Chen et al., "The 170 kCa glucose regulated stress protein is a large HSP70-HSP110-like protein of the endoplasmic reticulum," XP-002060249,1996. FEBS Letters, 380:68-72.

R.N. Coler, "Molecular Cloning and Immunologic Reactivity of a Novel Low Molecular Mass Antigen of *Mycobacterium tuberculosis*[1]," 1998, Immun, 161(5):2356-2364.

D.C. Dillon et al., "Molecular Characterization and Human T-Cell Responses to a Member of a Novel *Mycobacterium tuberculosis*," XP-002143391. 1994. Infection and Immunity. pp. 2941-2950.

M.L. Disis et al., "Generation of Immunity to the HER-2/*neu* Oncogenic Protein in Patients with Breast and Ovarian Cancer Using a Peptide-based Vaccine," Clinical Cancer Research, 1999, vol. 5: 1289-1297.

T. Hatayama et aL, "Association of HSP105 with HSC70 in High Molecular Mass Complexes in Mouse FM3A Cells," 1998, Biochem and Biophys Res Comm, 248:395-401.

S. Janetzki et al., "Immunization of Cancer Patients with Autologous Cancer-Derived Heat Shock Protein gp96 Preparations: A Pilot Study," International Jnl. of Cancer, 2000, vol. 88: 232-238.

S. Jindal, "Heat shock proteins applications in health and disease,"1996, TB Tech, vol. 14, p. 5.

Z. Li, "Priming of T Cells by Heat Shock Protein-Peptide Complexes as the Basis of Tumor Vaccines," Seminars in Immunology, 1997, vol. 9: 315-322.

M.H. Manjili et al., "Development of a Recombinant HSP110-HER-2/*neu* Vaccine Using the Chaperoning Properties of HSP110." Cancer Research. 2002, vol. 62: 1737-1742.

M.H. Manjihi et al., "Immunotherapy of Cancer Using Heat Shock Proteins," Frontiers in Bioscience, 2002, vol. 7: d43-52.

A. Menoret et al., "Heat-Shock Protein-Based Anticancer Immunotherapy: An Idea Whose Time Has Come," Seminars in Oncology. 1998, 25(6): 654-660.

Y. Moroi et al., "Induction of Cellular Immunity by Immunization with Novel Hybrid Peptides. Complexed to Heat Shock Protein 70." PNAS, 2000, 97(7): 3485-3490.

H. Oh et al., "The Chaperoning Activity of hsp110," 1999,J of Biol Chem, 274(22):15712-15718.

D. Przepiorka et al., "Heat Shock Protein-Peptide Complexes as Immunotherapy for Human Cancer," Molecular Medicine Today, 1998, 4(11): 478-484.

T. Shyy et al., "Effect of Growth Stare and Heat Shock on Nucleolar Localization of the 110,000-Da Heat Shock Protein in Mouse Embryo Fibroblasts[1]," 1986. Cancer Research, 46:4738-4745.

P.K. Srivastava, "Purification of Heat Shock Prorein-Pcptide Complexes for Use in Vaccination Against Cancers and Intracellular Pathogens," Methods: A Companion to Methods in Enzymology, 1997, vol. 12: 165-171.

K. Suzue et al., "Heat shock fusion proteins as vehicles for antigen delivery into the major histocompatibility complex class I presentation pathway," 1997, Proc Nad Acad Sci USA, 94:13146-13151.

Y. Tamura et al., "Immunotherapy of Tumors with Autologous Tumor-Derived Heat Shock Protein Preparations," Science, 1997, vol. 278: 117-120.

H. Uduno et al., "Generation of Cytotoxic T Lymphocytes by MHC Class I Ligands Fused to Heat Shock Cognate Protein 70," International Immunology, 2001,13(10): 1233-1242.

D.K. Vanaja et al., "Tumor Prevention and Antitumor Immunity with Heat Shock Protein 70 Induced by 15-Deoxy-$\Delta^{12,14}$-prostaglandin Ja in Transgenic Adenocarcinoma of Mouse Prostate Cells," Cancer Research, 2000, vol. 60: 4714-4718.

X-Y. Wang et al., "Characterization of Heat Shock Protein 110 and Glucose-Regulated Protein 170 as Cancer Vaccines and the Effect of Fever-Range Hyperthermia on Vaccine Activity," Jnl. of Immunology, 2001, vol. 165, pp. 490-497.

S.P.K. Yedavelli et al., "Preventive and Therapeutic Effect of Tumor Derived Heat Shock Protein, gp96, in an Experimental Prostate Cancer Model," International Jnl. of Molecular Medicine, 1999, 4(3): 243-248.

Doug et al. (Pharmaceutical Biotechnology, 1995, vol. 6, pp. 625-643).

Heath (Pharmaceutical Biotechnology, 1995. vol. 6, pp. 645-658).

The abstract of Wang et al (FEBS Letters, Jan. 1999, vol. 464, pp. 98-102).

Ikeda et al., "Cloning and Expression of cDNA Encoding . . . ORP150", Biochemical and Biophysical Research Communications, 1997, 230: pp. 94-99.

Lin et al., "The 170-kDa Glucose-regulated Stress Protein . . . Immunoglobulin", Molecuclar Biology of the Cell, 1993, 4: pp. 1009-1119.

Santos et al., "Characterization of the HSP110/SSE gene . . . stresses", American Journal of Physiology, 1998, 274: pp. F1054-F1061.

\* cited by examiner

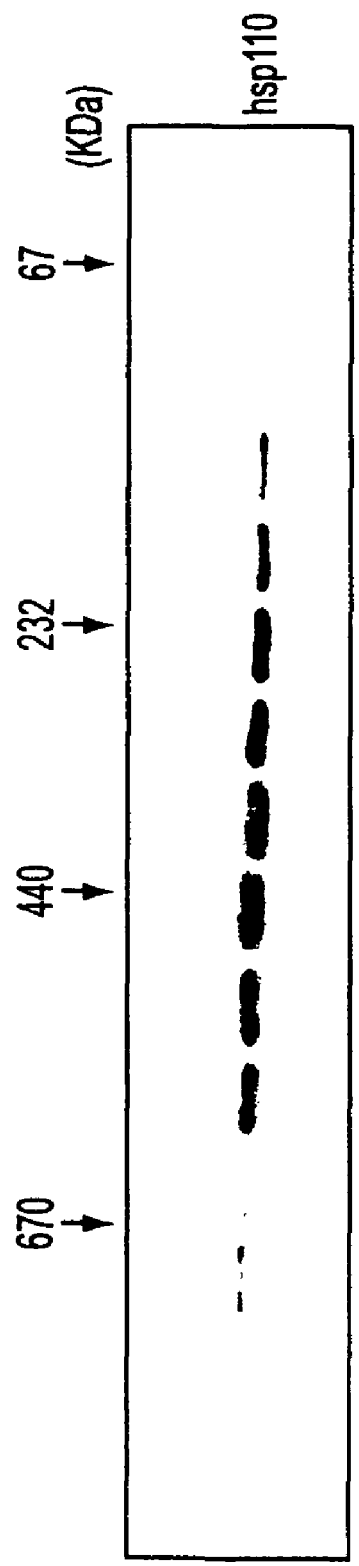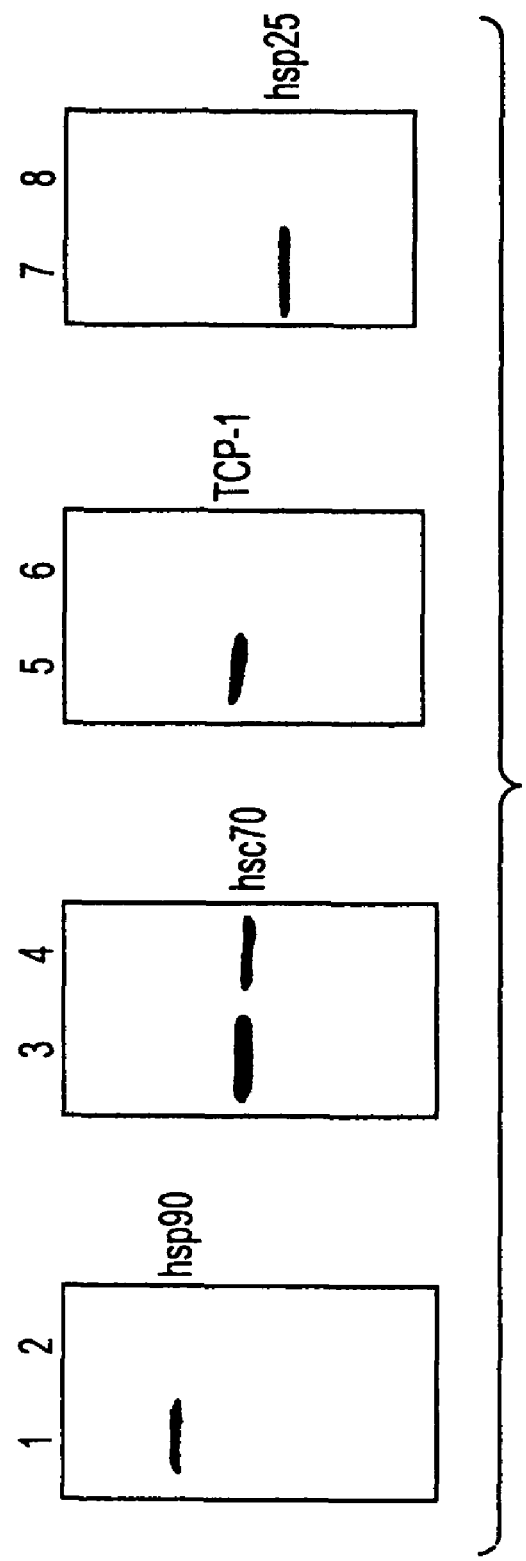
FIG. 9A
FIG. 9B

STRESS PROTEIN COMPOSITIONS AND METHODS FOR PREVENTION AND TREATMENT OF CANCER AND INFECTIOUS DISEASE

This application is a divisional of U.S. application Ser. No. 09/676,340, filed Sep. 29, 2000, now U.S. Pat. No. 6,984,384, which claims benefit of U.S. provisional patent application Ser. Nos. 60/156,821, filed Sep. 30, 1999, 60/163,138, filed Nov. 2, 1999, and 60/215,497, filed Jun. 30, 2000, the entire contents of each of which are hereby incorporated by reference herein.

The invention disclosed herein was made in the course of work done under the support of Grant No. GM 45994, awarded by the National Institutes of Health. The government may have certain rights in this invention.

Throughout this application various publications are referenced. The disclosures of these publications in their entireties are hereby incorporated by reference into this application in order to describe more fully the state of the art to which this invention pertains.

TECHNICAL FIELD

The present invention relates generally to prevention and therapy of cancer and infectious disease. The invention is more specifically related to polypeptides comprising at least a portion of a stress protein, such as heat shock protein 110 (hsp110) or glucose-regulated protein 170 (grp170), complexed with an immunogenic polypeptide, and to polynucleotides encoding such stress proteins and immunogenic polypeptides, as well as antigen presenting cells that present the stress proteins and the immunogenic polypeptides. Such polypeptides, polynucleotides and antigen presenting cells may be used in vaccines and pharmaceutical compositions for the prevention and treatment of cancers and infectious diseases. The invention further relates to increasing the efficacy of stress protein complexes, such as by heating.

BACKGROUND OF THE INVENTION

Cancer and infectious disease are significant health problems throughout the world. Although advances have been made in detection and therapy of these diseases, no vaccine or other universally successful method for prevention or treatment is currently available. Current therapies, which are generally based on a combination of chemotherapy or surgery and radiation, continue to prove inadequate in many patients.

For example, primary breast carcinomas can often be treated effectively by surgical excision. If further disease recurs, however, additional treatment options are limited, and there are no effective means of treating systemic disease. While immune responses to autologous tumors have been observed, they have been ineffective in controlling the disease. One effort to stimulate a further anti-tumor response is directed at the identification of tumor antigens useful for vaccines. A related approach takes advantage of the promiscuous peptide binding properties of heat shock proteins, such as hsp70. These molecular chaperones bind peptides and are involved in numerous protein folding, transport and assembly processes, and could be involved in the antigen presentation pathway of MHC complexes.

The heat shock proteins of mammalian cells can be classified into several families of sequence related proteins. The principal mammalian hsps, based on protein expression levels, are cytoplasmic/nuclear proteins with masses of (approximately) 25 kDa (hsp25), 70 kDa (hsp70), 90 kDa (hsp90), and 110 kDa (hsp110). However, in addition to hsps, a second set of stress proteins is localized in the endoplasmic reticulum (ER). The induction of these stress proteins is not readily responsive to hyperthermic stress, as are the hsps, but are regulated by stresses that disrupt the function of the ER (e.g. glucose starvation and inhibitors of glycosylation, anoxia and reducing conditions, or certain agents that disrupt calcium homeostasis). These stress proteins are referred to as glucose regulated proteins (grps). The principal grps, on the basis of expression, have approximate sizes of 78 kDa (grp78), 94 kDa (grp94), and 170 kDa (grp170). Grp78 is homologous to cytoplasmic hsp70, while grp94 is homologous to hsp90.

While individual stress proteins have been studied for several years (in some cases intensively studied, e.g. hsp70), the largest of the above hsp and grp groups, hsp110 and grp170, have received little attention. Both have been found by sequence analysis to represent large and highly diverged relatives of the hsp70 family. It is recognized that the hsp70 family, the hsp110 family, and the grp170 family comprise three distinguishable stress protein groups of eukaryotic cells that share a common evolutionary ancestor. The existence of hsp110 in parallel with hsp70 in the cytoplasm and of grp170 in parallel with grp78 in the ER of (apparently) all eukaryotic cells argues for important differential functions for these distantly related protein families. Not all stress proteins function as vaccines, however, and it can be expected that different ones may exhibit different activities.

In spite of considerable research into therapies for infectious disease and cancer, these diseases remain difficult to diagnose and treat effectively. Accordingly, there is a need in the art for improved methods for treating cancer and infectious disease. The present invention fulfills these needs and further provides other related advantages.

SUMMARY OF THE INVENTION

The invention provides a pharmaceutical composition comprising a stress protein complex. The stress protein complex comprises an hsp110 or grp170 polypeptide and an immunogenic polypeptide. In some embodiments, the hsp110 or grp170 polypeptide is complexed with the immunogenic polypeptide, for example, by non-covalent interaction or by covalent interaction, including a fusion protein. In some embodiments, the complex is derived from a tumor. In other embodiments, the complex is derived from cells infected with an infectious agent. The immunogenic polypeptide of the stress protein complex can be associated with a cancer or an infectious disease. The stress protein complex of the invention can further include additional stress polypeptides, including members of the hsp70, hsp90, grp78 and grp94 stress protein families. In one embodiment, the stress protein complex comprises hsp110 complexed with hsp70 and/or hsp25.

The invention additionally provides a pharmaceutical composition comprising a first polynucleotide encoding an hsp110 or a grp170 polypeptide and a second polynucleotide encoding an immunogenic polypeptide. In some embodiments involving first and second polynucleotides, the first polynucleotide is linked to the second polynucleotide. The pharmaceutical compositions of the invention can further comprise a physiologically acceptable carrier and/or an adjuvant. The efficacy of a pharmaceutical composition can further comprise GM-CSF-secreting cells. Alternatively, GM-CSF-secreting cells can be co-administered with a pharmaceutical composition of the invention, by administration before, during or after administration of the pharmaceutical composition. The use of GM-CSF-secreting cells enhances the efficacy of the pharmaceutical composition.

In some embodiments, the complex is purified from a tumor or from cells infected with an infectious agent. In such embodiments, the stress polypeptide, as purified, is complexed with one or more immunogenic polypeptides. The binding of the stress polypeptide to the immunogenic polypeptide can be altered and/or enhanced by stress, such as by exposure to heat, anoxic and/or ischemic conditions, or proteotoxic stress. In particular, a stress protein complex of the invention can comprise a stress polypeptide complexed with an immunogenic polypeptide, wherein the complex has been heated. Such heating, particularly wherein the stress polypeptide comprises a heat-inducible stress protein, can increase the efficacy of the stress protein complex as a vaccine. Examples of heat-inducible stress proteins include, but are not limited to, hsp70 and hsp110.

In some embodiments, the immunogenic polypeptide is known. Where the immunogenic polypeptide is a known molecule, the immunogenic polypeptide can be provided in admixture with the stress polypeptide, or as a complex with the stress polypeptide. The hsp110 or grp170 polypeptide can be complexed with the immunogenic polypeptide by noncovalent binding. Alternatively, the complex can comprise a fusion protein, wherein the stress polypeptide is linked to the immunogenic polypeptide. Examples of immunogenic polypeptides include, but are not limited to, antigens associated with cancer or infectious disease, such as the breast cancer antigen her2/neu or the *Mycobacterium tuberculosis* antigens Mtb8.4 and Mtb39. Where the immunogenic polypeptide is unknown, it can be obtained incidentally to the purification of the stress polypeptide from tissue of a subject having cancer or an infectious disease.

Also provided is a pharmaceutical composition comprising an antigen-presenting cell (APC) modified to present an hsp110 or grp170 polypeptide and an immunogenic polypeptide. Alternatively, the APC can be modified to present an immunogenic polypeptide obtained by purification of hsp110 or grp170 from disease cells, including cancer cells and cells infected with an infectious agent. Preferably, the APC is a dendritic cell or a macrophage. The APC can be modified by various means including, but not limited to, peptide loading and transfection with a polynucleotide encoding an immunogenic polypeptide.

The pharmaceutical compositions of the invention can be administered to a subject, thereby providing methods for inhibiting *M. tuberculosis*-infection, for inhibiting tumor growth, for inhibiting the development of a cancer, and for the treatment or prevention of cancer or infectious disease.

The invention further provides a method for producing T cells directed against a tumor cell. The method comprises contacting a T cell with an antigen presenting cell (APC), wherein the APC is modified to present an hsp110 or grp170 polypeptide and an immunogenic polypeptide associated with the tumor cell. Such T cells can be used in a method for killing a tumor cell, wherein the tumor cell is contacted with the T cell. Likewise, the invention provides a method for producing T cells directed against a *M. tuberculosis*-infected cell, wherein a T cell is contacted with an APC that is modified to present an hsp110 or grp170 polypeptide and an immunogenic polypeptide associated with the *M. tuberculosis*-infected cell. Included in the invention are T cells produced by this method and a pharmaceutical composition comprising such T cells. The T cells can be contacted with a *M. tuberculosis*-infected cell in a method for killing a *M. tuberculosis*-infected cell. The T cells can be CD4+ or CD8+.

The invention also provides a method for removing tumor cells from a biological sample. The method comprises contacting a biological sample with a T cell of the invention. In a preferred embodiment, the biological sample is blood or a fraction thereof. Also provided is a method for inhibiting tumor growth in a subject. The method comprises incubating CD4+ and/or CD8+ T cells isolated from the subject with an antigen presenting cell (APC), wherein the APC is modified to present an hsp110 or grp170 polypeptide and an immunogenic polypeptide associated with the tumor cell such that T cells proliferate. The method further comprises administering to the subject an effective amount of the proliferated T cells, and thereby inhibiting tumor growth in the subject. In an alternative embodiment, the method for inhibiting tumor growth in a subject comprises incubating CD4+ and/or CD8+ T cells isolated from the subject with an antigen presenting cell (APC), wherein the APC is modified to present an hsp110 or grp170 polypeptide and an immunogenic polypeptide associated with the tumor cell such that T cells proliferate, cloning at least one proliferated cell, and administering to the patient an effective amount of the cloned T cells, thereby inhibiting tumor growth in the subject.

BRIEF DESCRIPTION OF THE FIGURES

FIG. 9A shows chromatography profiles of native hsp110 separated by size exclusion column for FPLC for characterization of hsp110 complex. Hsp110 was partially purified by successive chromatography on Con-A sepharose and mono Q column. Pooled fraction was loaded on the superose 6 column, proteins in each fraction were detected by immunoblotting with antibodies for hsp110, hsc70 and hsp25 (1:1000).

FIG. 9B is an immunoblot that shows composition analysis of native hsp110 complex. Purified hsp110 fraction was detected by antibodies for hsp90 (lane 1, 2), hsc70 (lane 3, 4), TCP-1 (lane 5, 6) and hsp25 (lane 7, 8). Total cell extracts was also used as a positive control (lane 1, 3, 5, 7).

FIG. 10A shows results observed when cell lysates (lane 2) were incubated with antibodies for hsp110 (1:100).

FIG. 10B shows results observed when cell lysates (lane 2) were incubated with antibodies for hsp70 (1:200).

FIG. 10C shows results observed when cell lysates (lane 2) were incubated with antibodies for hsp25 (1:100).

DETAILED DESCRIPTION OF THE INVENTION

Figure 1A:
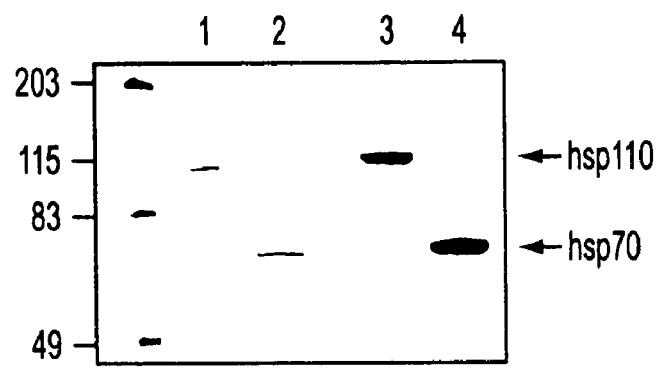
FIG. 1A shows silver staining and analysis of purified hsp proteins. Gel staining of hsp110 and hsp70 from tumor are shown in lanes 1 and 2, respectively. Lanes 3 and 4 show results of an immunoblot analysis with hsp110 antibody and hsp70 antibody, respectively.

The present invention is based on the discovery that the stress proteins hsp110 and grp170, when complexed with tumor antigens, are remarkably effective as anti-tumor vaccines. The efficacy of these stress protein complexes has been demonstrated in both prophylactic and therapeutic contexts. The discovery of the ability of these stress proteins to facilitate an effective immune response provides a basis for their use in presenting a variety of antigens for use in prophylaxis and therapy of cancer and infectious disease. Because both hsp110 and grp170 have an enlarged peptide binding cleft and can stabilize unfolded peptide chains with greater efficiency relative to hsp70, these molecules can elicit different immunological reactions than previously obtained.

Overview of Stress Proteins hsp110 and grp170

While the expression of most cellular proteins is significantly reduced in mammalian cells exposed to sudden elevations of temperature, heat shock proteins exhibit increased expression under these conditions. Heat shock proteins, which are produced in response to a variety of stressors, have the ability to bind other proteins in the non-native states (e.g., denatured by heating or guanidium chloride treatment), and in particular the ability to bind nascent peptides emerging from ribosomes or extruded from the endoplasmic reticulum (Hendrick and Hartl, Ann. Rev. Biochem. 62:349-384, 1993; Hartl, Nature 381:571-580, 1996). Heat shock proteins have also been shown to serve a chaperoning function, referring to their important role in the proper folding and assembly of proteins in the cytosol, endoplasmic reticulum and mitochondria (Frydman et al., Nature 370:111-117, 1994).

Mammalian heat shock protein families include hsp28, hsp70, hsp90 and hsp110. These primary heat shock proteins are found in the cytoplasm and, to a lesser extent, in the nucleus. An additional set of stress proteins, known as glucose regulated proteins (grps), reside in the endoplasmic reticulum. The major families of glucose regulated proteins includes grp78, grp74 and grp170. This category of stress proteins lack heat shock elements in their promoters and are not inducible by heat, but by other stress conditions, such as anoxia.

Hsp110 is an abundant and strongly inducible mammalian heat shock protein. Human hsp110 is also known as KIAA0201, NY-CO-25, HSP105 alpha and HSP105 beta. Mouse hsp110 is also known as HSP105 alpha, HSP105 beta, 42° C.-specific heat shock protein, and hsp-E7I. Hsp110 has an ATP binding beta sheet and alpha helical regions that are capable of binding peptides having greater size and different binding affinities as compared to hsp70. Hsp110 has also been shown to bind shorter peptides (12mers) and a preferred consensus motif for binding to hsp110 has been determined (i.e., basic, polar, aromatic/basic, proline, basic, acidic, aromatic, aromatic, basic, aromatic, proline, basic, X (no preference), basic/aromatic). This sequence differs from preferred sequence motifs previously identified to bind to members of the hsp70 family.

Hsp110 is more efficient in stabilizing heat denatured proteins compared to hsp70, being four-fold more efficient on an equimolar basis. The peptide binding characteristics of hsp70 and hsp110 make them effective in inhibiting aggregation of denatured protein by binding to denatured peptide chain. Using two different denaturing conditions, heating and guanidium chloride exposure, hsp110 exhibits nearly total efficacy in inhibiting aggregation of these luciferase and citrate synthase when present in a 1:1 molar ratio. Hsp70 family members perform a similar function, but with significantly lower efficiency. Grp170 is a strong structural homolog to hsp110 that resides in the endoplasmic reticulum (Lin et al., Mol. Biol. Cell 4:1109-19, 1993; Chen et al., FEBS Lett. 380:68-72, 1996). Grp170 exhibits the same secondary structural features of hsp110, including an enlarged peptide binding domain. Grp170 is predicted to contain a beta sheet domain near its center, a more C-terminal alpha-helical domain, and a loop domain connecting both that is much longer than the loop domain present in hsp110 (200 amino acids versus 100 amino acids in length) and absent in DnaK. In addition, grp170 is likely the critical ATPase required for protein import into the mammalian endoplasmic reticulum (Dierks et al., EMBO J. 15;6931-42, 1996). Grp170 is also known as ORP150 (oxygen-regulated protein identified in both human and rat) and as CBP-140 (calcium binding protein identified in mouse). Grp170 has been shown to stabilize denatured protein more efficiently than hsp70.

The discovery disclosed herein that both grp170 and hsp110 function as vaccines provides the capability for novel and more effective vaccines for use in the treatment and prevention of cancer and infectious disease than previously available strategies.

Definitions

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "tumor protein" is a protein that is expressed by tumor cells. Proteins that are tumor proteins also react detectably within an immunoassay (such as an ELISA) with antisera from a patient with cancer.

As used herein, a "heat-inducible stress polypeptide" means a stress polypeptide or protein whose expression is induced by elevated temperature. One example of a heat-inducible stress polypeptide comprises a stress protein that contains one or more heat shock elements in its promoter.

An "immunogenic polypeptide," as used herein, is a portion of a protein that is recognized (i.e., specifically bound) by a B-cell and/or T-cell surface antigen receptor. Such immunogenic polypeptides generally comprise at least 5 amino acid residues, more preferably at least 10, and still more preferably at least 20 amino acid residues of a protein associated with cancer or infectious disease. Certain preferred immunogenic polypeptides include peptides in which an N-terminal leader sequence and/or transmembrane domain have been deleted. Other preferred immunogenic polypeptides may contain a small N- and/or C-terminal deletion (e.g., 1-30 amino acids, preferably 5-15 amino acids), relative to the mature protein.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%/) saline.

Compositions comprising such carriers are formulated by well known conventional methods (see, for example, Remington's Pharmaceutical Sciences, Chapter 43, 14th Ed., Mack Publishing Co, Easton Pa. 18042, USA).

As used herein, "adjuvant" includes those adjuvants commonly used in the art to facilitate an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (Smith-Kline Beecham); QS-21 (Aquilla Biopharmaceuticals); MPL or 3d-MPL (Corixa Corporation, Hamilton, Mont.); LEIF; salts of calcium, iron or zinc; an insoluble suspension of acylated tyrosine; acylated sugars; -cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

Polynucleotides of the Invention

The invention provides polynucleotides, including a first polynucleotide that encodes one or more stress proteins, such as hsp110 or grp170, or a portion or other variant thereof, and a second polynucleotide that encodes one or more immunogenic polypeptides, or a portion or other variant thereof. In some embodiments, the first and second polynucleotides are linked to form a single polynucleotide that encodes a stress protein complex. The single polynucleotide can express the first and second proteins in a variety of ways, for example, as a single fusion protein or as two separate proteins capable of forming a complex.

Preferred polynucleotides comprise at least 15 consecutive nucleotides, preferably at least 30 consecutive nucleotides and more preferably at least 45 consecutive nucleotides, that encode a portion of a stress protein or immunogenic polypeptide. More preferably, the first polynucleotide encodes a peptide binding portion of a stress protein and the second polynucleotide encodes an immunogenic portion of an immunogenic polypeptide. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a stress protein, immunogenic polypeptide or a portion thereof) or may comprise a variant of such a sequence. Polynucleotide variants contain one or more substitutions, additions, deletions and/or insertions such that the immunogenicity of the encoded polypeptide is not diminished, relative to a native stress protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native stress protein or a portion thereof Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native stress protein (or a complementary sequence). Suitable moderately stringent conditions include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art. DNA encoding a stress protein may be obtained from a cDNA library prepared from tissue expressing a stress protein mRNA. Accordingly, human hsp110 or grp170 DNA can be conveniently obtained from a cDNA library prepared from human tissue. The stress protein-encoding gene may also be obtained from a genomic library or by oligonucleotide synthesis. Libraries can be screened with probes (such as antibodies to the stress protein or oligonucleotides of at least about 20-80 bases) designed to identify the gene of interest or the protein encoded by it. Illustrative libraries include human liver cDNA library (human liver 5' stretch plus cDNA, Clontech Laboratories, Inc.) and mouse kidney cDNA library (mouse kidney 5'-stretch cDNA, Clontech laboratories, Inc.). Screening the cDNA or genomic library with the selected probe may be conducted using standard procedures, such as those described in Sambrook et al., *Molecular Cloning: A Laboratory Manual* (New York: Cold Spring Harbor Laboratory Press, 1989). An alternative means to isolate the gene encoding hsp110 or grp170 is to use PCR methodology (Sambrook et al., supra; Dieffenbach et al., *PCR Primer: A Laboratory Manual* (Cold Spring Harbor Laboratory Press, 1995)).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs, which employ various algorithms to measure homology.

Nucleic acid molecules having protein coding sequence may be obtained by screening selected cDNA or genomic libraries, and, if necessary, using conventional primer extension procedures as described in Sambrook et al., supra, to detect precursors and processing intermediates of mRNA that may not have been reverse-transcribed into cDNA.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a stress protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a stress polypeptide, and administering the transfected cells to the patient).

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Stress Polypeptides and Immunogenic Polypeptides

Within the context of the present invention, stress polypeptides and stress proteins comprise at least a peptide binding portion of an hsp110 and/or grp170 protein and/or a variant thereof. Polypeptides as described herein may be of any length. Additional sequences derived from the native protein and/or heterologous sequences may be present, and such sequences may, but need not, possess further peptide binding, immunogenic or antigenic properties. In some embodiments, the stress polypeptide further includes all or a portion of a member of the hsp70, hsp90, grp78 and grp94 stress protein families.

Functional domains and variants of hsp110 that are capable of mediating the chaperoning and peptide binding activities of hsp110 are identified in Oh, H J et al., J. Biol. Chem. 274(22):15712-18, 1999. Functional domains of grp170 parallel those of hsp110. Candidate fragments and variants of the stress polypeptides disclosed herein can be identified as having chaperoning activity by assessing their ability to solubilize heat-denatured luciferase and to refold luciferase in the presence of rabbit reticulocyte lysate (Oh et al., supra).

In some embodiments, the immunogenic polypeptide is associated with a cancer or precancerous condition. One example of an immunogenic polypeptide associated with a cancer is a her-2/neu peptide (Bargmann et al., 1986, Nature 319(6050):226-30; Bargmann et al., 1986, Cell 45(5):649-57). Examples of her-2/neu peptides include, but are not limited to, the intracellular domain of her-2/neu (amino acid residues 676-1255; see Bargmann et al. references above), p369 (also known as E75; KIFGSLAFL; SEQ ID NO: 6) of the extracellular domain of her-2/neu, and p546, a transmembrane region of her-2/neu (VLQGLPREYV; SEQ ID NO: 5). In other embodiments, the immunogenic polypeptide is associated with an infectious disease. One example of an immunogenic polypeptide associated with an infectious disease is an antigen derived from M. tuberculosis, such as M. tuberculosis antigens Mtb 8.4 (Coler et al., 1998, J. Immunol. 161 (5):2356-64) or Mtb 39 (also known as Mtb39A; Dillon et al., 1999, Infect. Immun. 67(6):2941-50).

The immunogenic polypeptide may be known or unknown. Unknown immunogenic polypeptides can be obtained incidentally to the purification of hsp110 or grp170 from tissue of a subject having cancer or a precancerous condition or having an infectious disease. In other embodiments, the immunogenic polypeptide comprises a known antigen.

Immunogenic polypeptides may generally be identified using well known techniques, such as those summarized in Paul, Fundamental Immunology, 4th ed., 663-665 (Lippincott-Raven Publishers, 1999) and references cited therein. Such techniques include screening polypeptides for the ability to react with antigen-specific antibodies, antisera and/or T-cell lines or clones. As used herein, antisera and antibodies are antigen-specific if they specifically bind to an antigen (i.e., they react with the protein in an ELISA or other immunoassay, and do not react detectably with unrelated proteins). Such antisera and antibodies may be prepared using well known techniques. An immunogenic polypeptide can be a portion of a native protein that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using -methods well known to those of ordinary skill in the art, such as those described in Harlow and Lane, Antibodies: A Laboratory Manual, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Stress protein complexes of the invention can be obtained through a variety of methods. In one example, a recombinant hsp110 or grp170 is mixed with cellular material (e.g., lysate), to permit binding of the stress polypeptide with one or more immunogenic polypeptides within the cellular material. Such binding can be enhanced or altered by stress conditions, such as heating of the mixture. In another example, target cells are transfected with hsp110 or grp170 that has been tagged (e.g., HIS tag) for later purification. This example provides a method of producing recombinant stress polypeptide in the presence of immunogenic material. In yet another example, heat or other stress conditions are used to induce hsp110 or grp170 in target cells prior to purification of the stress polypeptide. This stressing can be performed in situ, in vitro or in cell cultures).

In some embodiments, the invention provides a stress protein complex having enhanced immunogenicity that comprises a stress polypeptide and an immunogenic polypeptide, wherein the complex has been heated. Such heating, particularly wherein the stress polypeptide comprises a heat-inducible stress protein, can increase the efficacy of the stress protein complex as a vaccine. Examples of heat-inducible stress proteins include, but are not limited to, hsp70 and hsp110. In one embodiment, heating comprises exposing tissue including the stress protein complex to a temperature of at least approximately 38° C., and gradually increasing the temperature, e.g. by 1° C. at a time, until the desired level of heating is obtained. Preferably, the temperature of the tissue is brought to approximately 39.5° C., ±0.5° C. At the time of heating, the tissue can be in vivo, in vitro or positioned within a host environment.

A stress protein complex of the invention can comprise a variant of a native stress protein. A polypeptide "variant," as used herein, is a polypeptide that differs from a native stress protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the N- and/or C-terminal of the mature protein.

Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein that co-translationally or post-translationally directs transfer of the protein. The polypeptide may also be conjugated to a linker or other sequence for ease of synthesis, purification or identification of the polypeptide (e.g., poly-FEs), or to enhance binding of the polypeptide to a solid support. For example, a polypeptide may be conjugated to an immnunoglobulin Fc region.

Polypeptides may be prepared using any of a variety of well known techniques, including the purification techniques described in Example 1 below. In one embodiment, the stress polypeptide(s) and immunogenic polypeptide(s) are co-purified from tumor cells or cells infected with a pathogen as a result of the purification technique. In some embodiments, the tumor cells or infected cells are stressed prior to purification to enhance binding of the immunogenic polypeptide to the stress polypeptide. For example, the cells can be stressed in vitro by several hours of low-level heating (39.5-40° C.) or about 1 to about 2 hours of high-level heating (approximately 43° C.). In addition, the cells can be stressed in vitro by exposure to anoxic and/or ischemic or proteotoxic conditions. Tumors removed from a subject can be minced and heated in vitro prior to purification.

In some embodiments, the polypeptides are purified from the same subject to whom the composition will be administered. In these embodiments, it may be desirable to increase the number of tumor or infected cells. Such a scale up of cells could be performed in vitro or in vivo, using, for example, a SCID mouse system. Where the cells are scaled up in the presence of non-human cells, such as by growing a human subject's tumor in a SCID mouse host, care should be taken to purify the human cells from any non-human (e.g., mouse) cells that may have infiltrated the tumor. In these embodiments in which the composition will be administered to the same subject from whom the polypeptides are purified, it may also be desirable purify both hsp110 and grp170 as well as additional stress polypeptides to optimize the efficacy of a limited quantity of starting material.

Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, yeast, insect cells or a mammalian cell line such as COS or CHO. Supernatants from suitable host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to farther purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

Polypeptides can be synthesized on a Perkin Elmer/Applied Biosystems Division 430A peptide synthesizer using FMOC chemistry with HPTU (O-BenzotriazoleN,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid: ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water may be used to elute the peptides. Following lyophilization of the pure fractions, the peptides may be characterized using electrospray or other types of mass spectrometry and by amino acid analysis.

Fusion Proteins

In some embodiments, the polypeptide is a fusion protein that comprises multiple polypeptides as described herein, or that comprises at least one polypeptide as described herein and an unrelated sequence. In some embodiments, the fusion protein comprises a stress polypeptide of hsp110 and/or grp170 and an immunogenic polypeptide. The immunogenic polypeptide can comprise all or a portion of a tumor protein or a protein associated with an infectious disease.

Additional fusion partners can be added. A fusion partner may, for example, serve as an immunological fusion partner by assisting in the provision of T helper epitopes, preferably T helper epitopes recognized by humans. As another example, a fusion partner may serve as an expression enhancer, assisting in expressing the protein at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals ate present 3' to the DNA sequence encoding the second polypeptide.

Fusion proteins ate also provided that comprise a polypeptide of the present invention together with an unrelated immunogenic protein. Preferably the immunogenic protein is capable of eliciting a memory response. Examples of such proteins include tetanus, tuberculosis and hepatitis proteins (see, for example, Stoute et al., New Engl. J. Med. 336:86-91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS I (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAR This property has been exploited for the development of *E. coli* CLYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system.

Preferably, such polypeptides are at least about 90% pure, more preferably at least about 95% pure and most preferably at least about 99% pure. A polynucleotide is considered to be isolated if, for example, it is cloned into a vector that is not a part of the natural environment.

T Cells

Immunotherapeutic compositions may also, or alternatively, comprise T cells specific for a stress protein complexed with an immunogenic polypeptide ("stress protein complex"). Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ magnetic cell selection system, available from Nexell Therapeutics, Irvine, Calif. (see also U.S. Pat. No. 5,536,475); or MACS cell separation technology from Miltenyi Biotec, including Pan T Cell Isolation Kit, CD4+ T Cell Isolation Kit, and CD8+ T Cell Isolation Kit (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a stress protein complex, polynucleotide encoding a stress protein complex and/or an antigen presenting cell (APC) that expresses such a stress protein complex. The stimulation is performed under conditions and for a time sufficient to permit the generation of T cells that are specific for the polypeptide. Preferably, a stress polypeptide or polynucleotide is present within a delivery vehicle, such as a microsphere, to facilitate the generation of specific T cells.

T cells are considered to be specific for a stress polypeptide if the T cells kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065-1070, 1994.

Detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a stress protein complex (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a stress polypeptide, polynucleotide or polypeptide-expressing APC may be CD4+ and/or CD8+. T cells can be expanded using standard techniques.

Within preferred embodiments, the T cells are derived from either a patient or a related, or unrelated, donor and are administered to the patient following stimulation and expansion. For therapeutic purposes, CD4+ or CD8+ T cells that proliferate in response to a stress polypeptide, polynucleotide or APC can be expanded in number either in vitro or in vivo. Proliferation of such T cells in vitro may be accomplished in a variety of ways. For example, the T cells can be re-exposed to a stress polypeptide complexed with an immunogenic polypeptide, with or without the addition of T cell growth factors, such as interleukin-2, and/or stimulator cells that synthesize a stress protein complex. Alternatively, one or more T cells that proliferate in the presence of a stress protein complex can be expanded in number by cloning. Methods for cloning cells are well known in the art, and include limiting dilution.

Pharmaceutical Compositions and Vaccines

The invention provides stress protein complex polypeptides, polynucleotides, T cells and/or antigen presenting cells that are incorporated into pharmaceutical compositions, including immunogenic compositions (i.e., vaccines). Pharmaceutical compositions comprise one or more such compounds and, optionally, a physiologically acceptable carrier. Vaccines may comprise one or more such compounds and an adjuvant that serves as a non-specific immune response enhancer. The adjuvant may be any substance that enhances an immune response to an exogenous antigen. Examples of adjuvants include conventional adjuvants, biodegradable microspheres (e.g., polylactic galactide), immunostimulatory oligonucleotides and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds that may be biologically active or inactive. For example, one or more immunogenic portions of other tumor antigens may be present, either incorporated into a fusion polypeptide or as a separate compound, within the composition or vaccine.

A pharmaceutical composition or vaccine can contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Nail. Acad. Sci. USA 86:317-321, 1989; Flexner et al., Ann. N. Y. Acad Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Nail. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology. Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-α, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145-173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Hamilton, Mont.) (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 313MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Another adjuvant that may be used is AS-2 (Smith-Kline Beecham). Any vaccine provided herein may be prepared using well known methods that result in a combination of antigen, immune response enhancer and a suitable carrier or excipient.

A stress polypeptide of the invention can also be used as an adjuvant, eliciting a predominantly Th1-type response as well. The stress polypeptide can be used in conjunction with other vaccine components, including an immunogenic polypeptide and, optionally, additional adjuvants.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Antigen Presenting Cells

Any of a variety of delivery vehicles may be employed within pharmaceutical compositions and vaccines to facilitate production of an antigen-specific immune response that targets tumor cells or infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor or anti-infective effects per se and/or to be immunologically compatible with the receiver (i.e., matched BLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic antitumor immunity (see Timmerman and Levy, Ann. Rev. Med. 50:507-529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II NMC, adhesion molecules (e.g., CD54 and CD11) and costimulatory molecules (e.g., CD40, CD80 and CD86).

APCs may generally be transfected with a polynucleotide encoding a stress protein (or portion or other variant thereof) such that the stress polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and Cell Biology 75:456-460, 1997. Antigen loading of dendritic cells may be achieved by incubating dendritic cells or progenitor cells with the stress polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Therapeutic and Prophylactic Methods

The stress protein complexes and pharmaceutical compositions of the invention can be administered to a subject, thereby providing methods for inhibiting *M. tuberculosis*-infection, for inhibiting tumor growth, for inhibiting the development of a cancer, and for the treatment or prevention of cancer or infectious disease.

Treatment includes prophylaxis and therapy. Prophylaxis or therapy can be accomplished by a single direct injection at a single time point or multiple time points to a single or multiple sites. Administration can also be nearly simultaneous to multiple sites.

Patients or subjects include mammals, such as human, bovine, equine, canine, feline, porcine, and ovine animals. The subject is preferably a human, and may or may not be afflicted with cancer or disease.

In some embodiments, the condition to be treated or prevented is cancer or a precancerous condition (e.g., hyperplasia, metaplasia, dysplasia). Example of cancer include, but are not limited to, fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, Waldenstrom's macroglobulinemia, and heavy chain disease.

In some embodiments, the condition to be treated or prevented is an infectious disease. Examples of infectious disease include, but are not limited to, infection with a pathogen, virus, bacterium, fungus or parasite. Examples of viruses include, but are not limited to, hepatitis type B or type C, influenza, varicella, adenovirus, herpes simplex virus type I or type II, rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus type I or type II. Examples of bacteria include, but are not limited to, *M. tuberculosis*, mycobacterium, mycoplasma, neisseria and legionella. Examples of parasites include, but are not limited to, rickettsia and chlamydia.

Accordingly, the above pharmaceutical compositions and vaccines may be used to prevent the development of a cancer or infectious disease or to treat a patient afflicted with a cancer or infectious disease. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors or infected cells with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. In a preferred embodiment, dendritic cells are modified in vitro to present the polypeptide, and these modified APCs are administered to the subject. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy.

In particular, antigen-presenting cells, such as dendritic, macrophage, monocyte, fibroblast and/or B cells, can be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Cultured effector cells can be induced to grow in vivo and to survive long term in substantial numbers by repeated stimulation with antigen supplemented with IL-2 (see, for example, Cheever et al., Immunological Reviews 157:177, 1997).

Alternatively, a vector expressing a polypeptide recited herein can be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumoral administration.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit infection or disease due to infection. Thus, the composition is administered to a subject in an amount sufficient to elicit an effective immune response to the specific antigens and/or to alleviate, reduce, cure or at least partially arrest symptoms and/or complications from the disease or infection. An amount adequate to accomplish this is defined as a "therapeutically effective dose."

Routes and frequency of administration of the therapeutic compositions disclosed herein, as well as dosage, will vary from individual to individual, and may be readily established using standard techniques. In general, the pharmaceutical compositions and vaccines may be administered, by injection (e.g., intracutaneous, intratumoral, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 intradermal injections of the composition are administered 10 days apart.

A suitable dose is an amount of a compound that, when administered as described above, is capable of promoting an anti-tumor immune response, and is at least 10-50% above the basal (i.e., untreated) level. Such response can be monitored, for example, by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to nonvaccinated patients. In general, for pharmaceutical compositions and vaccines comprising one or more polypeptides, the amount of each polypeptide present in a dose ranges from about 100 µg to 5 mg per kg of host. Suitable volumes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

EXAMPLES

The following examples are presented to illustrate the present invention and to assist one of ordinary skill in making and using the same. The examples are not intended in any way to otherwise limit the scope of the invention.

Example 1

Purification of hsp110, grp170 and grp78

This example describes the procedure for purification of hsp110 and grp170, as well as for grp78. The results confirm the identity and purity of the preparations.

Materials and Methods

A cell pellet or tissue was homogenized in 5 vol. of hypotonic buffer (30 mM sodium bicarbonate, pH7.2, 1 mM PMSF) by Dounce homogenization. The lysate was centrifuged at 4500 g and then 100,000 g to remove unbroken cells, nuclei, and other tissue debris. The supernatant was further centrifuged at 100,000 g for 2 hours. Supernatant was applied to concanavalin A-sepharose beads (1 ml bed volume/ml of original material), previously equilibrated with 20 mM Tris-HCl, 50 mM NaCl, 1 mM MgCl2, 1 mM CaCl2, 1 mM MnCl$_2$. The bound proteins were eluted with binding buffer A containing 15% a-D-methylmannoside (a-D-MM).

For purification of Hsp110, ConA-sepharose unbound material was applied to a Mono Q (Pharmacia) 10/10 column equilibrated with 20 mM Tris-HCl, pH 7.5, 200 mM NaCl. The bound proteins were eluted with the same buffer by a linear salt gradient up to 500 nM sodium chloride (FR:3 ml/min, 40%-60% B/60min). Fractions were collected and analyzed by SDS-PAGE followed by immunoblotting with an anti-hsp110 antibody. Pooled fractions containing hsp 110 (270 mM~300 mM) were concentrated by Centriplus (Amicon, Beverly, Mass.) and applied on a Superose 12 column. Proteins were eluted by 40 mM Tris HCl, pH 8.0, 150 mM NaCl with flow rate of 0.2 ml/min. Fractions were tested by immunoblot and silver staining.

For purification of Grp170, Con A-sepharose bound material, eluted by 10% αmethylmannoside, was first applied on MonoQ column equilibrated with 20 mM Tris HCl, pH 7.5, 150 mM NaCl and eluted by 150~500 mM NaCl gradient. Grp170 was eluted between 300mM~350 mM NaCl. Pooled fractions were concentrated and applied on the Superose 12 column. Fractions containing homogeneous grp170 were collected, and analyzed by SDS-PAGE followed by immunoblotting with an anti-grp170 antibody.

For purification of Grp78 (Bip), ConA-sepharose unbound proteins were loaded on an ADP-agarose column (Sigma Chemical Co., St. Louis, Mo.) equilibrated with binding buffer B (20 mM Tris-acetate, pH 7.5, 20 mM NaCl, 15 mM β-mercaptoethanol, 3 mM MgCl2, 0.5 mM PMSF). The column was washed with binding buffer B containing 0.5 M NaCl, and incubated with buffer B containing 5 mM ADP at room temperature for 30 min. Protein was subsequently eluted with the same buffer (~5 times bed volume). The elute was resolved on a FPLC system using MonoQ column and eluted by a 20-500 mM NaCl gradient. Grp78 was present in fractions eluted between 200 mM-400 mM salt. For purification of Hsp or Grps from liver, the 100,000 g supernatant was first applied to a blue sepharose column (Pharmacia) to remove albumin. All protein was quantified with a Bradford assay (BioRad, Richmond, Calif.), and analyzed by SDS-PAGE followed by immunoblotting with antibodies to grp78 obtained from StressGen Biotechnologies Corp. (Victoria, BC, Canada).

Results

Figure 1B:
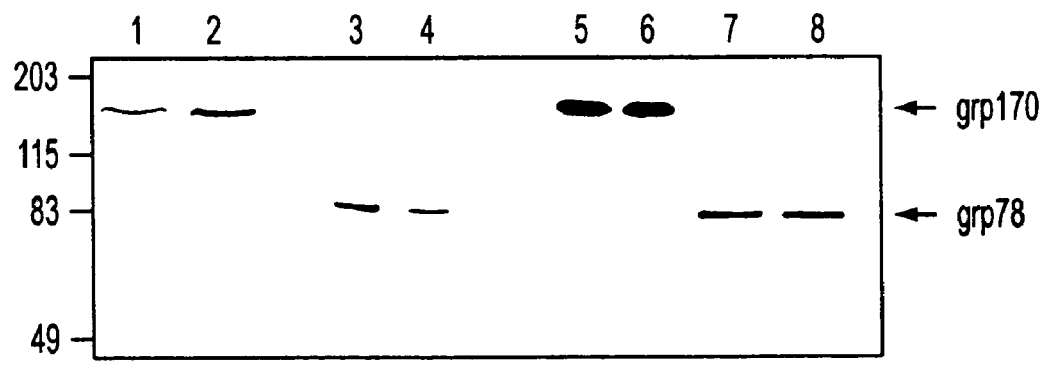
FIG. 1B shows silver staining and analysis of purified grp proteins, with gel staining of grp170 from tumor in lane 1, of grp170 from liver in lane 2, grp78 from tumor in lane 3, grp78 from liver in lane 4. Results of an immunoblot analysis with grp170 antibody and grp78 antibody, respectively, are shown in lanes 5-6 and 7-8.

Proteins hsp110, grp170 and grp78 were purified simultaneously from tumor and liver. Homogeneous preparations for these three proteins were obtained and they were recognized by their respective antibodies by immunoblotting. The purity of the proteins was assessed by SDS-PAGE and silver staining (FIG. 1).

Example 2

Tumor Rejection Assays

This example demonstrates that immuunization with tumor derived hsp110 and grp170 protects mice against tumor challenge. The results show tumor growth delay with prophylactic immunization as well as longer survival times with therapeutic immunization.

Materials and Methods

BALB/cJ mice (viral antigen free) were obtained from The Jackson Laboratory (Bar Harbor, Me.) and were maintained in the mouse facilities at Roswell Park Cancer Institute. Methylcholanthrene-induced fibrosarcoma (Meth A) was obtained from Dr. Pramod K. Srivastava (University of Connecticut School of Medicine, Farmington, Conn.) and maintained in ascites form in BALB/cJ mice by weekly passage of 2 million cells.

Mice (6-8-week-old females; five mice per group) were immunized with PBS or with varying quantities of tumor or liver derived hsp110 or grp170, in 200 μl PBS, and boosted 7 days later. Seven days after the last immunization, mice were injected subcutaneously on the right flank with $2 \times 10^4$ colon 26 tumor cells (viability>99%). The colon 26 tumor exemplifies a murine tumor model that is highly resistant to therapy. In other experiments, the mice were challenged 7 days after the second immunization with intradermal injections of MethA tumor cells. Tumor growth was monitored by measuring the two diameters.

Results

Figure 2A:
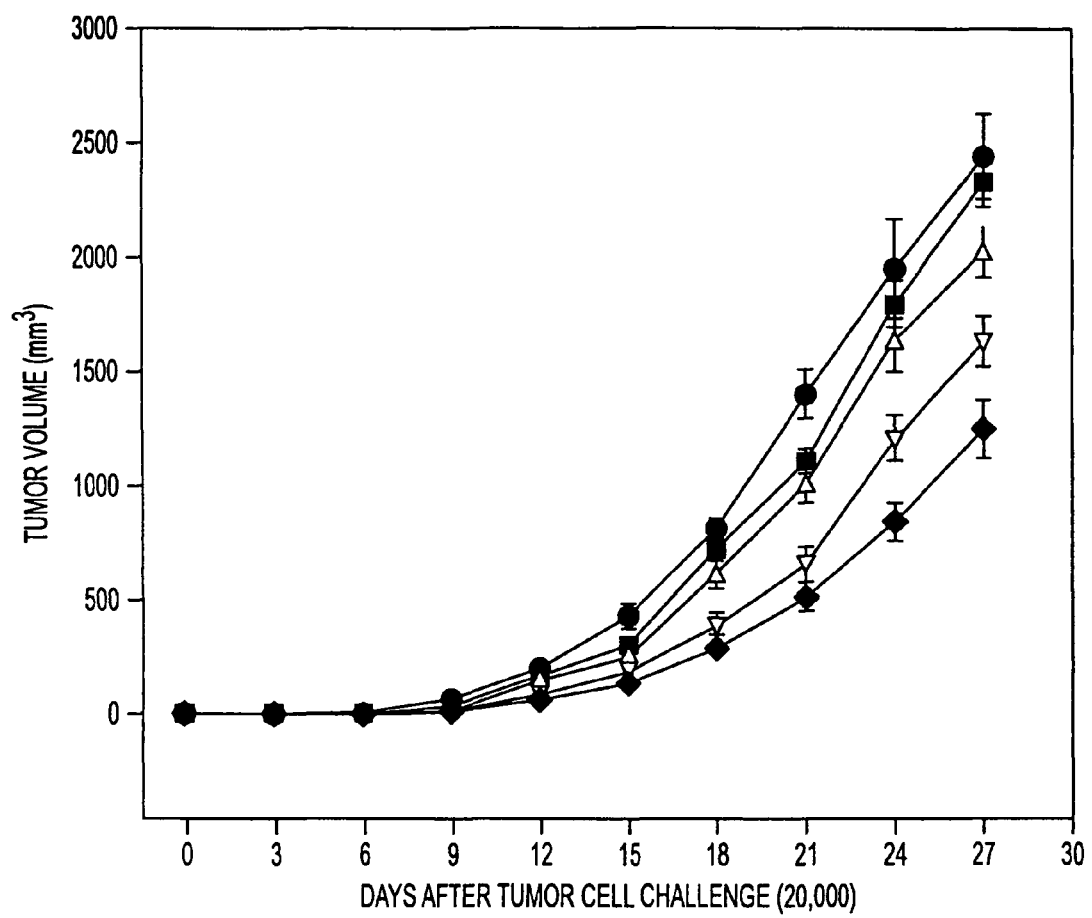
FIG. 2A shows tumor growth after immunization with purified hsp110. Tumor volume, in cubic millimeters, is plotted against the number of days after challenge with 20,000 colon 26 tumor cells, for mice immunized with PBS (circles), 40 µg of liver-derived hsp110 (squares), 20 µg of tumor derived hsp110 (upward triangles), 40 µg of tumor derived hsp110 (downward triangles) and 60 µg of tumor derived hsp110 (diamonds).
Figure 2B:
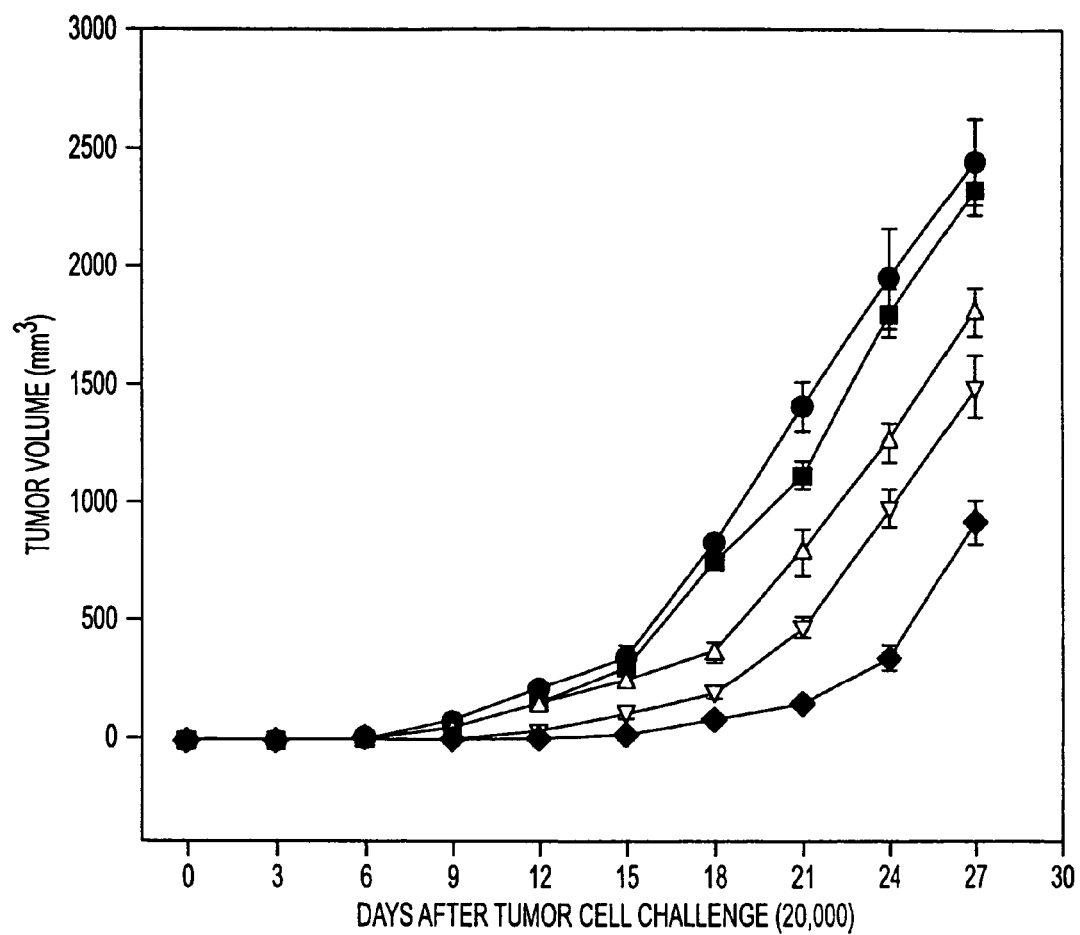
FIG. 2B shows tumor growth after immunization with purified grp170. Tumor volume, in cubic millimeters, is plotted against the number of days after challenge with 20,000 colon 26 tumor cells, for mice immunized with PBS (circles), 40 µg of liver-derived grp170 (squares), 20 µg of tumor derived grp170 (upward triangles), 40 µg of tumor derived grp170 (downward triangles) and 60 µg of tumor derived grp170 (diamonds).

The results of vaccination with hsp110 and grp170 are presented in FIGS. 2A and 2B, respectively. All mice that were immunized with PBS and liver derived hsp110 or grp170 developed rapidly growing tumors. In contrast, mice immunized with tumor derived hsp110 and grp170 showed a significant tumor growth delay. Thus, hsp110 or grp170 that is complexed with tumor proteins significantly inhibits tumor growth.

The inhibition effect was directly dependent on the dose of tumor derived hsp110 or grp170. Mice immunized with 20 μg (per injection) of hsp110 or grp170 showed slight or no inhibition of colon 26 tumor growth, while those immunized with 40 or 60 μg of hsp110 or grp170 showed increasingly significant tumor growth delay. On each day examined (15, 21, 27 days after challenge), the mean volumes of the tumors that developed in mice immunized with hsp110 and grp170 at doses of 40 and 60 μg were significantly smaller than those of control mice (p<0.01, student's t test). However, the differences in the mean volumes of the groups injected with PBS or liver derived hsp preparations did not reach statistical significance. Additional tumor rejection assays were performed by challenging mice with larger quantities of tumor cells (50,000 and 100,000). Similar inhibitory results were obtained for tumor derived hsp110 or grp170, although, as expected, these tumors grew more rapidly. Although grp170 was purified by conA-sepharose column, a contamination with conA can be ruled out because the protective immunity could only be observed in the mice immunized with grp170 preparations from tumor but not normal liver tissue.

On an equal molar, quantitative basis, grp170 appears to be more immunogenic than hsp110. The immunogenicity of grp78 was also tested by injecting 40 μg of protein, but no tumor growth delay was observed. These results indicate that grp78 is either not immunogenic, or is so at a low level only.

To test the generality of those observations in other systems, the immunogenicity of hsp110 and grp170 were tested in the methylcholanthrene-induced (MethA) fibrosarcoma. Based on the immunization data in colon 26 tumor model, mice were immunized twice with 40 μg hsp110 or grp170, and challenged with 100,000 MethA cells introduced by intradermal injection.

Figure 4C:
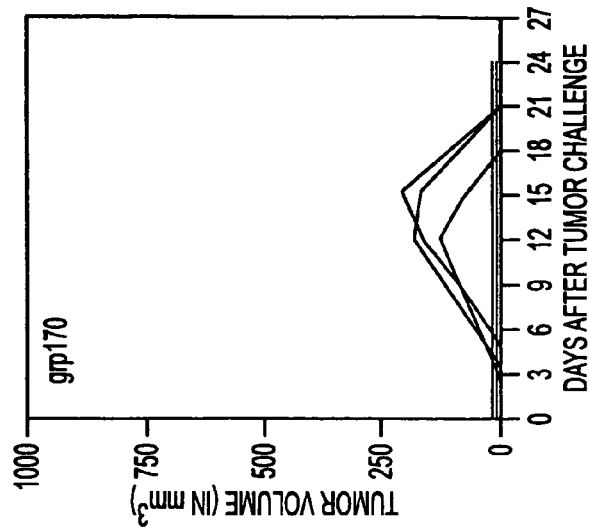
FIG. 4C is a graph depicting tumor size as a function of days after tumor challenge in mice immunized with grp170 derived from MethA-induced tumor. Individual lines represent individual mice to show variations between animals.
Figure 4B:
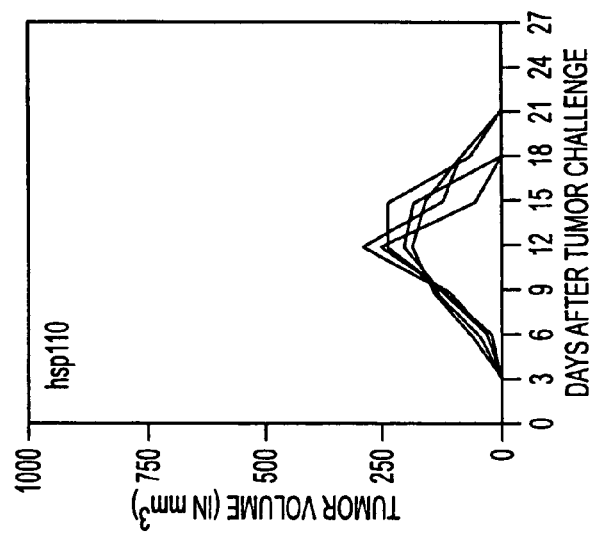
FIG. 4B is a graph depicting tumor size as a function of days after tumor challenge in mice immunized with hsp110 derived from MethA-induced tumor. Individual lines represent individual mice to show variations between animals.
Figure 4A:
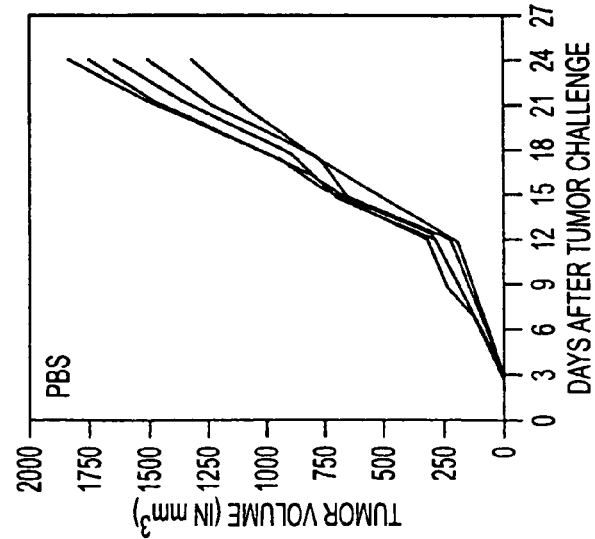
FIG. 4A is a graph depicting tumor size as a function of days after tumor challenge in mice immunized with PBS (control). Individual lines represent individual mice to show variations between animals.
Figure 5A:
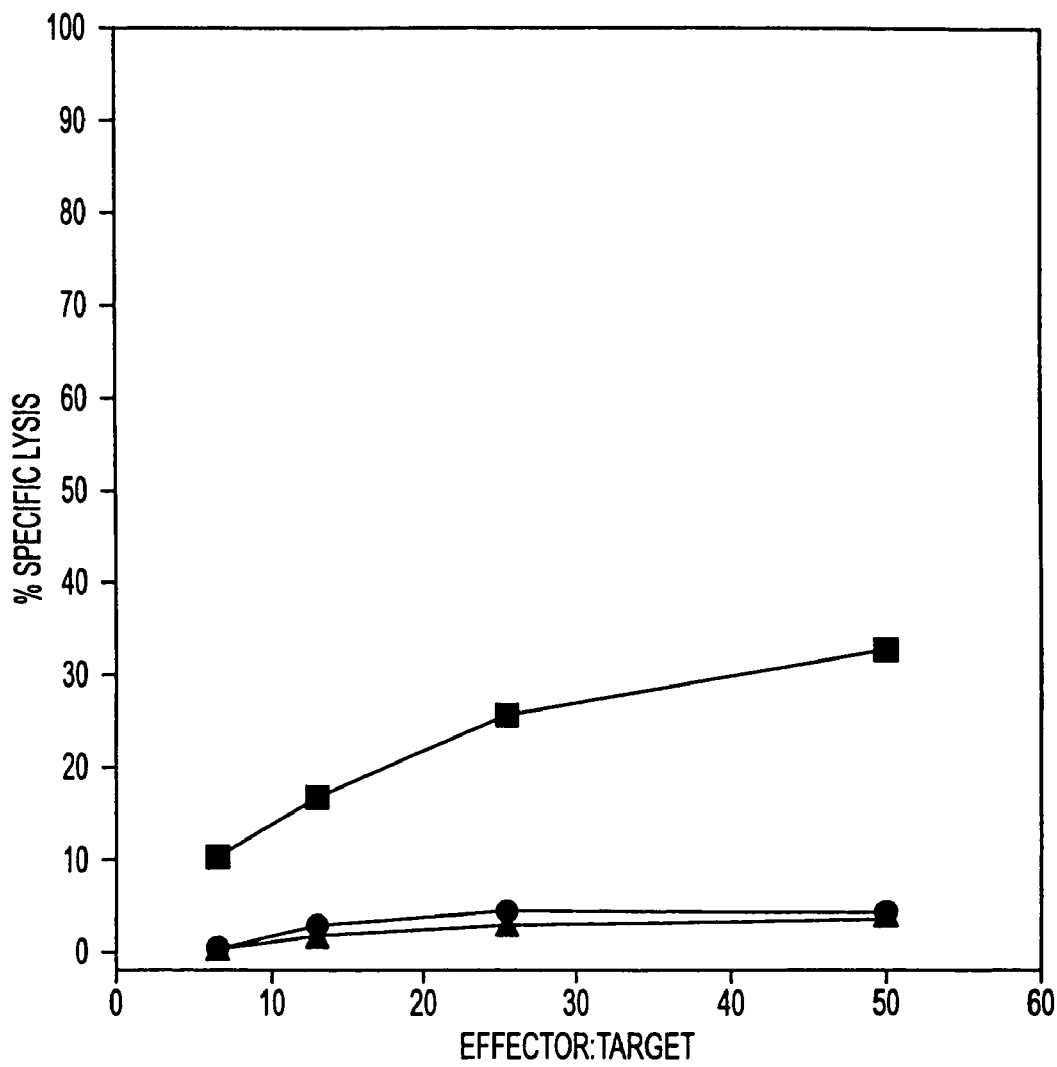
FIG. 5A is a graph showing results of a CTL assay targeting colon 26 tumor cells. Percent specific lysis is plotted as a function of effector:target ratio for control T cells (circles), T cells directed against hsp110 derived from colon 26 tumor cells (squares), and T cells directed against hsp110 derived from MethA tumor cells.
Figure 5B:
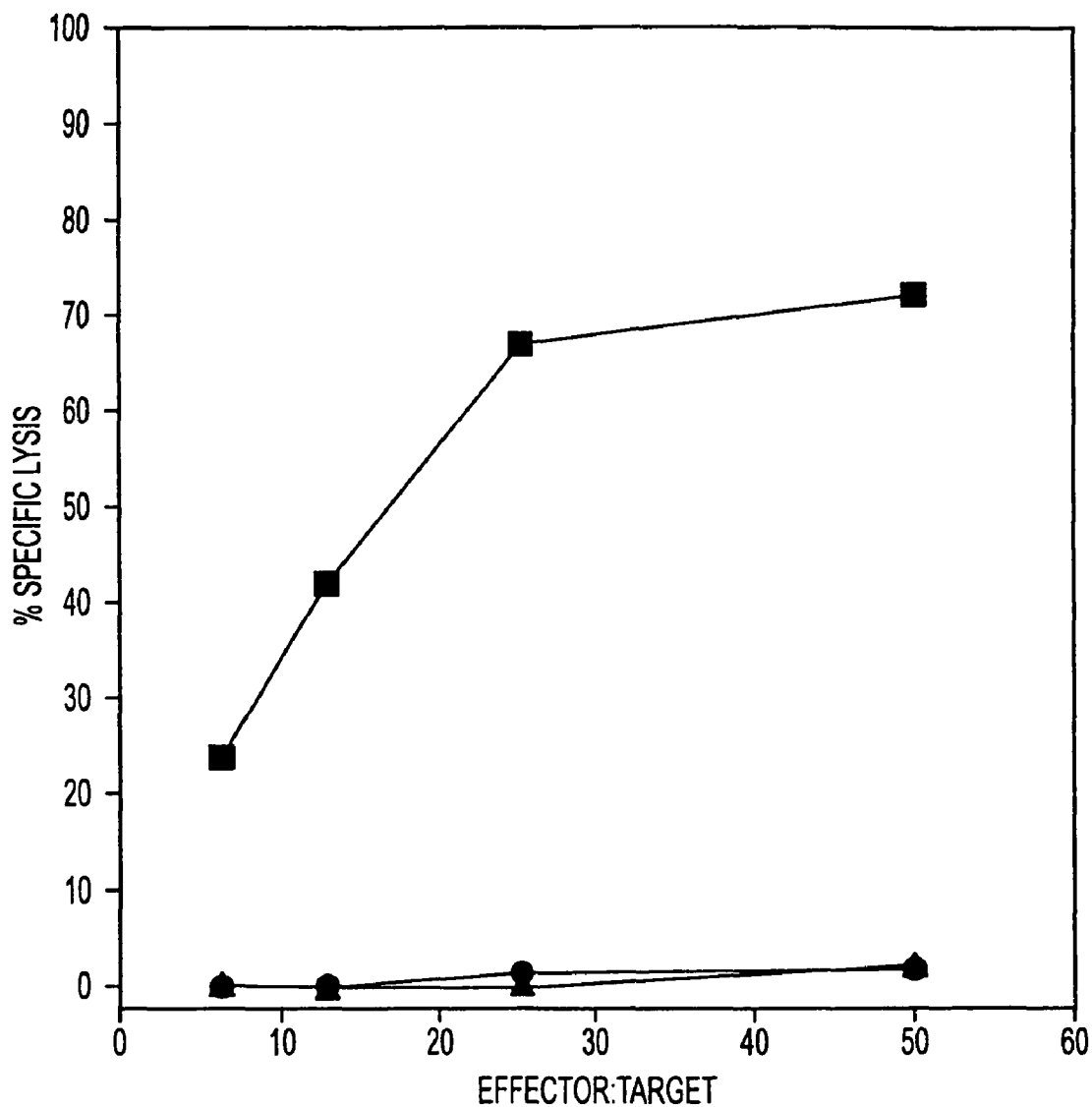
FIG. 5B is a graph showing results of a CTL assay targeting colon 26 tumor cells. Percent specific lysis is plotted as a function of effector:target ratio for control T cells (circles), T cells directed against grp170 derived from colon 26 tumor cells (squares), and T cells directed against grp170 derived from MethA tumor cells.
Figure 5C:
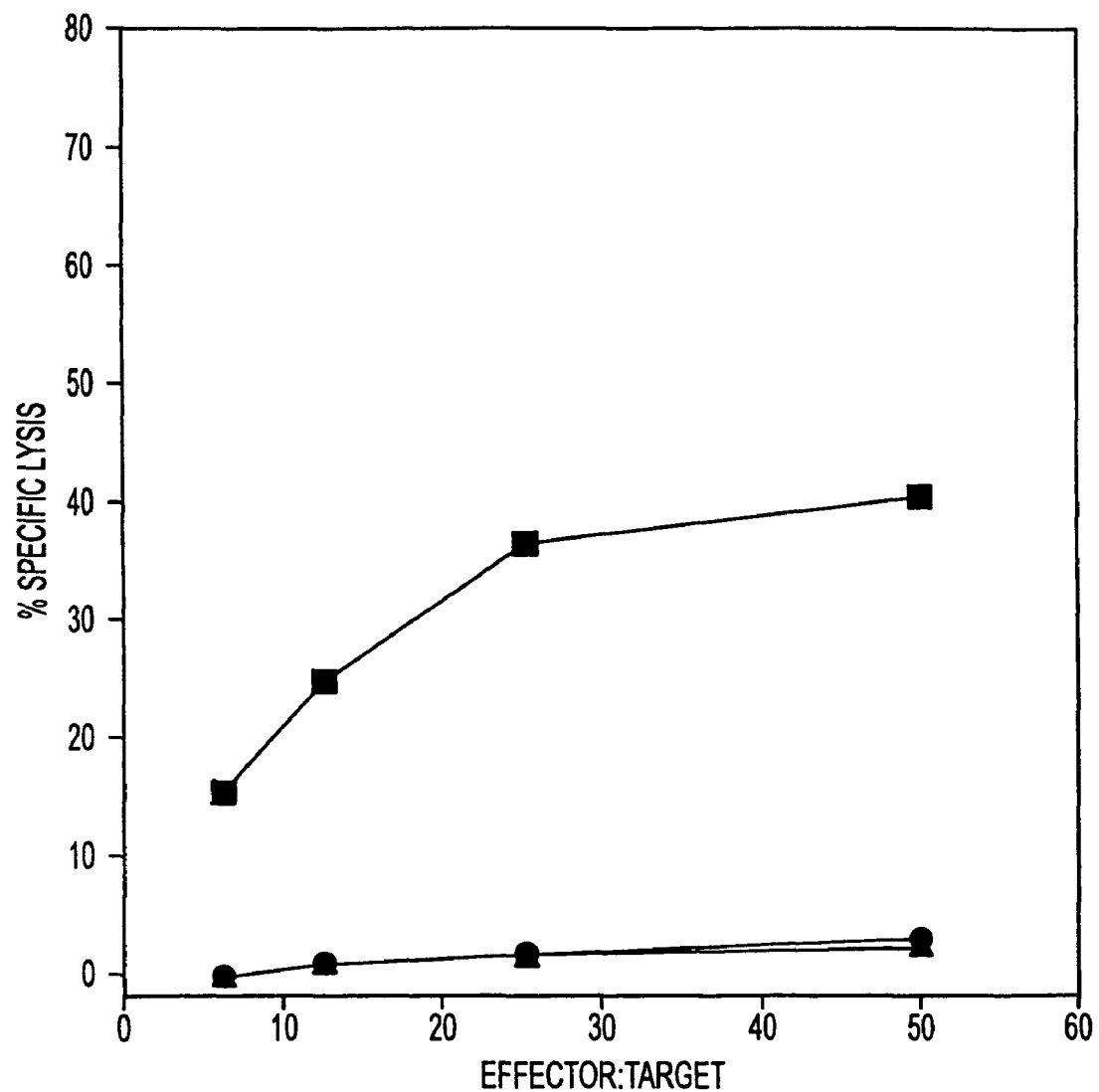
FIG. 5C is a graph showing results of a CTL assay targeting MethA tumor cells. Percent specific lysis is plotted as a function of effector:target ratio for control T cells (circles), T cells directed against hsp110 derived from colon 26 tumor cells (squares), and T cells directed against hsp110 derived from MethA tumor cells.
Figure 5D:
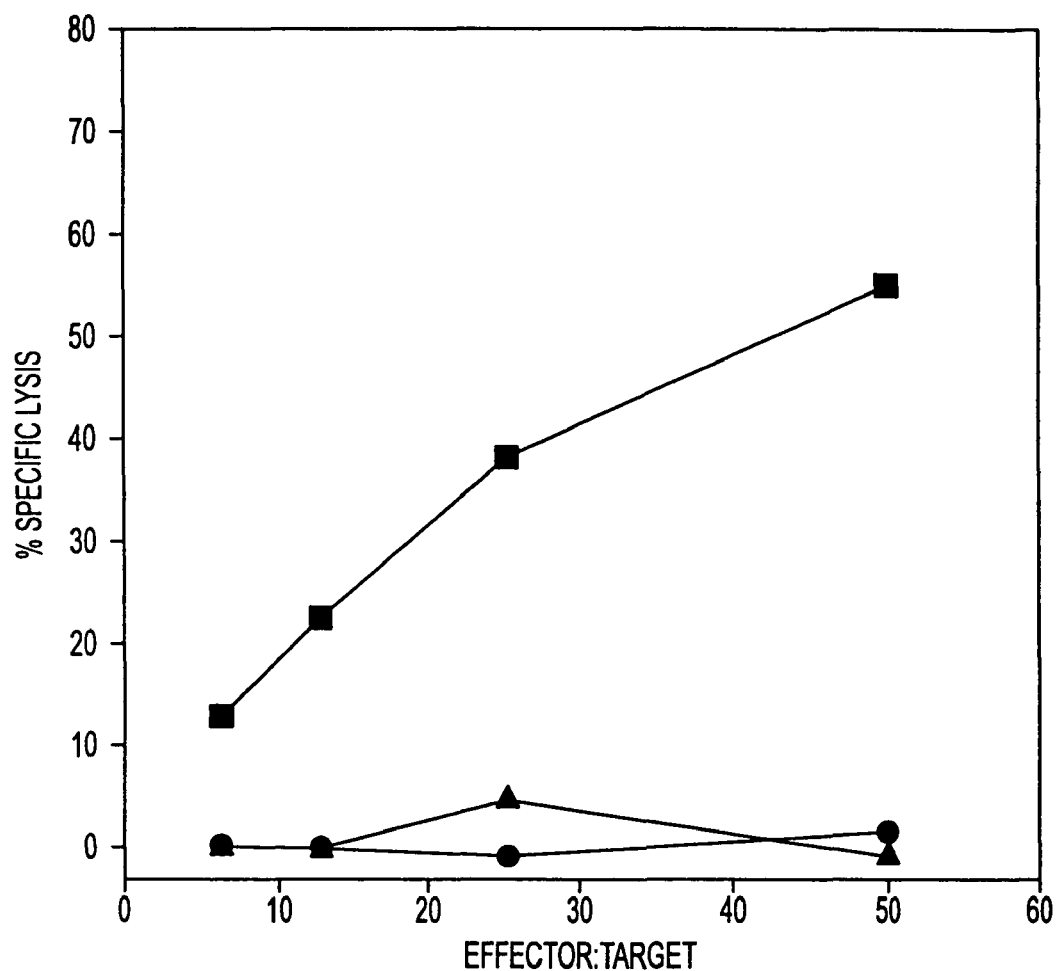
FIG. 5D is a graph showing results of a CTL assay targeting MethA tumor cells. Percent specific lysis is plotted as a function of effector:target ratio for control T cells (circles), T cells directed against grp170 derived from colon 26 tumor cells (squares), and T cells directed against grp170 derived from MethA tumor cells.

Line representations in FIGS. 4A-4C show the kinetics of tumor growth in each individual animal. Notable differences between individuals in tumor growth in response to immunization was observed in the grp170 group. Mice immunized with PBS developed MethA tumors (FIG. 4A). However, mice immunized with hsp110 (FIG. 4B) or grp170 (FIG. 4C) were protected. While most animals initially developed tumors, the tumors later disappeared. In the mice that were immunized with grp170, two of five mice completely failed to develop a palpable tumor (FIG. 4C).

Therapeutic Immunization

The aggressive colon 26 tumor was also examined in a therapy model. Tumor cells (500,000) were injected into the flank area and mice (10 per group) were vaccinated two times (separated by 7 days) with liver or colon 26 derived hsp110 or grp170, starting when the tumor was visible and palpable (e.g., day 6). The survival of mice was recorded as the percentage of mice surviving after the tumor challenge at various times.

Figure 3A:
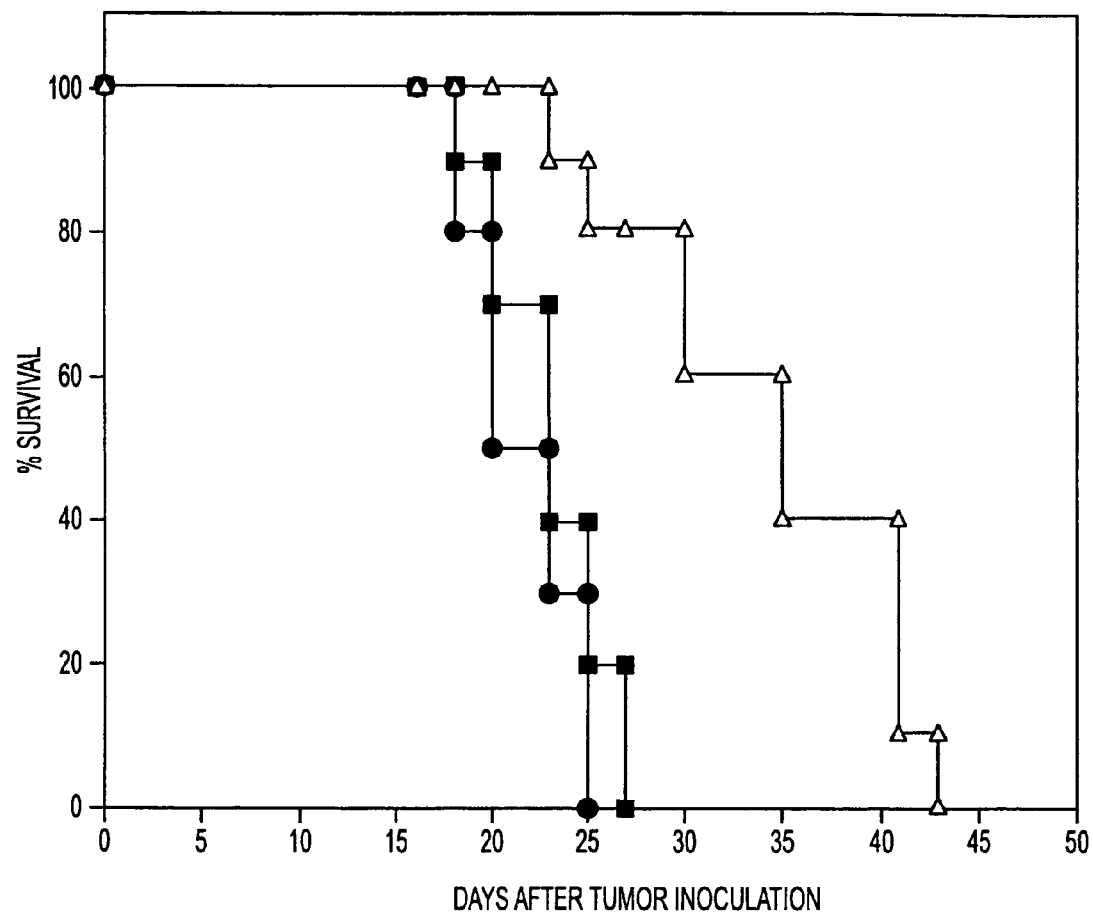
FIG. 3A is a plot showing the survival of Balb/C mice bearing colon 26 tumors after immunization with tumor derived hsp110. Percent survival is plotted as a function of days after tumor inoculation for mice immunized with PBS (control, circles), 40 µg liver-derived hsp110 (squares), and 40 µg tumor derived hsp110 (triangles).
Figure 3B:
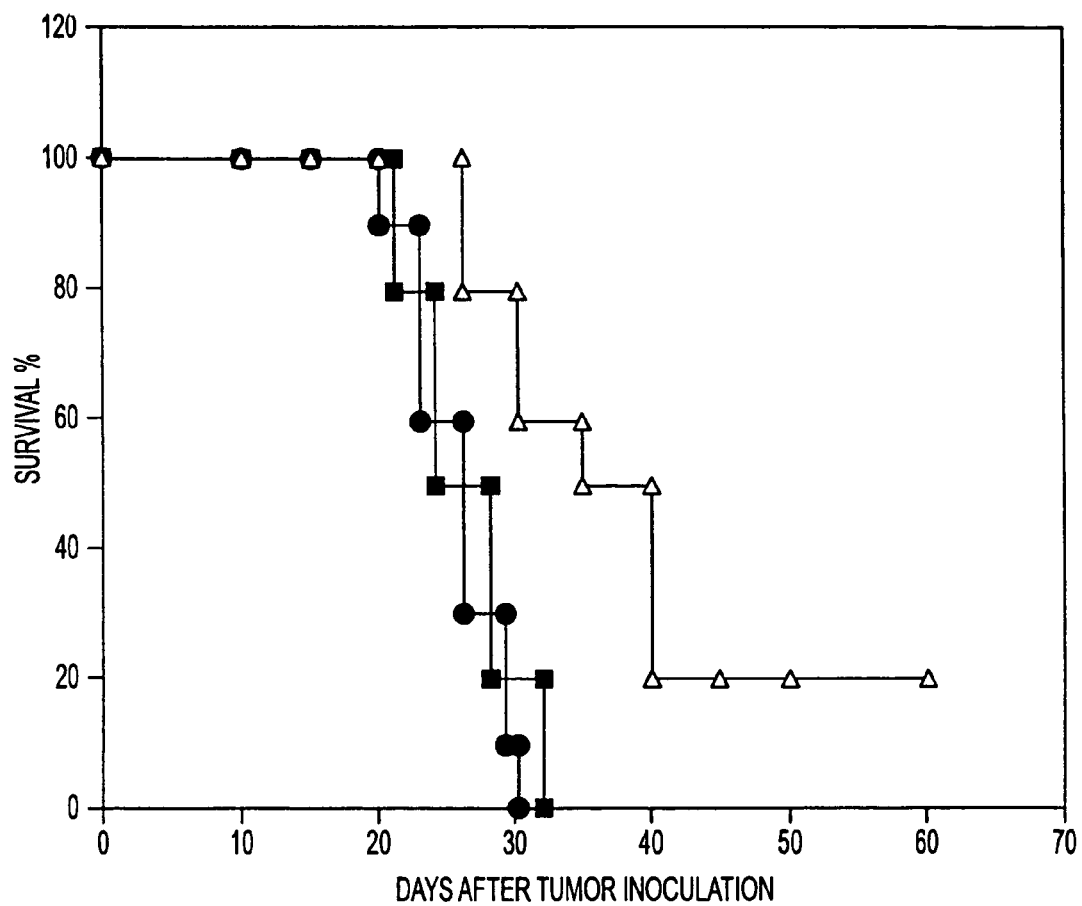
FIG. 3B is a plot showing the survival of Balb/C mice bearing colon 26 tumors after immunization with tumor derived grp170. Percent survival is plotted as a function of days after tumor inoculation for mice immunized with PBS (control, circles), 40 µg liver-derived grp170 (squares), and 40 µg tumor derived grp170 (triangles).

The results are shown in FIGS. 3A and 3B. Tumor bearing mice treated with autologous hsp110 (FIG. 3A) or grp170 (FIG. 3B) preparations showed significantly longer survival times compared to the untreated mice or mice immunized with liver derived hsp110 or grp170. All the control animals died within 30 days, but approximately one-half of each group survived to 40 days, and 20% of grp170 treated mice survived to 60 days. These results are consistent with the data obtained from the tumor injection assay, and again indicate that grp170 and hsp110 are effective anti-cancer vaccines. These data also show that grp170 appears to be the more efficient of the two proteins on an equal molar basis.

Example 3

CTL Assay

Because cellular immunity appears to be critical in mediating antitumor effects, a cytotoxic T lymphocyte (CTL) assay was performed to analyze the ability of tumor derived hsp110 or grp170 preparations to elicit a CD8+ T cell response. The results show that vaccination with tumor derived hsp110 or grp170 elicits an effective tumor specific CTL response.

Materials and Methods

Mice were immunized twice as described above. Ten days after the second immunization, spleens were removed and spleen cells ($1 \times 10^7$) were co-cultured in a mixed lymphocyte-tumor culture (MLTC) with irradiated tumor cells ($5 \times 10^5$) used for immunization for 7 days, supplemented with 10% FCS, 1% penicillin/streptomycin, 1 mM sodium pyruvate and 50 μM 2-mercaptoethanol. Splenocytes were then purified by Ficoll-Paque (Pharmacia) density centrifugation and utilized as effector cells. Cell-mediated lysis was determined in vitro using a standard $^{51}$Chromium-release assay. Briefly, effector cells were serially diluted in 96 V-bottomed well plates (Costar, Cambridge, Mass.) in triplicate with varying effector: target ratios of 50:1, 25:1, 12.5:1 and 6.25:1. Target cells ($5 \times 10^6$) were labeled with 100 μCi of sodium [$^{51}$Cr]chromate at 37° C. for 1-2 h. $^{51}$Cr-labeled tumor cells (5,000) were added to a final volume of 200 μl/well.

Wells that contained only target cells, with either culture medium or 0.5% Triton X-100, served as spontaneous or maximal release controls, respectively. After 4 h incubation at 37° C. and 5% $CO_2$, 150 μl supernatant was analyzed for radioactivity in a gamma counter. Percentage of specific lysis was calculated by the formula: percent specific lysis=100× (experimental release−spontaneous release)/(maximum release−spontaneous release). The spontaneous release was <10% of maximum release.

Results

As shown in FIGS. 5, tumor-specific cytotoxicity against the tumor that was used for grp170 or hsp110 purification was observed. However, cells from naive mice were unable to lyse target cells. Furthermore, splenocytes from mice immunized with colon 26 derived hsp110 or grp170 preparations showed specific lysis for colon 26 tumor, but not MethA tumor cells. Likewise, MethA derived hsp110 or grp170 showed specific lysis for MethA but not colon 26 cells. These results demonstrate that vaccination with tumor derived hsp110 or grp170 elicits an effective tumor specific CTL response.

Example 4

Vaccination with Dendritic Cells Pulsed with Tumor derived Protein

This example demonstrates the capacity of antigen presenting cells to play a role in the anti-tumor response elicited by hsp110 or grp170 immunization. The results show the ability of dendritic cells (DCs) to represent the hsp110 or grp170 chaperoned peptides. Moreover, immunotherapy with hsp110 or grp170 pulsed DC was more efficient than direct immunization with protein.

Materials and Methods

Bone marrow was flushed from the long bones of the limbs and depleted of red cells with ammonium chloride. Leukocytes were plated in bacteriological petri dishes at $2\times10^6$ per dish in 10 ml of RPMI-10 supplemented with 200 U/ml (=20 ng/ml) murine GM-CSF (R&D System), 10 mM HEPES, 2 mM L-glutamine, 100 U/mi penicillin, 100 μg/mi streptomycin, 50 mM 2-mercaptoethanol. The medium was replaced on days 3 and 6. On day 8, the cells were harvested for use. The quality of DC preparation was characterized by cell surface marker analysis and morphological analysis. DCs ($1\times10^7$/ml) were pulsed with tumor derived hsp110 or grp170 (200 μg) for 3 hrs at 37° C. The cells were washed and resuspended in PBS ($10^6$ pulsed DCs in 100 μl PBS per mouse) for intraperitoneal injection. The entire process was repeated 10 days later, for a total of two immunizations per treated mouse. Ten days after the second immunization, mice were challenged with colon 26 tumor cells ($2\times10^4$).

Results

Figure 6:
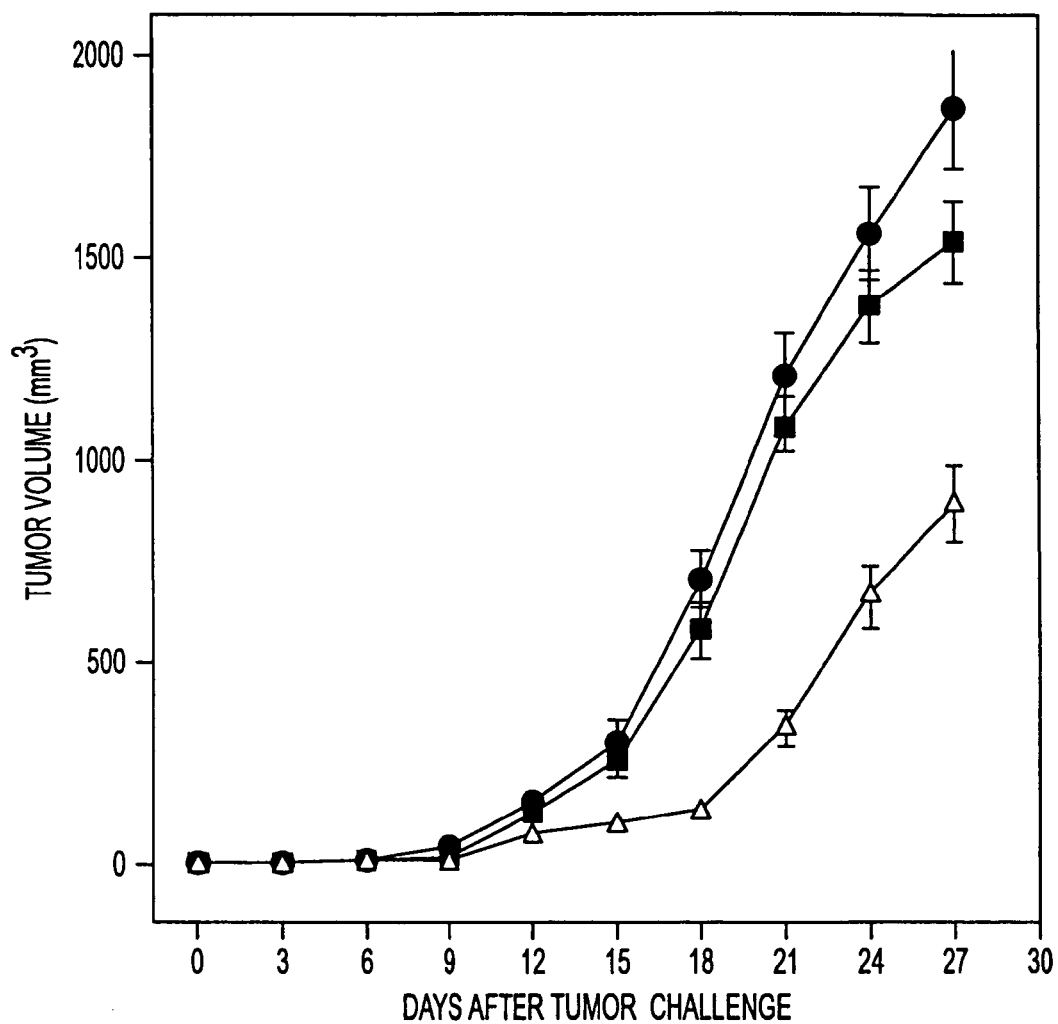
FIG. 6 is a graph showing tumor volume, in cubic millimeters, as a function of days after tumor challenge in mice immunized with grp170-pulsed dendritic cells (triangles), control dendritic cells (squares), or PBS (circles).

Tumors grew aggressively in the mice that received PBS or dendritic cells alone (FIG. 6). However, in mice immunized with tumor derived hsp110 or grp170 pulsed DCs, a significant slowing of tumor growth was observed. These results parallel the direct immunization studies with hsp110 or grp170. Comparison of direct immunization with protein (2 subcutaneous injections of 40 μg protein) versus immunization with pulsed DCs ($10^6$ DCs pulsed with 20 μg protein) suggests that pulsed DC based immunotherapy is more efficient, as it was more effective and used less protein.

Example 5

Production of More Effective Vaccines Through Heat Treatment

This example demonstrates that stress proteins purified from heat-treated tumors are even more effective at reducing tumor size than stress proteins purified from non-heat-treated tumors. This increased efficacy may reflect improved peptide binding at higher temperatures as well as other heat-induced changes.

Mice were first inoculated subcutaneously with 100,000 colon 26 tumor cells on the flank area. After the tumors reached a size of approximately 1/1 cm, WBH was carried out as described before. Briefly, mice were placed in microisolater cages preheated to 38° C. that contained food, bedding and water. The cages were then placed in a gravity convection oven (Memmert model BE500, East Troy, Wis.) with preheated incoming fresh air. The body temperature was gradually increased 1° C. every 30 minutes until a core temperature of 39.5° C. (±0.5 C) was achieved. Mice were kept in the oven for 6 hours. The core temperature of the mice was monitored with the Electric laboratory Animal Monitoring system Pocket Scanner (Maywood, N.J.). Tumors were removed on the next day for purification of hsp110, grp170 and hsp70. Immunizations were performed as above, twice at weekly intervals, using PBS, 40 μg hsp110 derived from tumors, 40 μg hsp110 derived from WBH-treated tumor, 40 μg grp170 derived from tumors, 40 μg grp170 derived from WBH-treated tumor, 40 μg hsp70 derived from tumors, or 40 μg hsp70 derived from WBH-treated tumor. Mice were then challenged with 20,000 live colon 26 tumor cells. Tumor volume, in $mm^3$, was measured at 0, 3, 6, 9, 12, 15, 18 and 21 days after tumor challenge.

Figure 7:
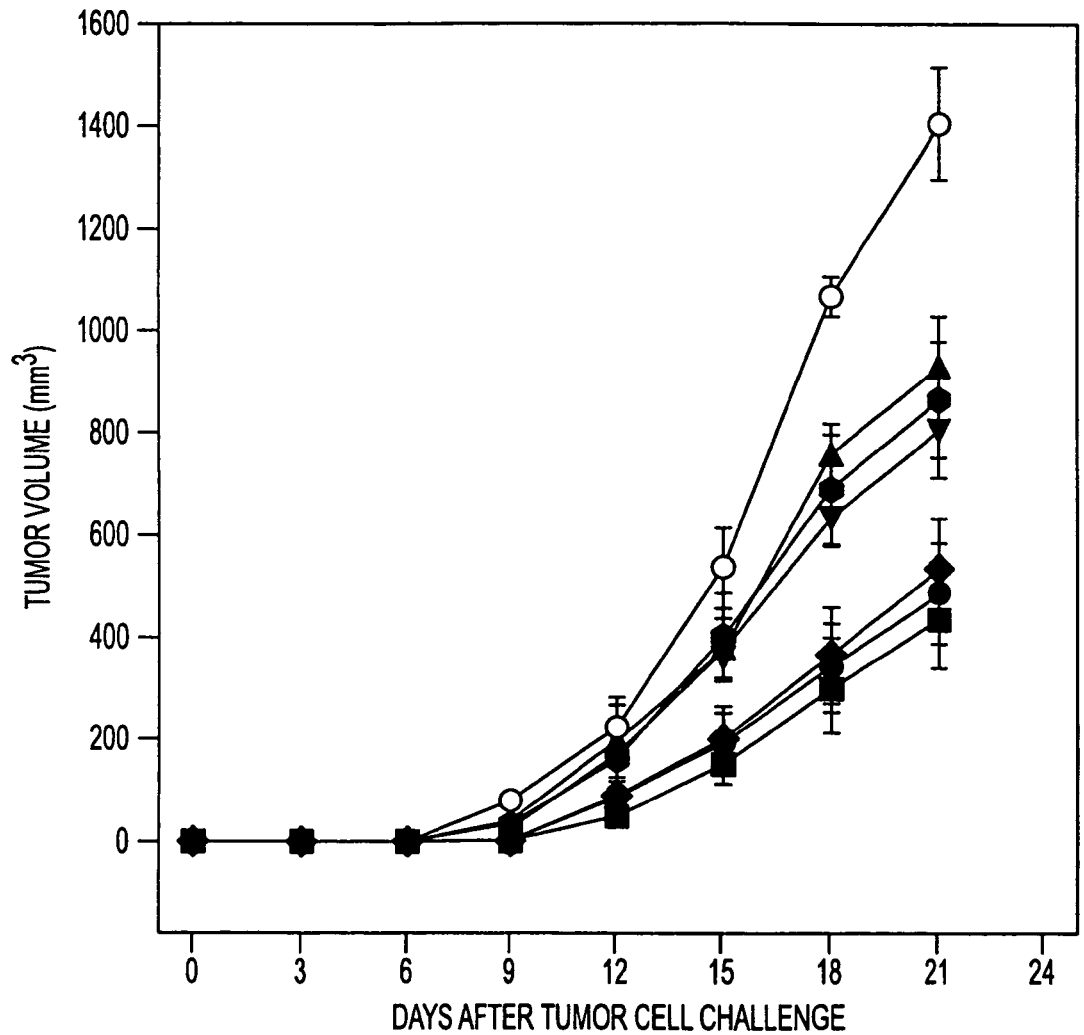
FIG. 7 is a graph showing tumor volume, in cubic millimeters, as a function of days after tumor challenge in mice immunized with PBS (open circles), grp170 derived from tumors (squares), grp170 derived from tumors of whole body heat-treated mice (upward triangles), hsp110 derived from tumors (downward triangles), hsp110 derived from tumors of whole body heat-treated mice (diamonds), hsp70 derived from tumors (hexagons), hsp70 derived from tumors of whole body heat-treated mice (solid circles).

The results are shown in FIG. 7. At 12 and 15 days after tumor challenge, both of the hsp110- and hsp70-treated groups showed significantly reduced tumor volume relative to PBS-treated mice. By 15 days following tumor challenge, hsp110 or hsp70 purified from WBH-treated tumor was significantly more effective at reducing tumor volume as compared to hsp110 or hsp70 purified from non-heat-treated tumor. However, by 15 days, grp170 purified from non-heat-treated tumor was more effective than grp170 from WBH-treated tumor.

These data indicate that fever-like exposures can influence the antigen presentation pathway and/or peptide binding properties of these two (heat inducible) hsps purified from colon 26 tumors but not a heat insensitive grp. Thus, the vaccine potential of hsp70 and hsp110 are significantly enhanced following fever level therapy. This could result from enhanced proteosome activity, enhanced peptide binding of the hsp, altered spectrum of peptides bound to the hsp, or other factors. Because the hsps were purified 16 hours after the 8-hour hyperthermic exposure, the effect is maintained for some time at 37° C. The factors leading to this enhanced immunogenicity likely derive from an altered and/or enhanced antigenic profile of hsp bound peptides. Stability following the hyperthermic episode suggests up-stream changes in antigen processing that are still present many hours later, e.g. stimulation of proteosome activity. Another feature of fever-like hyperthermia is the highly significant induction of hsps in colon 26 tumors. Therefore, fever-like heating not only provides a more efficient vaccine in the case of the hsps examined, but also a lot more of it. Finally, it is intriguing that the observed increase in vaccine efficiency resulting from hyperthermia is seen only for hsp110 and hsc70. Grp170, which is regulated by an alternative set of stress conditions such as anoxia and other reducing states, but not heat, is diminished in its vaccine potential by heat.

In addition to these observations, the data shown in FIG. 7 illustrate that grp170 purified from unheated, control tumors (mice) is significantly more efficient in its vaccine efficiency when compared on an equal mass basis to either hsp70 or hsp110 (without heat). This increased efficiency of grp170 compared to hsp110 is also reflected in the studies described above. This comparison is based on administration of equal masses of these proteins and the enhanced efficiency of grp170 is further exacerbated when molecular size is taken into account (i.e. comparisons made on a molar basis). Third, hsp70 is seen here to be approximately equivalent in its vaccine efficiency (again, on an equal mass but not equal molar basis) to hsp110.

Example 6

Chaperoning Activity of Grp170 and Hsp110

This example demonstrates, through a protein aggregation assay, the ability of grp170 and hsp110 to chaperone protein and prevent aggregation. The results show the increased efficiency of grp170 and hsp110 as compared to that demonstrated for hsp70 (Oh et al., 1997, J. Biol. Chem. 272:31636-31640).

The ability of the stress proteins to prevent protein aggregation induced by heat treatment was assessed by the suppression of the increase in light scattering obtained upon heat treatment in the presence of a reporter protein, firefly luciferase. Luciferase was incubated with equimolar amounts of hsp110 or grp170 at 43° C. for 30 minutes. Aggregation was monitored by measuring the increase of optical density at 320 nm. The optical density of the luciferase heated alone was set to 100%.

Figure 8:
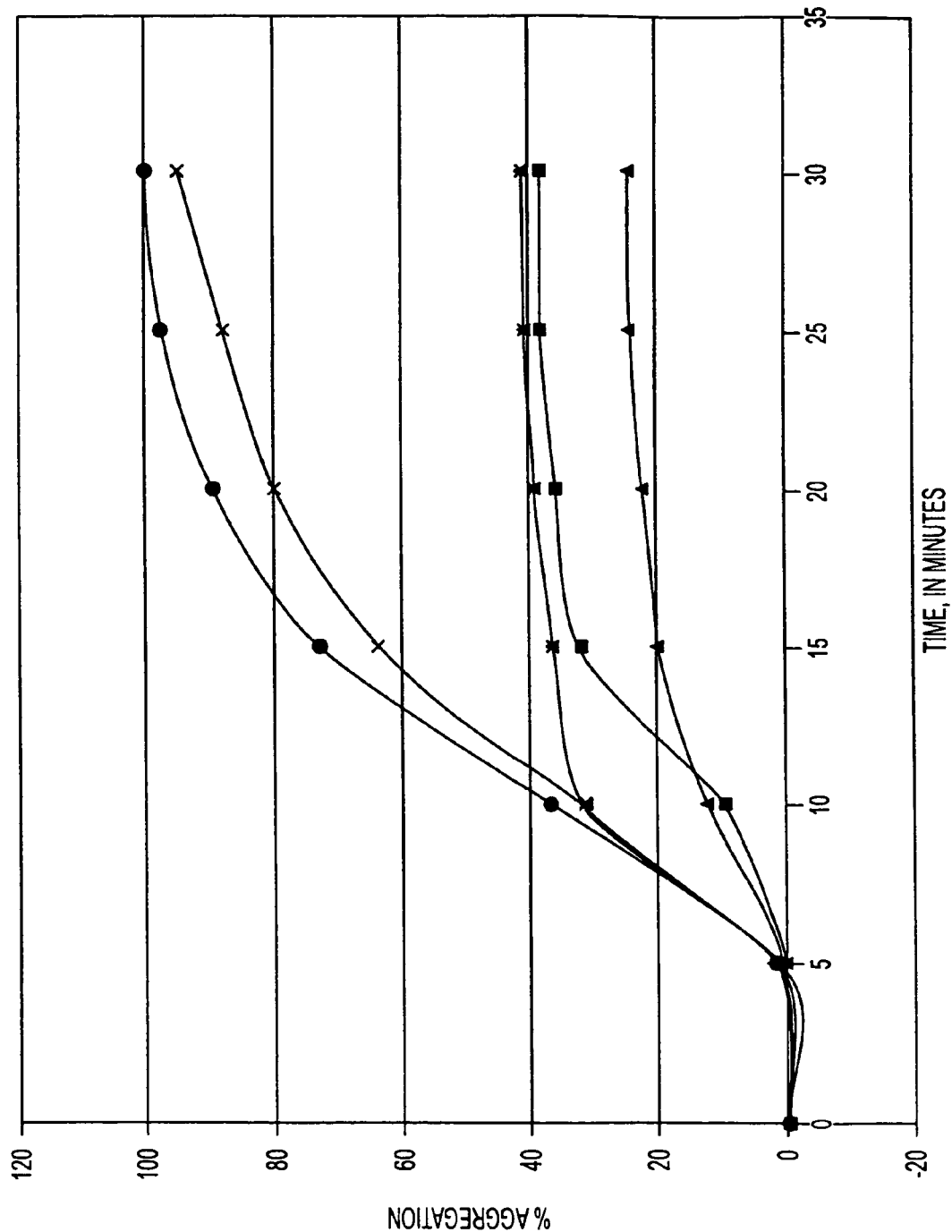
FIG. 8 is a graph showing percent protein aggregation (determined by light scattering) as a function of time, in minutes, for luciferase incubated with hsp110+hsp70+hsp25 at a molar ratio of 1:1:1:1 (squares), hsp110 at 1:1 (triangles), hsp25 at 1:1 (X's), grp170 at 1:1 (asterisks), or luciferase alone (circles).

The results are shown in FIG. 8. Hsp110 in a 1:1 molar ratio with luciferase limited aggregation to approximately 20% as compared to the 100% aggregation observed with luciferase alone. Grp170 in a 1:1 molar ratio with luciferase resulted in approximately 40% aggregation. These are the same conditions as used by Oh et al., 1997, J. Biol. Chem. 272:31636-31640, which resulted in 70% aggregation with hsp70 in a 1:1 molar ratio with luciferase. Thus, both grp170 and hsp110 demonstrate a greater efficiency than hsp70 in binding protein and preventing aggregation. Based on studies in which the loop domain of hsp110 was deleted (Oh et al., 1999, J. Biol. Chem. 272(22):15712-15718), this increased efficiency in chaperoning activity is likely attributable to the larger loop domain found in both hsp110 and grp170.

Hsp110 and grp170 both appear to exhibit a peptide binding cleft. However, hsp110 and grp170 differ dramatically from the hsp70s in their C-terminal domains which, in the case of hsp70 proteins, appears to function as a lid for the peptide binding cleft and may have an important influence on the properties of the bound peptide/protein and/or the affinity for the associated peptide/protein. Both hsp110 and grp170 appear to be more significantly efficient in binding to and stabilizing thermally denatured proteins relative to hsc70. This may reflect these structural differences and influence peptide binding properties, a factor in the ability of stress proteins to function as vaccines. While hsp70 and hsp110 are approximately similar in vaccine efficiency, they may bind differing subsets of peptides, i.e. hsp110 may carry antigenic epitopes that do not readily bind to hsc70, i.e. they may exhibit differing vaccine potential if not differing (mass) efficiencies. A similar argument can be made for grp170. The significant differences in molar efficiencies of these stress proteins may result from differing peptide binding affinities, differing properties of peptides bound to each stress protein family, or differing affinities of antigen presenting cells to interact with each of these four stress protein groups. Also noteworthy is that grp170, the most efficient vaccine in this group, is the only glycoprotein of the group.

Example 7

Interaction of hsp110 with hsp25 and hsp70

This example demonstrates the native interactions of hsp110, which protein was found to reside in a large molecular complex. Immunoblot analysis and co-immunoprecipitation studies identified two other heat shock proteins as components of this complex, hsp70 and hsp25. When examined in vitro, purified hsp25, hsp70 and hsp110 were observed to spontaneously form a large complex and to directly interact with one another. When luciferase was added to this in vitro system, it was observed to migrate into this chaperone complex following heat shock. Examination of two deletion mutants of hsp110 demonstrated that its peptide-binding domain is required for interaction with hsp25, but not with hsp70. The potential function of the hsp110-hsp70-hsp25 complex is discussed.

Materials & Methods
Reagents

The rabbit anti-hsp110 antibody has been characterized by Lee-Yoon, D. et al., 1995, J. Biol. Chem. 270, 15725-15733. Affinity purified mouse anti-hsc70 monoclonal antibody, rabbit anti-murine hsp25 antibody, rat anti-hsp90 antibody and rat anti-TCP-1a monoclonal antibody, as well as recombinant hsc70 and murine hsp25 were all obtained from StressGen Biotechnological Corp (Victoria, Canada). Anti-His Antibody was purchased from Amersham. Colon 26 tumor cells were cultured in DMEM supplemented with 10% calf serum in 5% $CO_2$ incubator.

Plasmid Construction and Expression

Purification of recombinant His-tagged hsp110 and two deletion mutants used here have been described by Oh, H. J. et al., 1997, J. Biol. Chem. 272, 31696-31640; and Oh, H. J. et al., 1999, J. Biol. Chem. 274, 15712-15718. Briefly, for the construction of hsp110 mutants, primers 5'-GCTAGAG-GATCCTGTGCATTGCAGTGTGCAATT (SEQ ID NO: 1) -/-CAGCGCAAGCTTACTAGTCCAGGTCCATATTGA-3' (SEQ ID NO: 2) (Mutant #1, a.a. 375-858) and 5'-GAC-GACGGATCCTCTGTCGAGGCAGACATGGA (SEQ ID NO: 3) -/-CAGCGCAAGCTTACTAGTCCAGGTC-CATATTGA-3' (SEQ ID NO: 4) (mutant #2, a.a. 508-858) were used in the polymerase chain reaction. The PCR products were cloned into pRSETA vector (Invitrogen), and a $His_6$-(enterokinase recognition sequence) and additional Asp-Arg-Trp-Gly-Ser (for mutant #1) or Asp-Arg-Trp (for mutant #2) were added to the N-terminal of hsp110 mutants. Plasmids were transformed into *E. coli* strain JM109 (DE3) and expression products were purified by Ni2-nitrilotriacetic acid-agarose column (QIAGEN, Inc.). The protein concentration was measured using the Bio-Rad protein assay kit.

Purification of Native hsp110

Cells were washed with phosphate-buffered saline and homogenized with a Teflon homogenizer with 5 volumes of buffer (30 mM $NaHCO_3$, pH 7.5, 1 mM phenylmethylsulfonyl fluoride). The homogenates were centrifuged for 20 min at 12,000×g, supernatant were further centrifuged for 2 h at 100,000×g. Cell extracts were first applied to Con A-sepharose column, unbound proteins were collected and loaded on ion exchange column (Mono Q, Pharmacia) equilibrated with 20 mM Tris-HCl, pH 7.5, 200 mM NaCl, 0.1 mM dithiothreitol. Bound proteins were eluted with a linear salt gradient (200mM~350mM NaCl). Hsp110 pooled fractions were concentrated using centricon 30 (Amicon) and applied to size exclusion column (superose 6, Pharmacia) for high performance chromatography (HPLC) equilibrated with 20 mM Tris-HCl, pH8.0, 150 mM NaCl, 1 mM DTT), then eluted with at a flow rate of 0.2 ml/min. Thyroglobulin (669 kDa), ferritin (440 kDa), catalase (158 kDa), albumin (67 kDa) and ovalbumin (43 kDa) were used as protein markers.

Western Blot Analysis

Cells were washed with PBS and lysed in 50 mM Tris.HCl, pH 7.5, 150 mM NaCl, 2 mM EDTA, 1% Triton X-100 and protease inhibitors. After incubation on ice for 30 min, cell extracts were boiled with equal volume of SDS sample buffer (50 mM Tris-HCl, pH 6.8, 5% β-mercaptoethanol, 2% SDS, 10% glycerol) for 10 min and centrifuged at 10,000 g for 20 min. Equivalent protein samples were subjected to 7.5-10% SDS-PAGE and electro-transferred onto immobilon-P membrane spore Ltd., Ulo). Membrane were blocked with 5% non-fat milk in TBST (20 mM Tris-HCl, pH 7.4, 137 mM NaCl, 0.05% Tween-20) for 1 h at room temperature, and then incubated for 2 h with primary antibodies diluted 1:1000 in TBST. After washing, membranes were incubated with horseradish peroxidase-conjugated goat anti-rabbit IgG or goat anti-mouse IgG diluted 1:2,000 in TBST. Immunoreactivity was detected using the Enhanced Chemiluminescence detection system (Amersham, Arlington Heights, Ill.).

Immunoprecipitation

Cells were washed 3 times with cold PBS and lysed in Buffer (10 mM Tris-HCl, pH 7.4, 150 mM NaCl, 2 mM EDTA, 0.5% Sodium Deoxycholate, 0.1% SDS, 1% NP40, 10 µg/ml leupeptin, 25 µg/ml aprotilin, 1 mM ABESF, 0.025% NaN3). The lysates were centrifuged and supernatant was presorbed with 0.05 volume preimmune serum together with 30 ml protein A beads for 1h. The lysates were incubated overnight at 4° C. with hsp110 antibody (1:100) or hsc70 antibody (1:200) or hsp25 antibody (1:100). For in vitro analysis of interaction within chaperones, recombinant wild-type hsp110 and hsp110 mutants first were incubated with hsc70 or hsp25 at 30° C. Then hsc70 antibody or hsp25 antibody were added and further incubated overnight at 4° C. Immune complex were precipitated with Protein A-agarose (30 µl) for 2h. Precipitates were washed 3 times with 50 mM Tris.HCl, pH 7.5, 150 mM NaCl, 0.1% SDS, 0.5% sodium deoxycholate, 1% NP40, 30-40 µl SDS sample buffer was added and boiled for 5 min. Supernatant were loaded to 7.5-12% SDS-PAGE and analyzed by immunoblotting.

Interaction Between Luciferase and HSPs

Luciferase (Boehringer Mannheim) was incubated with hsp110, hsc70 and hsp25 (150 nM each) in 25 mM Hepes, pH 7.9, 5 mM magnesium acetate, 50 mM KCl, 5 mM b-mercaptoethanol, and 1 mM ATP at room temperature or 43° C. for 30 min. The solution was centrifuged at 16,000 g for 20 min, the supernatant was loaded on the Sephacryl S-300 column (Pharmacia) equilibrated with 20 mM Tris.HCl, pH 7.8, 150 mM NaCl and 2 mM DTT. The protein was eluted at the flow rate of 0.24 ml/min at 4° C. Fractions were collected and analyzed by western blotting.

Results

Existence of hsp110 as a Large Complex Containing hsc70 and hsp25.

Characterization of native hsp110 in Colon26 cells was performed to investigate the physiological role of hsp110. After cell extracts were applied to successive chromatography on Con-A sepharose and Mono Q columns, partially purified hsp110 fraction was loaded onto the Superose 6 size exclusion column (maximum resolution of 5,000 kDa). It was observed that the ConA and ion exchange purified hsp110 fraction eluted from the Superose column in those fractions of size range between 200 to 700 kDa (FIG. 9A). Work was repeated using sephacryl 300 (allyl dextran/bisacrylamide matrix) column and analysis provided similar data.

Since hsp110 was eluted as one broad peak of high molecular mass, it is reasonable that this large in situ hsp110 complex might also contain additional components, potentially including other molecular chaperones and/or cellular substrates that may interact with hsp110. To investigate this possibility, the purified hsp110 fraction derived from both ion exchange and size exclusion columns was examined by immunoblotting for other HSPs using available antibodies. As shown in FIG. 9B, antibodies for hsp90, hsc70, T-complex polypeptide1 (TCP-1) and hsp25 were used. All four proteins were readily detectable in the total cell lysate (lanes 1, 3, 5, and 7). When the hsp110 fraction was examined, TCP-1 and hsp90 were not observed (lane 2 and 6). However, both hsc70 and hsp25 were found to co-purify with hsp110 with a significantly greater fraction of total cellular hsc70 present than of hsp25. Chromatography profile of hsc70 and hsp25 from size exclusion column also showed the similar pattern as that of hsp110 (FIG. 9A).

Figures 10A, 10B, 10C:
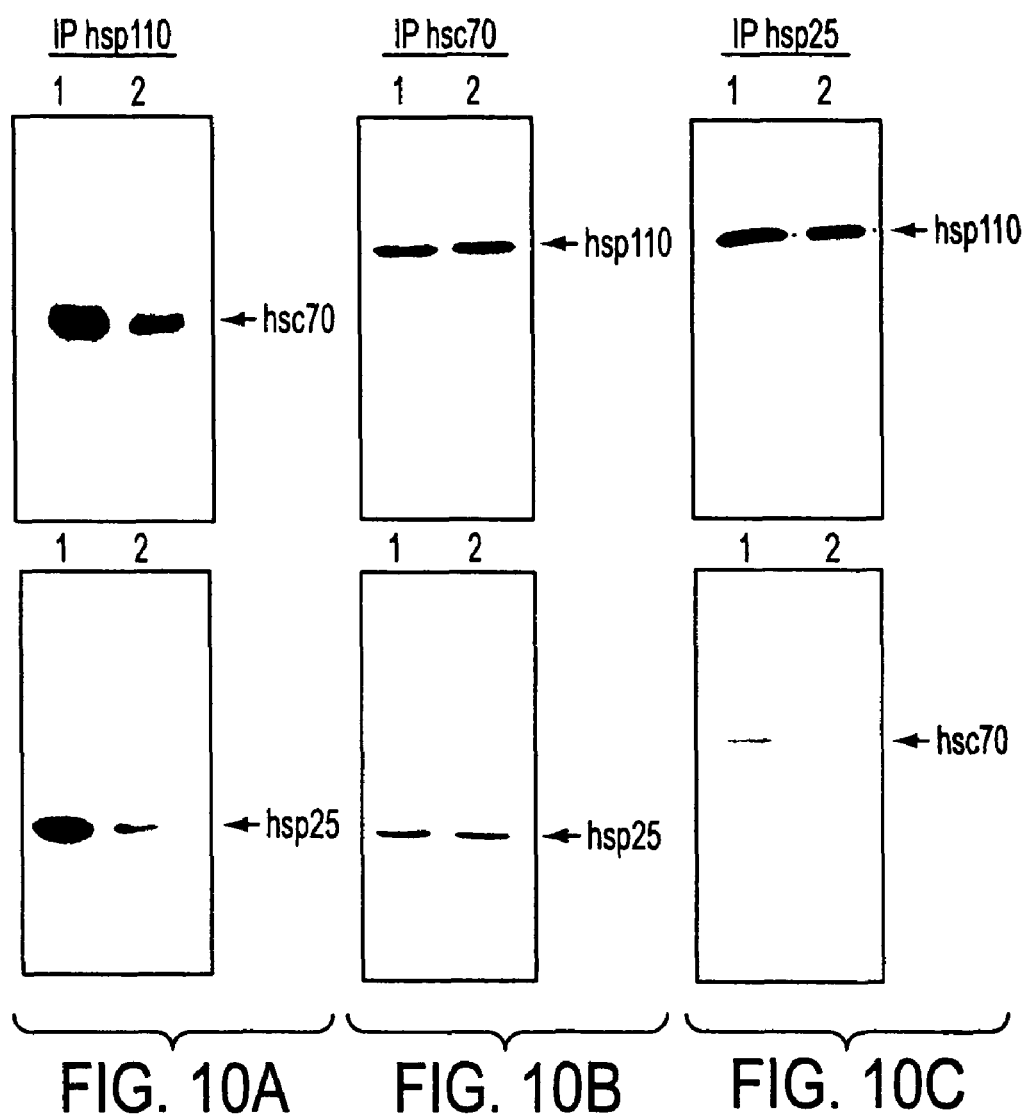
FIGS. 10A-C are immunoblots showing reciprocal immunoprecipitation between hsp110 and hsp70, hsp25. Following incubation with the indicated antibodies, protein A-sepharose was added and further incubated at 4° C. overnight, immunoprecipitates were examined by immunoblotting with hsp110, hsp70 and hsp25 antibodies. Total cell extracts was also used as a positive control (lane 1).

To determine whether this co-purification also reflected an interaction between these three molecular chaperones, a reciprocal co-immunoprecipitation analysis was conducted with Colon26 cell extracts and hsp110 fractions. Hsc70 and hsp25 were shown to precipitate with hsp110 using an anti-hsp110 antibody (FIG. 10A). Conversely, hsp110 was co-precipitated by an anti-hsc70 antibody or anti-hsp25 antibody (FIGS. 10B and 10C, top). Pre-immune serum was also used to perform immunoprecipitation as a negative control with a correspondingly negative outcome. Finally, interaction between hsc70 and hsp25 was analyzed by using antibodies for hsc70 and hsp25. Again, these two proteins were observed to co-immunoprecipitate with one (FIGS. 10B and 10C, bottom). From the above study, one can conclude that hsp110, hsc70 and hsp25 interact in situ, either directly or indirectly.

Analysis of Interaction of hsp110 with hsc70 and hsp25 in vitro.

To determine whether hsp110, hsc70 and hsp25 interact in vitro, and whether they are capable of forming a large molecular weight complex by using purified protein components, luciferase was added as a potential substrate to this mixture. It has been shown that hsp110 can solubilize this reporter protein following heat denaturation. Luciferase, with hsp110, hsc70 and hsp25 mix (at 1:1 molar ratio) were incubated at room temperature or at 43° C. for 30 minutes. The soluble fractions were loaded onto a Sephacryl S-300 column, eluted fractions were run on SDS-PAGE and analyzed by immunoblotting with antibodies for hsp110, hsc70, hsp25 and luciferase.

Figure 11A:
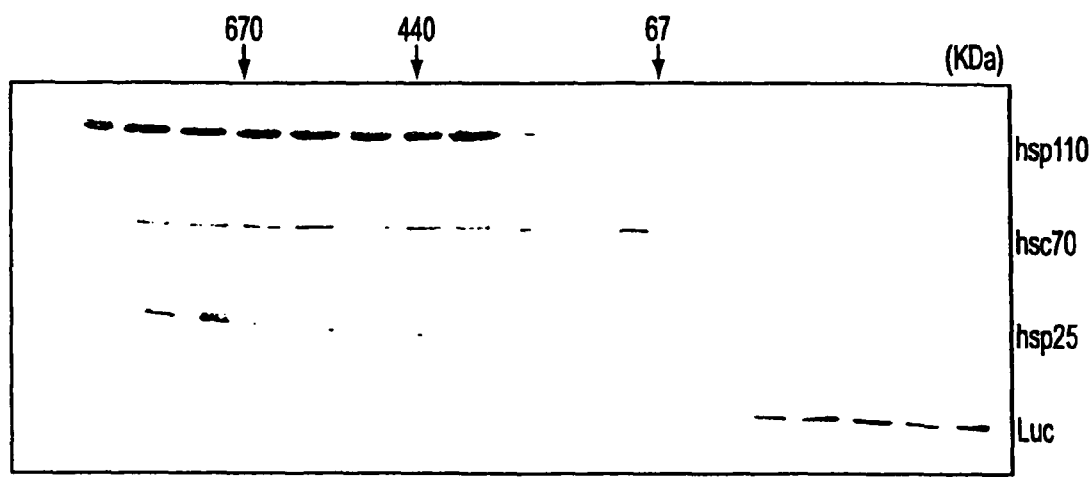
FIG. 11A shows immunoblots prepared when luciferase and Hsps were incubated at room temperature for 30 min, and soluble fraction after centrifugation at 16,000 g was loaded on Sephacryl S-300 column. The eluted fractions were analyzed by immunoblotting with antibodies for Hsps and luciferase.
Figure 11B:
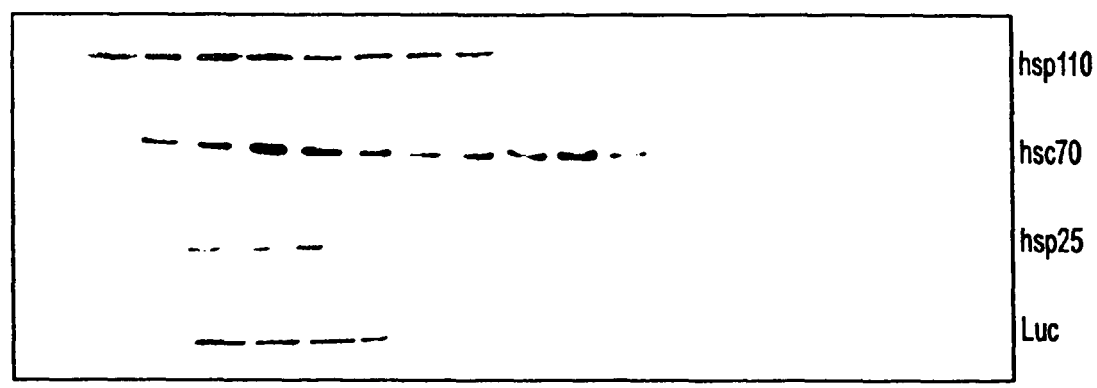
FIG. 11B shows immunoblots prepared when luciferase and Hsps were incubated at 43° C. for 30 min, and soluble fraction after centrifugation at 16,000 g was loaded on Sephacryl S-300 column. The eluted fractions were analyzed by immunoblotting with antibodies for Hsps and luciferase.

The results of this study are presented in FIGS. 11A and 11B. It was found that hsp110, hsc70 and hsp25 are again present in high molecule weight fractions, however these fractions were eluted at a significantly larger molecular size than that seen in vivo (FIG. 11A). Moreover, it was seen that heat treatment does not change elution pattern for hsp110, hsc70 or hsp25. However, luciferase, which does not co-elute with the hsp110 complex prior to heating (being present as a monomer), was observed to move into high molecule weight structure after the heat exposure (FIG. 11B). Almost all of the luciferase was sustained in a soluble form in these experiments. When heated alone, luciferase became rapidly insoluble. Heat shock did not affect the solubility of the three hsp110, hsc70 or hsp25.

Figure 12:
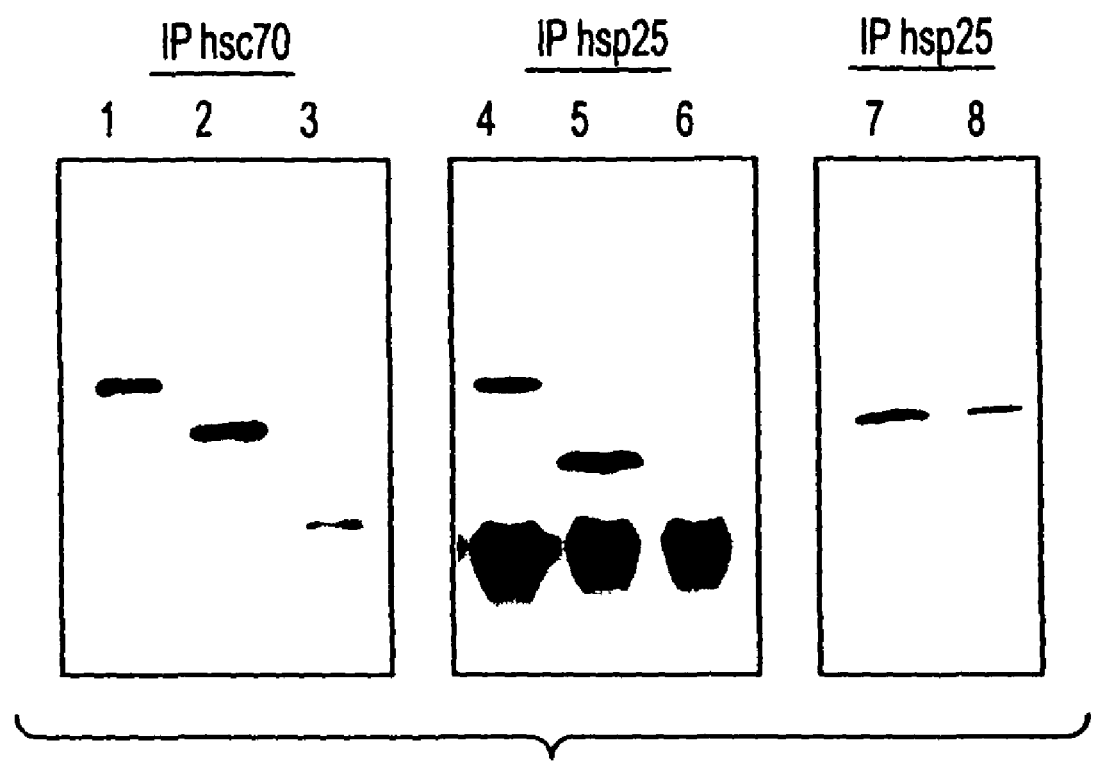
FIG. 12 shows the results of interaction analysis of hsp110 mutants and hsp70, hsp25 in vitro. E. coli expressed full-length hsp110 (lane 1, 4) and mutant #1 (lane 2, 5), mutant #2 (lane 3, 6) were incubated with hsc70 or hsp25 at 30° C. for 1 hour, then anti-hsc70 or anti-hsp25 antibodies were added. Immunoprecipitates were detected by anti-His antibody. In vitro interaction between hsc70 and hsp25 was also analyzed by the same method described above; hsc70 antibodies were used to test immunoprecipitate (lane 8). Total cell lysate was used as a positive control (lane 7). Equal amount of protein (2 μg) for wild-type hsp110, hsp110 mutants, hsc70 and hsp25 were included in each assay.

The above data indicate that hsp110, hsc70, and hsp25 co-purify in a large molecular weight structure in vitro, as does luciferase (if present) after heating. This does not indicate how these proteins interact themselves or that any two of them interact at all. That heated luciferase remains soluble, however, is evidence for its interaction with at least one of the chaperones. To determine how these proteins interact, co-immunoprecipitation experiments were performed again using the pairs of purified proteins. Hsc70 and hsp110 were found to interact in the absence of hsp25 (FIG. 12, lane 1) and correspondingly hsp110 was observed to precipitate with hsp25 alone, in the absence of hsc70 (lane 4). Lastly, hsc70 and hsp25 also co-precipitate in the absence of hsp110 Vane 8).

Finally, this in vitro study defining the interactions between hsp110, hsc70 and hsp25 was extended by examining two deletion mutants of hsp 110 that have previously been shown to represent the most simplistic (i.e. functional and non-functional) forms of this chaperone (Oh, H-J. et al., 1999, J. Biol. Chem. 274, 15712-15718). The first mutant examined (#1) lacks the N-terminal ATP binding domain of hsp110, but contains the remaining sequence: i.e. the adjacent beta sheet peptide binding domain and other C-terminal sequences (size: 75 kDa and containing amino acids 375-858). This mutant has been shown to be fully functional in its ability to stabilize heat denatured luciferase in a folding competent state. The second mutant used here (#2), again lacked the ATP binding domain as well as the adjacent beta sheet (peptide binding) domain, but contained the remaining C terminal sequence (size: 62 kDa and containing amino acids 508-858). This mutant has recently been shown to be incapable of performing the chaperoning function of sustaining heat denatured luciferase in a soluble state.

Mutant #1 (no ATP binding domain) was observed to co-precipitate with both hsp70 (lane 2) and hsp25 (lane 5), indicating that these interactions do not involve its ATP binding domain. However, mutant #2 (lacking both the ATP region and the peptide-binding region of hsp110 ) was observed to only associate with hsp70 (lane 3). This indicates that hsp25 and hsp70 can interact with hsp110 at different sites and that the association of hsp110 with hsp25 requires the peptide-binding domain of hsp110.

Discussion

This example describes investigations into the native interactions of hsp110 in Colon26 cells. The results show that hsp110 co-purifies with both hsc70 and hsp25 and further, that the three proteins can be co-immunoprecipitated. To determine that the co-immunoprecipitation results can reflect direct interactions between these chaperones and to also define these interactions, in vitro studies using purified hsp110, hsc70 and hsp25 were undertaken. It was found that these three chaperones also spontaneously form a large molecular complex in vitro. Moreover, this complex forms in the absence of an added substrate, but substrate (luciferase) can be induced to migrate into the complex by a heat stress.

It is also shown that each pair of these proteins can interact directly, i.e. hsc70 with hsp110, hsc70 with hsp25, and hsp110 with hsp25. This, together with the co-precipitation data obtained from cell lysates, strongly argues that these interactions naturally occur in situ. Moreover, use of two deletion mutants of hsp110 demonstrate that its peptide-binding domain is required for hsp25 binding, but not for hsc70 binding, and that its ATP binding domain is not required for the interaction with either hsc70 or hsp25. This suggests that hsp110 binds to hsp25 through its peptide-binding domain. That hsc70-hsp110 binding occurs in the absence of the hsp110 peptide-binding domain suggests that hsc70 may be actively binding to hsp110 through its (i.e. hsc70's) peptide-binding domain, but does not exclude the possibility that the two proteins interact via the involvement of other C-terminal domains.

These interactions between hsp110 and hsc70 raise possibilities as to how these proteins may function cooperatively. Since the peptide-binding domain of hsc70 and hsp110 appears to represent the "business end" of these chaperones in performing chaperoning functions, one might expect that their peptide binding domains would be actively associated with substrate and not one another. This raises the possibility that this complex represents a chaperone "storage compartment" that awaits cellular requirements. However, the migration of heat denatured luciferase into this fraction following heat shock argues for an active chaperoning activity of the complex itself. It is possible that hsc70 may piggy-back hsp110 in a manner that allows transfer of substrate from hsp110 to hsc70 with subsequent folding in conjunction with DnaJ homologs and other chaperones.

Hsp110 has not yet been shown to have a folding function in conjunction with DnaJ co-chaperones, as is the case with hsc70 (Oh, H. J. et al., 1997, J. Biol. Chem. 272, 31696-31640; Oh, H. J. et al., 1999, J. Biol. Chem. 274, 15712-15718). However, hsp110 exhibits different ATP binding properties than do the hsp70s, and possible co-chaperones of hsp110 may be awaiting discovery. Previous in vitro studies have demonstrated that while sHSPs (e.g. hsp25) bind non-native protein, refolding still requires the presence of hsp70 (Lee, G. J. et al., 1997, EMBO J. 16, 659-671;Jakob, U. et al., 1993, J. Biol. Chem. 268, 7414-7421; Merck, K. B. et al., 1993, J. Biol. Chem. 268, 1046-1052; Kampinga, H. H et al., 1994, Biochem. Biophys. Res. Commun. 204, 170-1177; Ehrnsperger, M. et al., 1997, EMBO J. 16, 221-229). Hsp110 and sHSPs may act in the differential binding of a broad variety of substrates for subsequent shuttling to hsp70-DnaJ containing chaperone machines.

That these three chaperones interact may represent a general phenomenon. Plesofsky-Vig and Brambl have recently shown that the small HSP of *Neurospora crassa*, called hsp30, binds to two cellular proteins, hsp70 and hsp88. Cloning and analysis of hsp88 has shown that it represents the hsp110 of *Neurospora crassa* (Plesofsky-Vig, N. and Brambl, R., 1998, J. Biol. Chem. 273, 11335-11341), suggesting that the interactions described here are phylogenetically conserved. In addition, Hatayama has described an interaction between hsp110 (referred to as hsp105) and hsp70 in FM3A cells (Hatayama, T et al., 1998, Biochem. Biophys. Res. Comm. 248, 394-401). The size of the hsp110 complex and the interaction with hsc70 observed in the present example (which also employed the added step of ion exchange chromatography) are clearly similar to, and in excellent agreement with this recent report. Finally, hsp90 and TCP-1 were not observed in the hsp110 complex in the present study, despite its previously identified association with hsc70 and other proteins in the steroid hormone receptor. However, it has recently been shown that SSE1 encoding a yeast member of the hsp110 family is required for the function of glucocorticoid receptor and physically associates with the hsp90 (Liu, X. D. et al., 1999, J. Biol. Chem. 274, 26654-26660).

The data presented in this example suggest that this complex offers an enhanced capacity to hold a greater variety of substrate proteins in a folding competent state and/or to do so more efficiently. The results further suggest that there may be an enhanced ability gained to refold denatured proteins in the presence of additional chaperones.

Example 8

In Vitro Formation and Stability of Stress Polypeptide Complexes

This example demonstrates that complexes of stress polypeptides with immunogenic polypeptides can be generated in vitro and that such complexes remain stable following freezing and thawing. Moreover, hsp110 and grp170 are both capable of forming complexes with different peptides that include antigens associated with both cancer and infectious disease.

Figure 13:
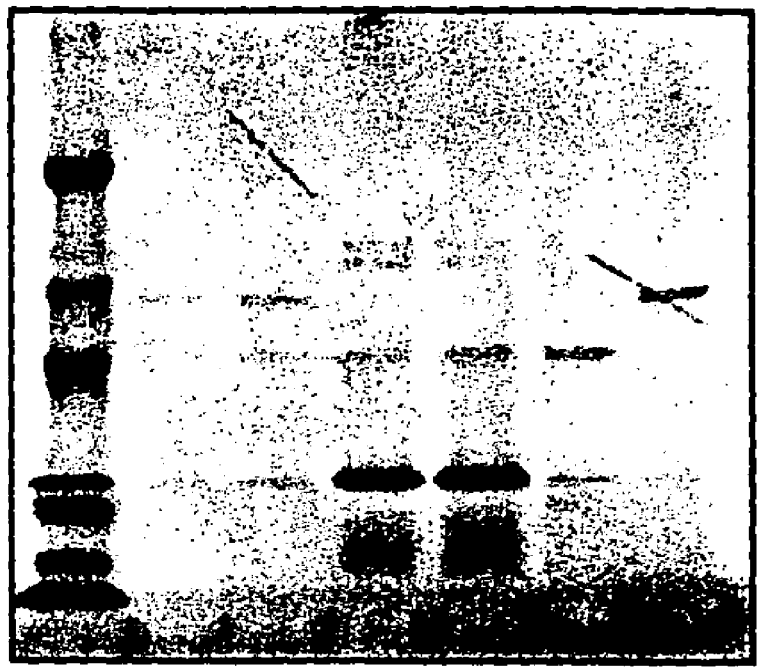
FIG. 13 shows the results of immunoprecipitation of her2/neu intracellular domain (ICD) with anti-hsp110 and anti-grp170 antibodies after formation of binding complexes in vitro. Lane 1 is a protein standard from 205 kDa to 7.4 kDa; lane 2 is hsp110+anti-hsp110 antibody; lane 3 is hsp110+ICD; lane 4 is grp170+ICD (in binding buffer); lane 5 is grp170+ICD (in PBS); lane 6 is ICD; and lane 7 is hsp110.

FIG. 13 shows the results of immunoprecipitation of her-2/neu intracellular domain (ICD) with anti-hsp110 and anti-grp170 antibodies after formation of binding complexes in vitro. Lane 1 is a protein standard from 205 kDa to 7.4 kDa; lane 2 is hsp110+anti-hsp110 antibody; lane 3 is hsp110+ICD; lane 4 is grp170+ICD (in binding buffer); lane 5 is grp170+ICD (in PBS); lane 6 is ICD; and lane 7 is hsp110.

Figure 14:
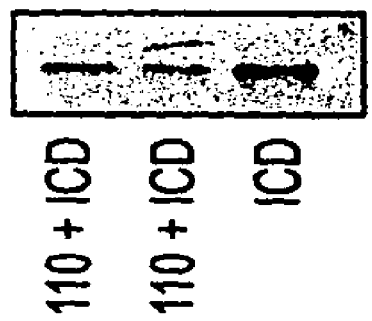
FIG. 14 is a western blot showing hsp110-ICD complex in both fresh (left lane) and freeze-thaw (center lane) samples, after immunoprecipitation of the complexes with anti-hsp110 antibody. The right lane is ICD.

FIG. 14 is a western blot showing hsp110-ICD complex in both fresh (eft lane) and freeze-thaw (center lane) samples, after immunoprecipitation of the complexes with anti-hsp110 antibody. The right lane is ICD. These results show that hsp110-ICD complexes are stable after freezing and thawing.

Figure 15:
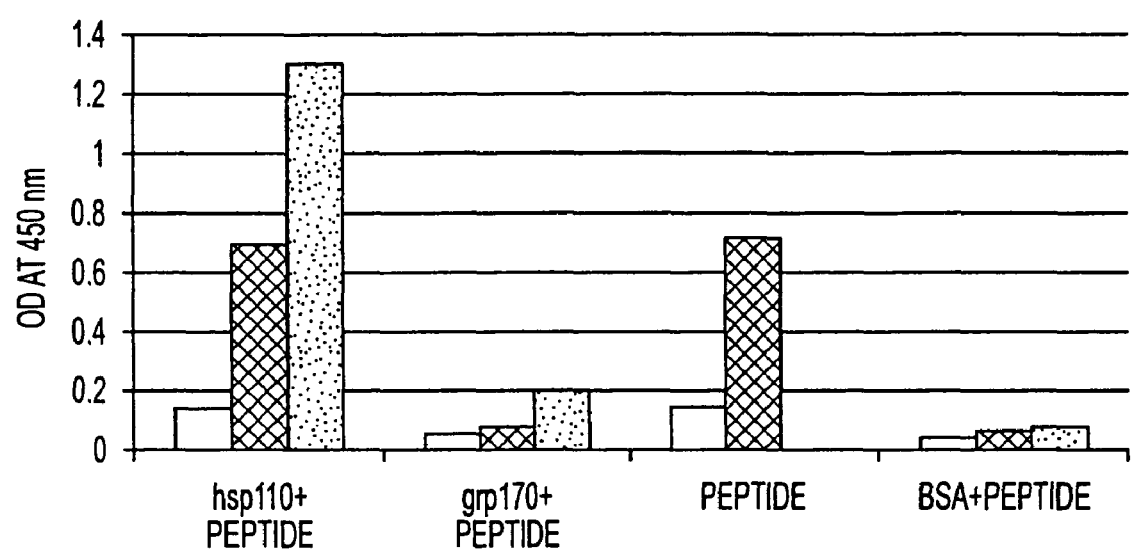
FIG. 15 is a bar graph showing hsp-peptide binding using a modified ELISA and p546, a 10-mer peptide of her-2/neu, selected for its HLA-A2 binding affinity and predicted binding to hsp110. The peptide was biotinylated and mixed with hsp110 in vitro. Purified mixture concentrations were 1 μg/ml (white bars), 10 μg/ml (cross-hatched bars), and 100 μg/ml (dark stippled bars).

FIG. 15 is a bar graph showing hsp-peptide binding using a modified ELISA and p546, a 10-mer peptide (VLQGLPREYV; SEQ ID NO: 5) of a her-2/neu transmembrane domain, selected for its HLA-A2 binding affinity and predicted binding to hsp110. The peptide was biotinylated and mixed with hsp110 in vitro (60 µg peptide and 60 µg hsp110 in 150 µl PBS). The mixtures were incubated at 43° C. for 30 minutes and then at 37° C. for 1 hour. The mixtures were purified using a Centricon-10 centrifuge to remove the unbound peptide. BSA (1%) was also incubated with 100 µg of the biotinylated peptide at the same conditions, and purified. Wells were coated with different concentrations of the purified mixtures, biotinylated peptide (positive control), or BSA (negative control) in a coating buffer. After incubation at 4° C. overnight, wells were washed 3 times with PBS-Tween 20 (0.05%) and blocked with 1% BSA in PBS for 1 hour at room temperature. After washing, 1:1000 streptavidin-HRP was added into the wells and plates were incubated at room temperature for 1 hour. The color was developed by adding the TMB substrate and reading the absorbance at 450 nm. Purified mixture concentrations were 1 µg/ml (white bars), 10 µg/ml (cross-hatched bars), and 100 µg/ml (dark stippled bars).

Figure 16:
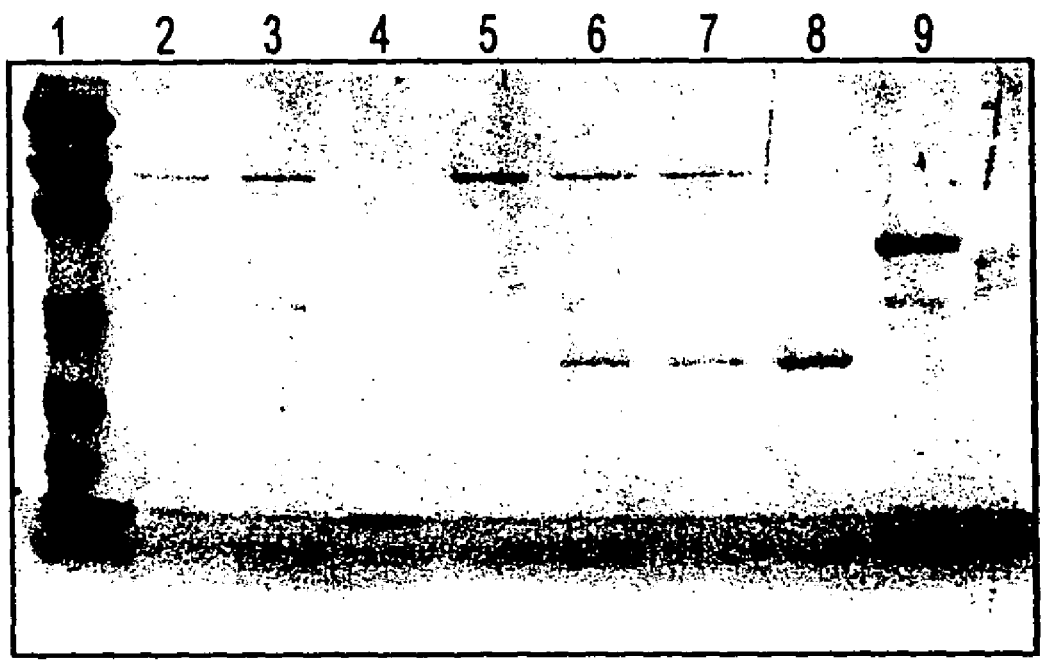
FIG. 16 shows the results of immunoprecipitation of M. tuberculosis antigens Mtb8.4 and Mtb39 with anti-hsp110 antibody after formation of binding complexes in vitro, using both fresh samples and samples that had been subjected to freezing and thawing. Lane 1 is a protein standard from 205 kDa to 7.4 kDa; lane 2 is hsp110+Mtb8.4; lane 3 is hsp110+Mtb8.4 (after freeze-thaw); lane 4 is Mtb8.4; lane 5 is hsp110; lane 6 is hsp110+Mtb39; lane 7 is hsp110+Mtb39 (after freeze-thaw); lane 8 is Mtb39; and lane 9 is anti-hsp110 antibody.

FIG. 16 shows the results of immunoprecipitation of *M. tuberculosis* antigens Mtb8.4 and Mtb39 with anti-hsp110 antibody after formation of binding complexes in vitro, using both fresh samples and samples that had been subjected to freezing and thawing. Lane 1 is a protein standard from 205 kDa to 7.4 kDa; lane 2 is hsp110+Mtb8.4; lane 3 is hsp110+Mtb8.4 (after freeze-thaw); lane 4 is Mtb8.4; lane 5 is hsp110; lane 6 is hsp110+Mtb39; lane 7 is hsp110+Mtb39 (after freeze-thaw); lane 8 is Mtb39; and lane 9 is anti-hsp110 antibody.

Example 9

Stress Polypeptide Complexes Elicit Cellular Immune Responses

This example demonstrates that hsp110 complexed with a peptide from her-2/neu, including the intracellular domain (ICD; amino acid residues 676-1255), extracellular domain (ECD; p369; KIFGSLAFL; SEQ ID NO: 6), or transmembrane region (p546) of her-2/neu, is immunogenic, as determined by gamma interferon (IFN-gamma) production by stimulated CTLs. The data show that hsp110 complexed with ICD generates a stronger CTL response than hsp110 complexed with the other peptides of her-2/neu.

Figure 17:
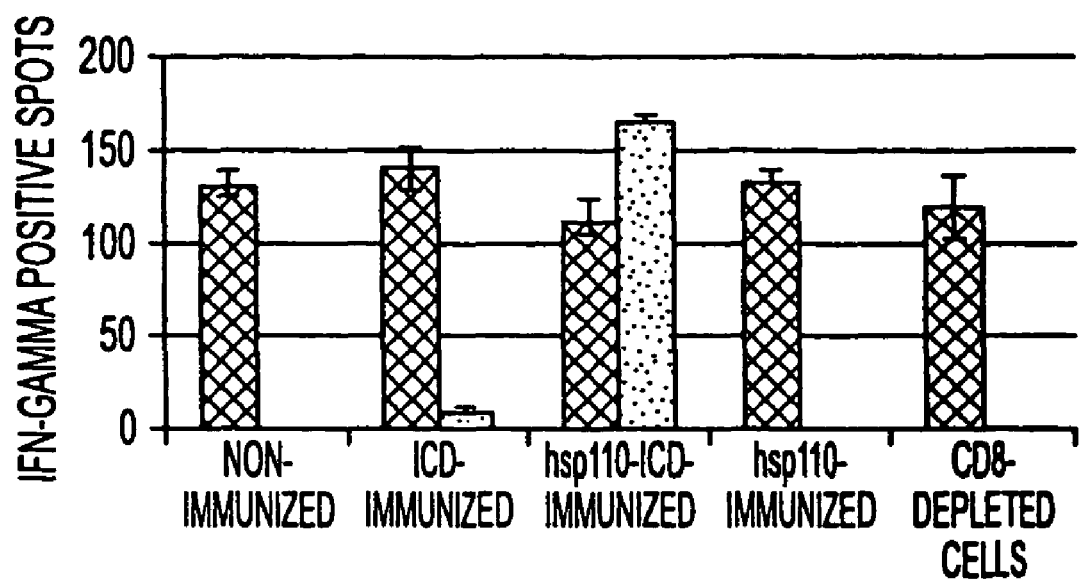
FIG. 17 is a bar graph showing gamma interferon (IFN-gamma) production (determined by number of spots in an ELISPOT assay) by T cells of A2/Kb transgenic mice (5 animals per group) after i.p. immunization with 25 μg of recombinant mouse hsp110-ICD complex. Total splenocytes or depleted cells ($5 \times 10^6$ cells/ml) were cultured in vitro with 25 µg/ml PHA (checkered bars) or 20 µg/ml ICD (dark stippled bars) overnight and IFN-gamma secretion was detected using the ELISPOT assay.

FIG. 17 is a bar graph showing IFN-gamma production (determined by number of spots in an ELISPOT assay) by T cells of A2/Kb transgenic mice (5 animals per group) after i.p. immunization with 25 µg of recombinant mouse hsp110-ICD complex. These mice are transgenic for a hybrid human/mouse class I molecule such that the animals are capable of HLA-A2 presentation, as well as retaining the murine poly-α3 domain, providing for additional cell surface protein interactions. Animals were boosted after 2 weeks, and sacrificed 2 weeks thereafter. Control groups were injected with 25 µg of ICD or hsp110, or not immunized. CD8 T cells were depleted using Dynabeads coated with anti-CD8 antibody and magnetic separation. Total splenocytes or depleted cells ($5 \times 10^6$ cells/ml) were cultured in vitro with 25 µg/ml PHA (checkered bars) or 20 µg/mi ICD (dark stippled bars) overnight and IFN-gamma secretion was detected using the ELISPOT assay.

Figure 18:
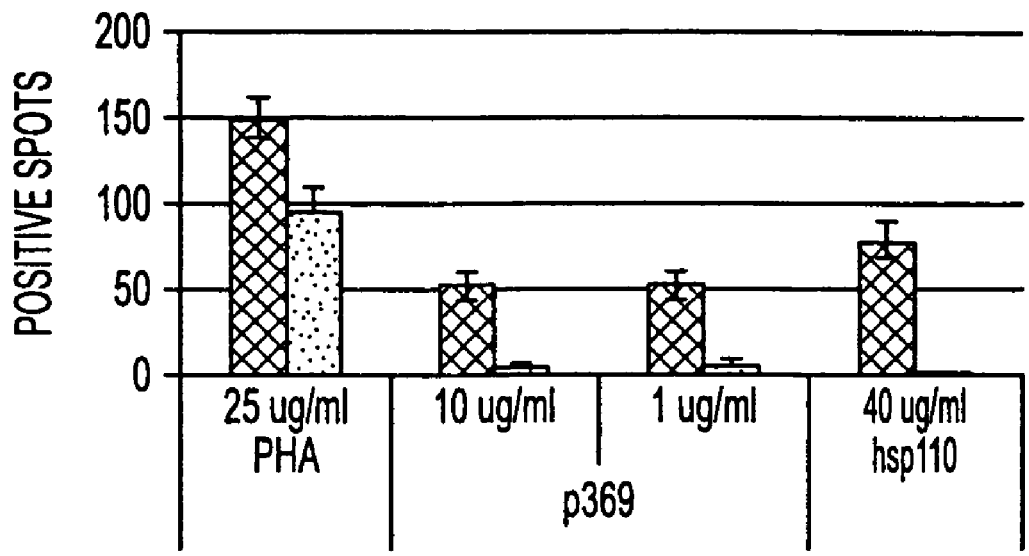
FIG. 18 is a bar graph showing immunogenicity of hsp110-peptide complexes reconstituted in vitro, as determined by number of positive spots in an ELISPOT assay for IFN-gamma secretion. Recombinant hamster hsp110 (100 µg) was incubated with 100 µg of the 9-mer her-2/neu peptide p369, an HLA-A2 binder. Eight-week old HLA-A2 transgenic mice (n=4) were immunized i.p. with either hsp110+peptide complex (group A, cross-hatched bars) or peptide alone (group B, dark stippled bars). Counts for the non-stimulated cells (negative controls) were <40 and were subtracted from the counts for stimulated cells.

FIG. 18 is a bar graph showing immunogenicity of hsp 110-peptide complexes reconstituted in vitro, as determined by number of positive spots in an ELISPOT assay for IFN-gamma secretion. Recombinant hamster hsp110 (100 µg) was incubated with 100 µg of the 9-mer her-2/neu peptide p369, an HLA-A2 binder, at 43° C. for 30 minutes, followed by incubation at room temperature for 60 minutes. The complex was purified using a Centricon-10 centrifuge to remove unbound peptides. Eight-week old HLA-A2 transgenic mice (n=4) were immunized i.p. with 60 µg of either hsp110+peptide complex (group A, cross-hatched bars) or peptide alone (group B, dark stippled bars) in 200 µl PBS and boosted 2 weeks later. Animals were sacrificed 2 weeks after the last injection and their splenocytes ($10^7$ cells/ml) were stimulated in vitro with PHA (positive control), immunizing peptide, or hsp110 when added with 15 U/mil of human recombinant IL-2. Counts for the non-stimulated cells (negative controls) were <40 and were subtracted from the counts for stimulated cells.

Figure 19:
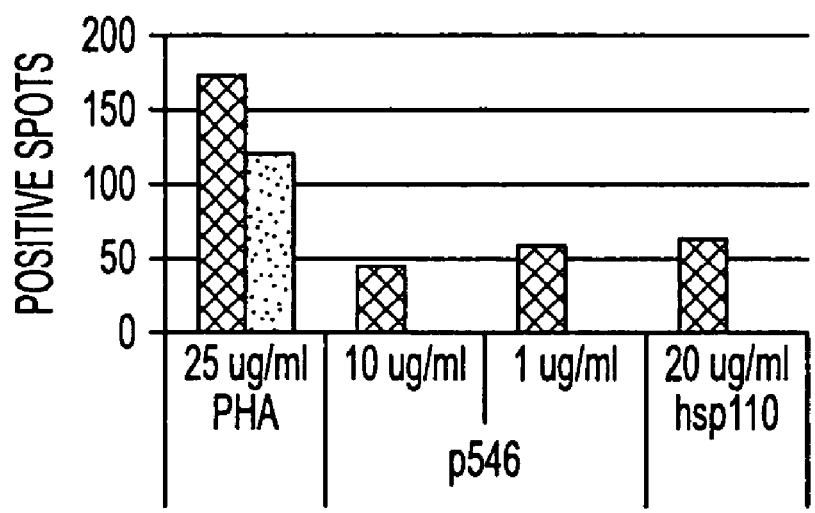
FIG. 19 is a bar graph showing immunogenicity of hsp110-peptide complexes reconstituted in vitro, as determined by number of positive spots in an ELISPOT assay for IFN-gamma secretion. Recombinant hamster hsp110 (100 µg) was incubated with 100 µg of the 10-mer her-2/neu peptide p546, an HLA-A2 binder. Eight-week old HLA-A2 transgenic mice (n=2) were immunized i.p. with either hsp110+peptide complex (group A, cross-hatched bars) or peptide alone (group B, dark stippled bars). Counts for the non-stimulated cells (negative controls) were <40 and were subtracted from the counts for stimulated cells.

FIG. 19 is a bar graph showing immunogenicity of hsp110-peptide complexes reconstituted in vitro, as determined by number of positive spots in an ELISPOT assay for IFN-gamma secretion. Recombinant hamster hsp110 (100 µg) was incubated with 100 µg of the 10-mer her-2/neu peptide p546, an HLA-A2 binder, at 43° C. for 30 minutes, followed by incubation at room temperature for 60 minutes. The complex was purified using a Centricon-10 centrifuge to remove unbound peptides. Eight-week old HLA-A2 transgenic mice (n=2) were immunized i.p. with 60 µg of either hsp110+peptide complex (group A, cross-hatched bars) or peptide alone (group B, dark stippled bars) in 200 µl PBS and boosted 2 weeks later. Animals were sacrificed 2 weeks after the last injection and their splenocytes ($10^7$ cells/ml) were stimulated in vitro with PHA (positive control), immunizing peptide, or hsp110 when added with 15 U/ml of human recombinant IL-2. Counts for the non-stimulated cells (negative controls) were <40 and were subtracted from the counts for stimulated cells.

Example 10

Stress Polypeptide Complexes Elicit Specific Antibody Responses

This example demonstrates that immunization with an hsp110-her2/neu ICD complex elicits antibody responses in A2/Kb transgenic mice. This response is specific, and the response is significantly greater than occurs with administration of her2/neu ICD alone. Thus, stress protein complexes of the invention are capable of stimulating both cellular and humoral immunity.

Figure 20:
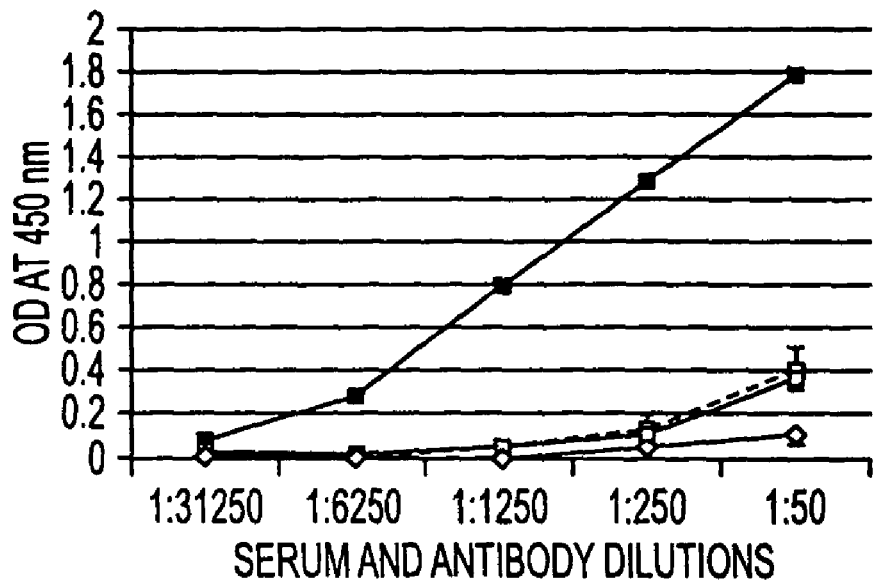
FIG. 20 is a graph showing specific anti-hsp110 antibody response in A2/Kb transgenic mice following i.p. immunization with the hsp110-ICD (her2/neu) complex. ELISA results are plotted as optical density (OD) at 450 nm as a function of serum and antibody dilutions. Results are shown for the positive control of anti-hsp110 (solid squares), the negative control of unrelated antibody (open circles), and serum at day 0 (closed circles), day 14 (open squares, dashed line), and day 28 (open squares, solid line). These results confirm that the mice did not develop an autoimmune response to hsp110.

FIG. 20 is a graph showing specific anti-hsp110 antibody response in A2/Kb transgenic mice following i.p. immunization with the hsp110-ICD (her2/neu) complex. ELISA results are plotted as optical density (OD) at 450 nm as a function of serum and antibody dilutions. Results are shown for the positive control of anti-hsp110 (solid squares), the negative control of unrelated antibody (open circles), and serum at day 0 (closed circles), day 14 (open squares, dashed line), and day 28 (open squares, solid line). These results confirm that the mice did not develop an autoimmune response to hsp110.

Figure 21:
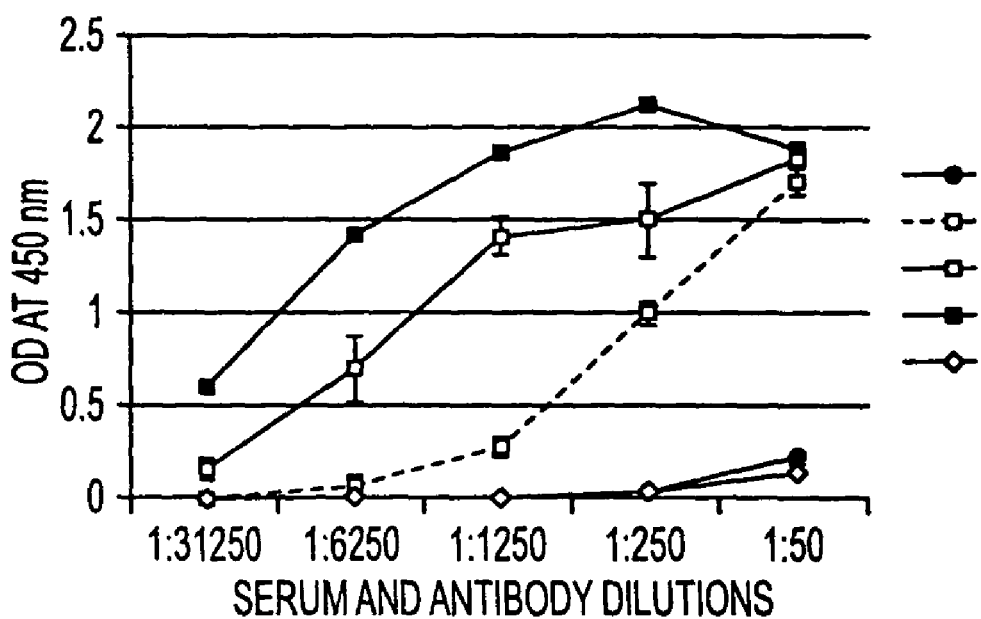
FIG. 21 is a graph showing specific anti-ICD antibody response in A2/Kb transgenic mice following i.p. immunization with the hsp110-ICD complex. ELISA results are plotted as optical density (OD) at 450 nm as a function of serum and antibody dilutions. Results are shown for the positive control of anti-ICD (solid squares), the negative control of unrelated antibody (open diamonds), and serum at day 0 (closed circles), day 14 (open squares, dashed line), and day 28 (open squares, solid line). These results confirm that the mice developed a specific antibody response to ICD of her2/neu after immunization with the stress protein complex.

FIG. 21 is a graph showing specific anti-ICD antibody response in A2/Kb transgenic mice following i.p. immunization with the hsp110-ICD complex. ELISA results are plotted as optical density (OD) at 450 nm as a function of serum and antibody dilutions. Results are shown for the positive control of anti-ICD (solid squares), the negative control of unrelated antibody (open diamonds), and serum at day 0 (closed circles), day 14 (open squares, dashed line), and day 28 (open squares, solid line). These results confirm that the mice developed a specific antibody response to ICD of her2/neu after immunization with the stress protein complex.

Figure 22:
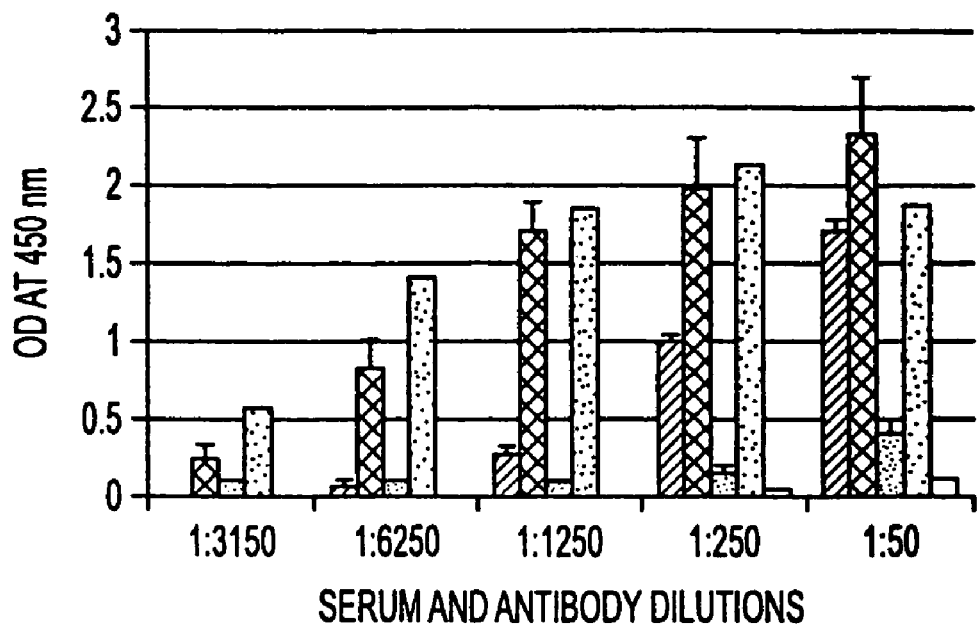
FIG. 22 is a bar graph comparing specific anti-ICD antibody responses in A2/Kb transgenic animals 2 weeks after priming with different vaccine formulas. Results are plotted as OD at 450 nm for the various serum and antibody dilutions and bars represent data for animals primed with hsp110-ICD (stippled bars), the positive control of ICD in complete Freund's adjuvant (checkered bars), ICD alone (cross-hatched bars), anti-ICD antibody (dark stippled bars), and the negative control of unrelated antibody (open bars).

FIG. 22 is a bar graph comparing specific anti-ICD antibody responses in A2/Kb transgenic animals 2 weeks after priming with different vaccine formulas. Results are plotted as OD at 450 nm for the various serum and antibody dilutions and bars represent data for animals primed with hsp110-ICD (stippled bars), the positive control of ICD in complete Freund's adjuvant (CFA; checkered bars), ICD alone (cross-hatched bars), anti-ICD antibody (dark stippled bars), and the negative control of unrelated antibody (open bars).

Figure 23:
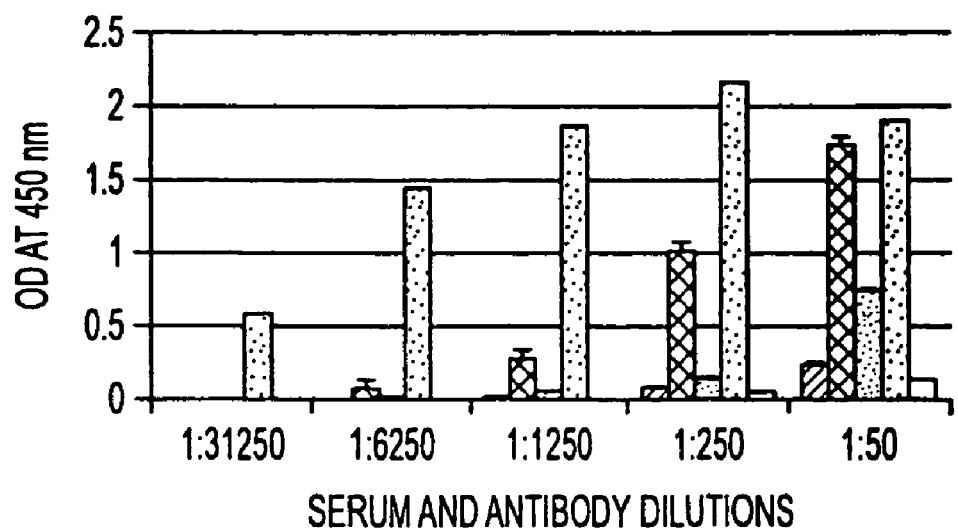
FIG. 23 is a bar graph comparing specific anti-ICD antibody generation 2 weeks after s.c. or i.p. priming of A2/Kb transgenic with hsp110-ICD complex. Results are plotted as OD at 450 nm for the various serum and antibody dilutions and bars represent serum at day 0 (stippled bars), serum i.p. at day 14 (checkered bars), serum s.c. at day 14 (cross-hatched bars), anti-ICD antibody (dark stippled bars), and the negative control of unrelated antibody (open bars).

FIG. 23 is a bar graph comparing specific anti-ICD antibody generation 2 weeks after s.c. or i.p. priming of A2/Kb transgenic with hsp110-ICD complex. Results are plotted as OD at 450 nm for the various serum and antibody dilutions and bars represent serum at day 0 (stippled bars), serum i.p. at day 14 (checkered bars), serum s.c. at day 14 (cross-hatched bars), anti-ICD antibody (dark stippled bars), and the negative control of unrelated antibody (open bars).

Example 11

Tumor Cells Transfected With an Hsp110 Vector Over-Express Hsp110

This example provides data characterizing colon 26 cells (CT26) transfected with a vector encoding hsp110 (CT26-hsp110 cells). These CT26-hsp110 cells overexpress hsp110, as demonstrated by both immunoblot and immunofluorescence staining.

Figure 24A:
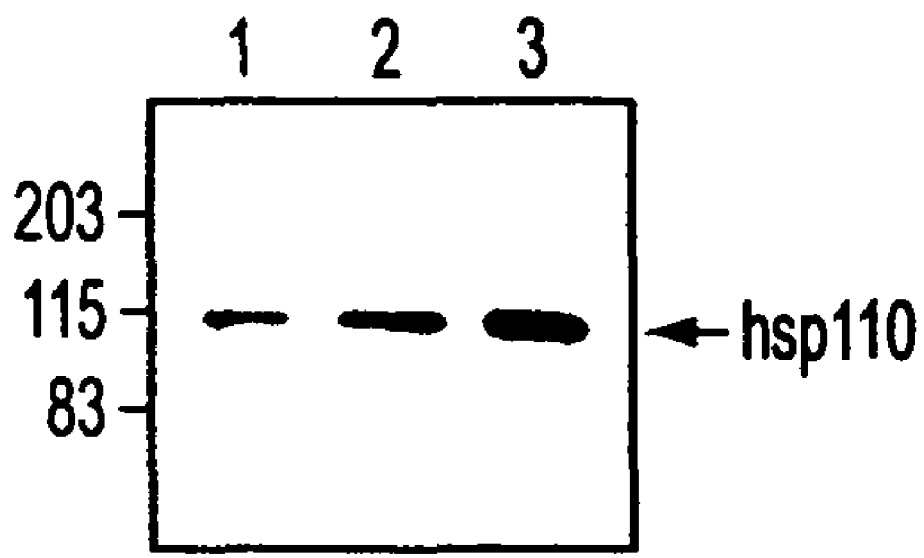
FIG. 24A is an immunoblot showing that colon 26 cells (CT26) transfected with a vector encoding hsp110 exhibit increased hsp110 expression relative to untransfected CT26 cells and CT26 cells transfected with an empty vector. Equivalent protein samples from CT26 (lane 1), CT26-vector Vane 2), and CT26-hsp110 (lane 3) were subjected to 10% SDS PAGE and transferred onto immobilon-P membrane. Membranes were probed with antibodies for hsp110. After washing, membranes were incubated with horseradish peroxidase-conjugated goat anti-rabbit IgG or goat anti-mouse IgG diluted 1:2,000 in TBST. Immunoreactivity was detected using the Enhanced Chemiluminescence detection system.

FIG. 24A is an immunoblot showing that CT26-hsp110 cells exhibit increased hsp110 expression relative to untransfected CT26 cells and CT26 cells transfected with an empty vector (CT26-vector). Equivalent protein samples from CT26 (lane 1), CT26-vector (lane 2), and CT26-hsp110 (lane 3) were subjected to 10% SDS PAGE and transferred onto immobilon-P membrane. Membranes were probed with antibodies for hsp110. After washing, membranes were incubated with horseradish peroxidase-conjugated goat anti-rabbit IgG or goat anti-mouse IgG diluted 1:2,000 in TBST. Immunoreactivity was detected using the Enhanced Chemiluminescence detection system.

Figure 24B:
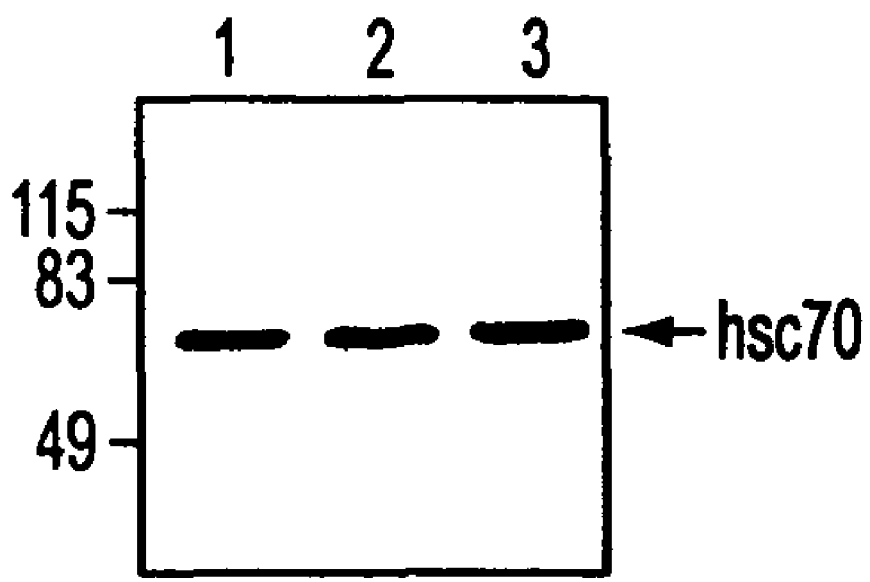
FIG. 24B shows that CT26-hsp110 cells do not exhibit enhanced hsc70 expression relative to untransfected CT26 cells or CT26 cells transfected with an empty vector. Equivalent protein samples from CT26 (lane 1), CT26-vector plane 2), and CT26-hsp110 (lane 3) were prepared as for FIG. 24A, except that membranes were probed with antibodies for hsc/hsp70.

FIG. 24B shows that CT26-hsp110 cells do not exhibit enhanced hsc70 expression relative to untransfected CT26 cells or CT26 cells transfected with an empty vector. Equivalent protein samples from CT26 (lane 1), CT26-vector (lane 2), and CT26-hsp110 (lane 3) were prepared as for FIG. 24A, except that membranes were probed with antibodies for hsc/hsp70.

Figure 25A:
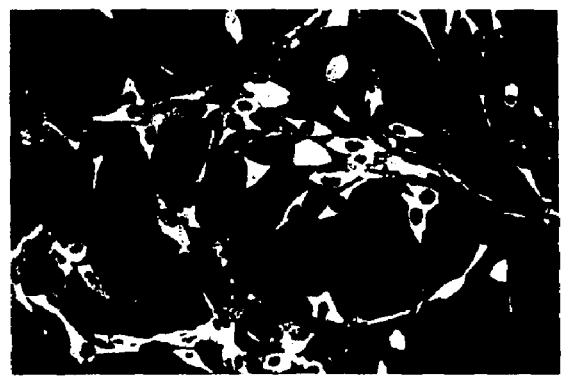
FIG. 25A is a photomicrograph showing immunofluorescence staining of hsp110 in CT26 cells. Cells were seeded on the cover slips one day before the staining. Cover slips were then incubated with rabbit anti-hsp110 antibody (1:500 dilution) followed by FITC-labeled dog anti-rabbit IgG staining. Normal rabbit IgG was used as negative control.

FIG. 25A is a photomicrograph showing immunofluorescence staining of hsp110 in CT26 cells. Cells were seeded on the cover slips one day before the staining. Cover slips were then incubated with rabbit anti-hsp110 antibody (1:500 dilution) followed by FITC-labeled dog anti-rabbit IgG staining. Normal rabbit IgG was used as negative control.

Figure 25B:
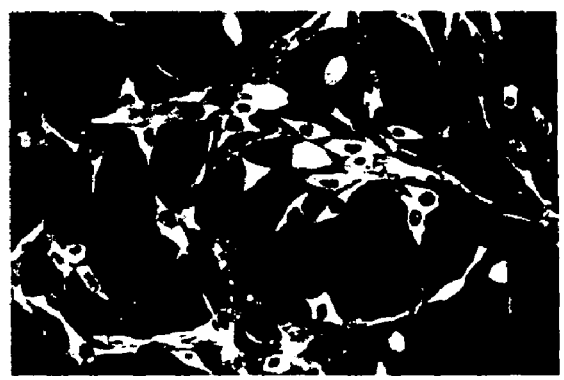
FIG. 25B is a photomicrograph showing immunofluorescence staining of hsp 110 in empty vector transfected CT26 cells. Cells were prepared and immunostained as in FIG. 25A.

FIG. 25B is a photomicrograph showing immunofluorescence staining of hsp 110 in empty vector transfected CT26 cells. Cells were prepared and immunostained as in FIG. 25A.

Figure 25C:
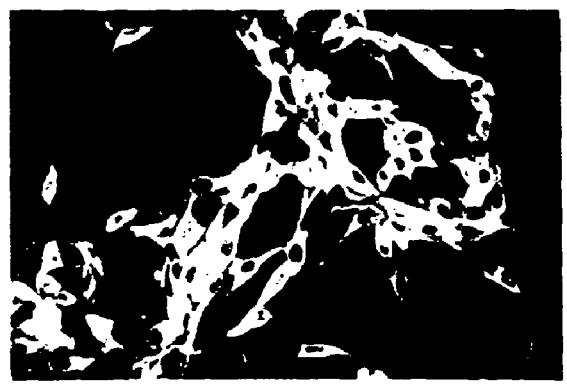
FIG. 25C is a photomicrograph showing immunofluorescence staining of hsp110 in hsp110 over-expressing cells. Cells were prepared and immunostained as in FIG. 25A.

FIG. 25C is a photomicrograph showing immunofluorescence staining of hsp110 in hsp110 over-expressing cells. Cells were prepared and immunostained as in FIG. 25A.

Example 12

Growth Properties of Tumor Cells Over-Expressing Hsp110

This example provides data characterizing the in vivo and in vitro growth properties of CT26-hsp110 cells.

Figure 26:
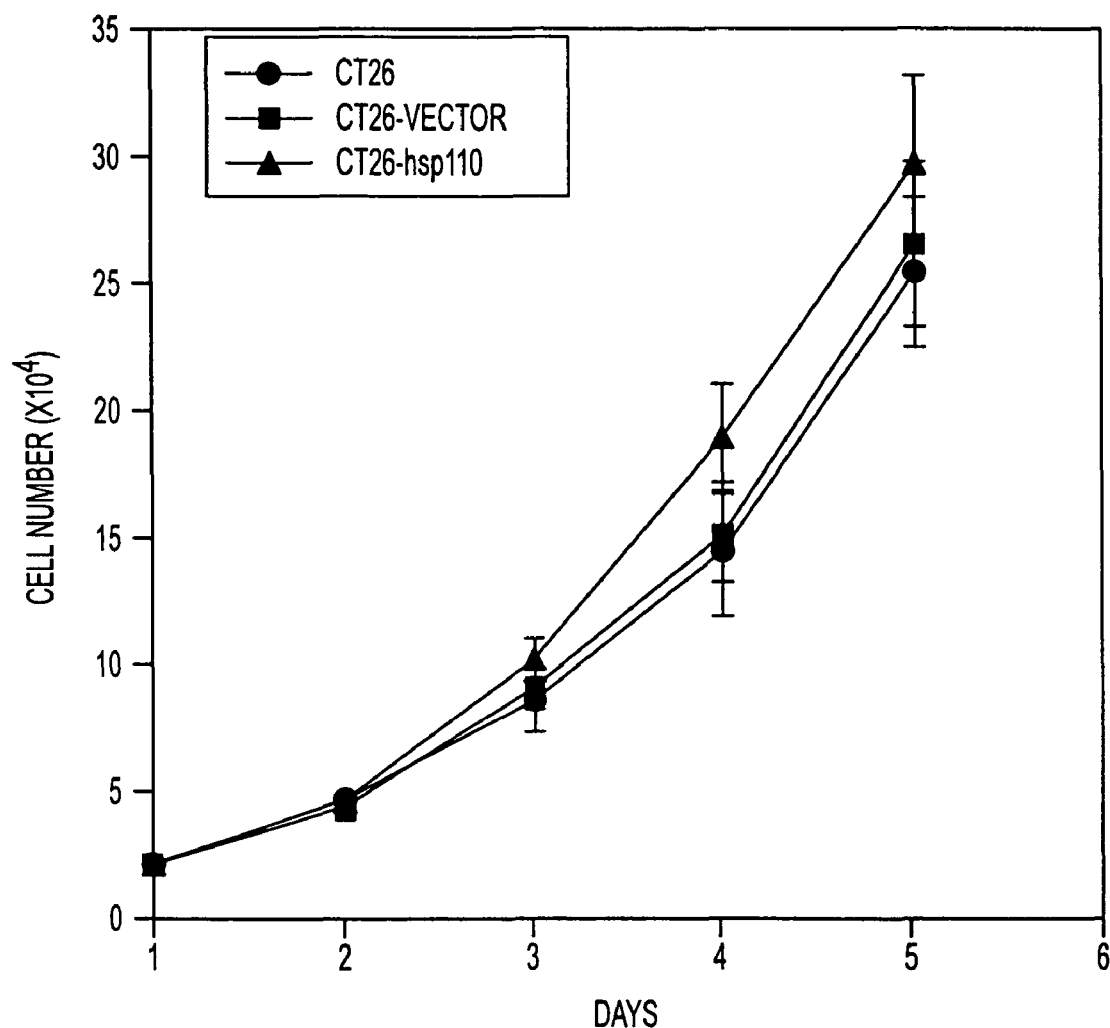
FIG. 26 is a graph demonstrating in vitro growth properties of wild type and hsp110-transfected cell lines, plotted as cell number at 1-5 days after seeding. Cells were seeded at a density of $2 \times 10^4$ cells per well. 24 hours later cells were counted (assigned as day 0). Cells from triplicate wells were counted on the indicated days. The results are means±SD of three independent experiments using wild type CT26 cells (circles), CT26 cells transfected with empty vector (squares), and hsp110-transfected CT26 cells (triangles).

FIG. 26 is a graph demonstrating in vitro growth properties of wild type and hsp110-transfected cell lines, plotted as cell number at 1-5 days after seeding. Cells were seeded at a density of $2 \times 10^4$ cells per well. 24 hours later cells were counted (assigned as day 0). Cells from triplicate wells were counted on the indicated days. The results are means±SD of three independent experiments using wild type CT26 cells (circles), CT26 cells transfected with empty vector (squares), and hsp110-transfected CT26 cells (triangles).

Figure 27:
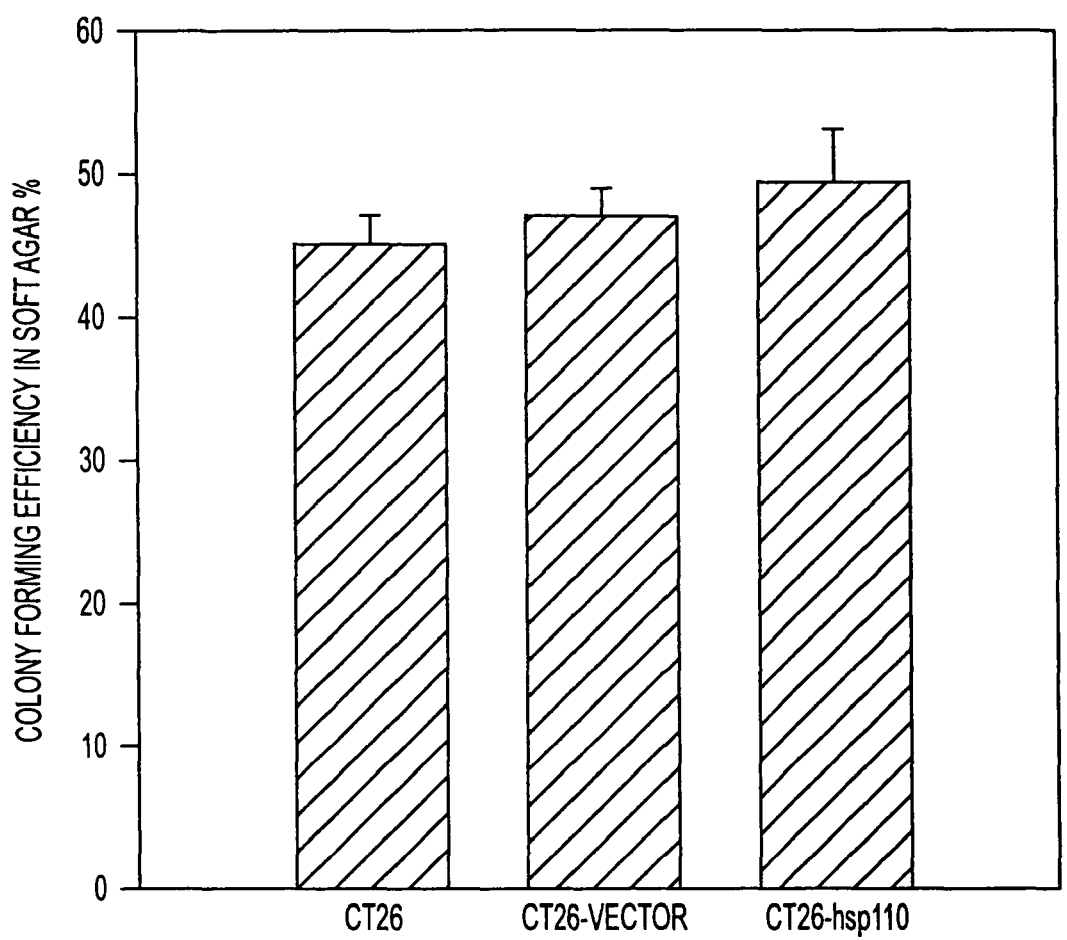
FIG. 27 is a bar graph showing the effect of hsp110 over-expression on colony forming ability in soft agar. Wild-type CT26 cells, empty vector transfected CT26-vector cells and hsp110 over-expressing CT26-hsp110 cells were plated in 0.3% agar and analyzed for their ability to form colonies ($\geq 0.2$) in soft agar. $P<0.05$, compared with CT26-vector, as assessed by student's t test.

FIG. 27 is a bar graph showing the effect of hsp110 over-expression on colony forming ability in soft agar. Wild-type CT26 cells, empty vector transfected CT26-vector cells and hsp110 over-expressing CT26-hsp110 cells were plated in 0.3% agar and analyzed for their ability to form colonies ($\geq 0.2$) in soft agar. P<0.05, compared with CT26-vector, as assessed by student's t test.

Figure 28:
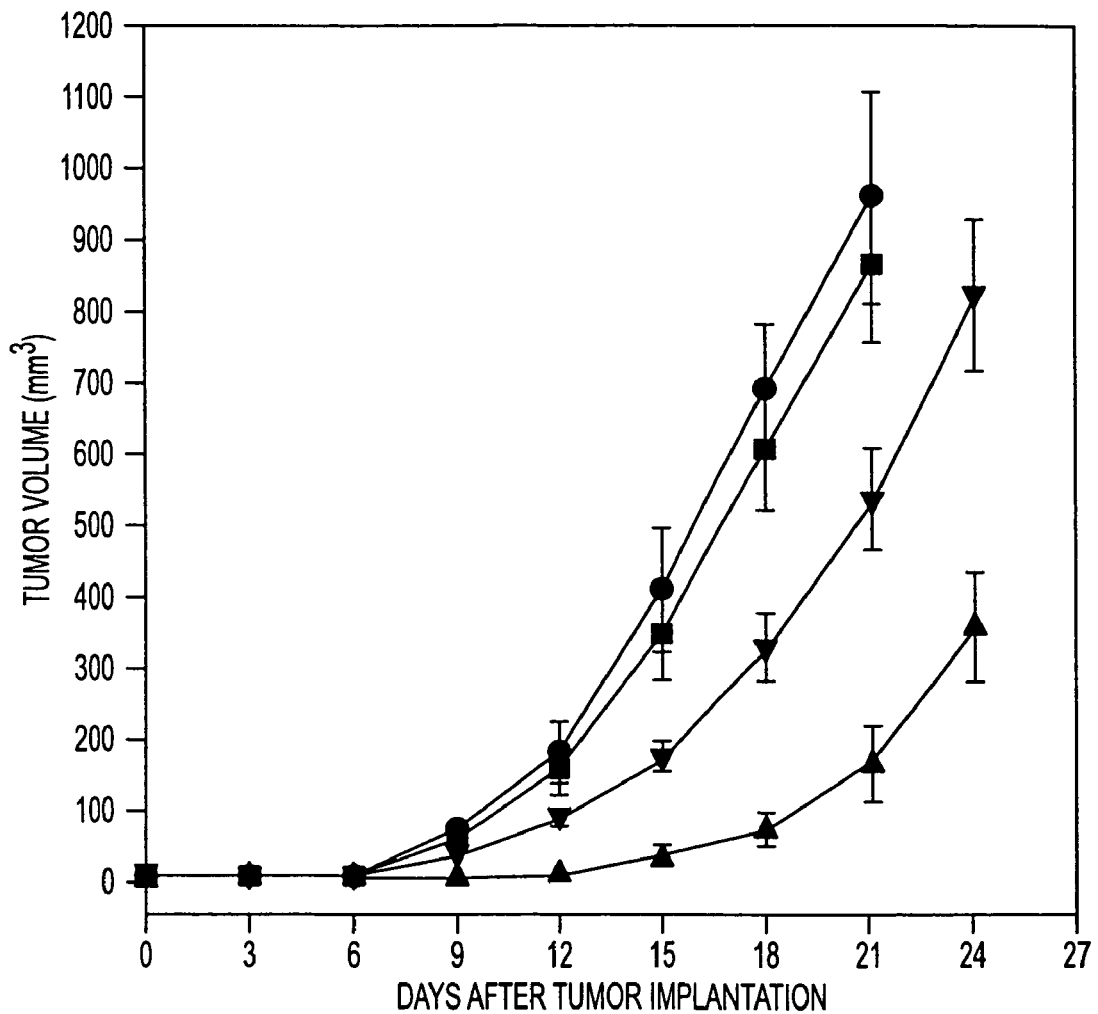
FIG. 28 is a graph showing in vivo growth properties of wild-type and hsp110 transfected CT26 cell line. $5 \times 10^4$ cells were inoculated s.c. into flank area of balb/c mice. Tumor growth was recorded twice a week measuring both the longitudinal and transverse diameter with a caliper. Tumor volume, in cubic mm, is plotted as a function of days after tumor implantation for CT26 wild type cells (circles), CT26 cells transfected with empty vector (squares), CT26 cells transfected with hsp110, $5 \times 10^4$ (upward triangles), and CT26 cells transfected with hsp110, $5 \times 10^5$ (downward triangles).

FIG. 28 is a graph showing in vivo growth properties of wild-type and hsp110 transfected CT26 cell line. $5 \times 10^4$ cells were inoculated s.c. into flank area of balb/c mice. Tumor growth was recorded twice a week measuring both the longitudinal and transverse diameter with a caliper. Tumor volume, in cubic mm, is plotted as a function of days after tumor implantation for CT26 wild type cells (circles), CT26 cells transfected with empty vector (squares), CT26 cells transfected with hsp110, $5 \times 10^4$ (upward triangles), and CT26 cells transfected with hsp110, $5 \times 10^5$ (downward triangles).

Example 13

Immunization With CT26-Hsp110 Cells Protects Against Tumor Challenge

This example demonstrates that mice immunized with irradiated hsp110 over-expressing CT26 cells are protected against subsequent challenge with live CT26 cells. In addition, immunization with CT26-hsp110 cells elicits tumor specific CTL and antibody responses.

Figure 29:
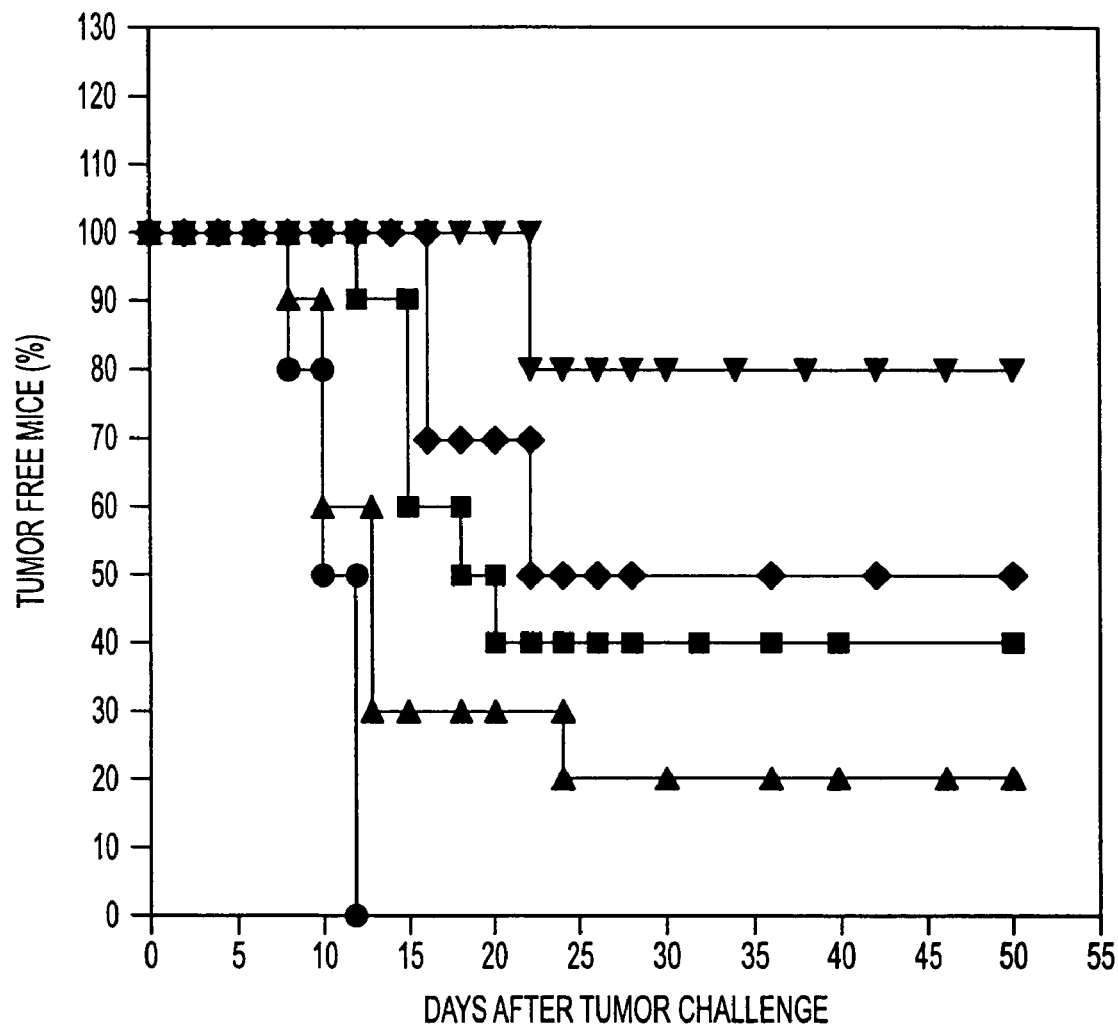
FIG. 29 is a plot showing the effect of injection with irradiated hsp110-overexpressing cells on the response to challenge with live CT26 cells. Mice were injected with $5 \times 10^5$ irradiated (9,000 rad) CT26-hsp110 cells subcutaneously in the left flank. Two weeks later, mice were challenged on the right flank with live CT26 cells. Growth of tumor in mice without preimmunization was also shown. Results are plotted as percent tumor free mice as a function of days after tumor challenge for mice immunized with PBS and challenged with $5 \times 10^4$ CT26 cells (circles); irradiated CT26 cells with empty vector/$5 \times 10^5$ CT26 cells (squares); irradiated CT26 cells with empty vector/$5 \times 10^6$ CT26 cells (upward triangles); irradiated CT26-hsp110 cells/5×10⁵ CT26 cells (downward triangles); and irradiated CT26-hsp110 cells/5×10⁶ CT26 cells (diamonds).

FIG. 29 is a plot showing the effect of injection with irradiated hsp110-overexpressing cells on the response to challenge with live CT26 cells. Mice were injected with $5 \times 10^5$ irradiated (9,000 rad) CT26-hsp110 cells subcutaneously in the left flank. Two weeks later, mice were challenged on the right flank with live CT26 cells. Growth of tumor in mice without preimmunization was also shown. Results are plotted as percent tumor free mice as a function of days after tumor challenge for mice immunized with PBS and challenged with $5 \times 10^4$ CT26 cells (circles); irradiated CT26 cells with empty vector/$5 \times 10^5$ CT26 cells (squares); irradiated CT26 cells with empty vector/$5 \times 10^6$ CT26 cells (upward triangles); irradiated CT26-hsp110 cells/$5 \times 10^5$ CT26 cells (downward triangles); and irradiated CT26-hsp110 cells/$5 \times 10^6$ CT26 cells (diamonds).

Figure 30:
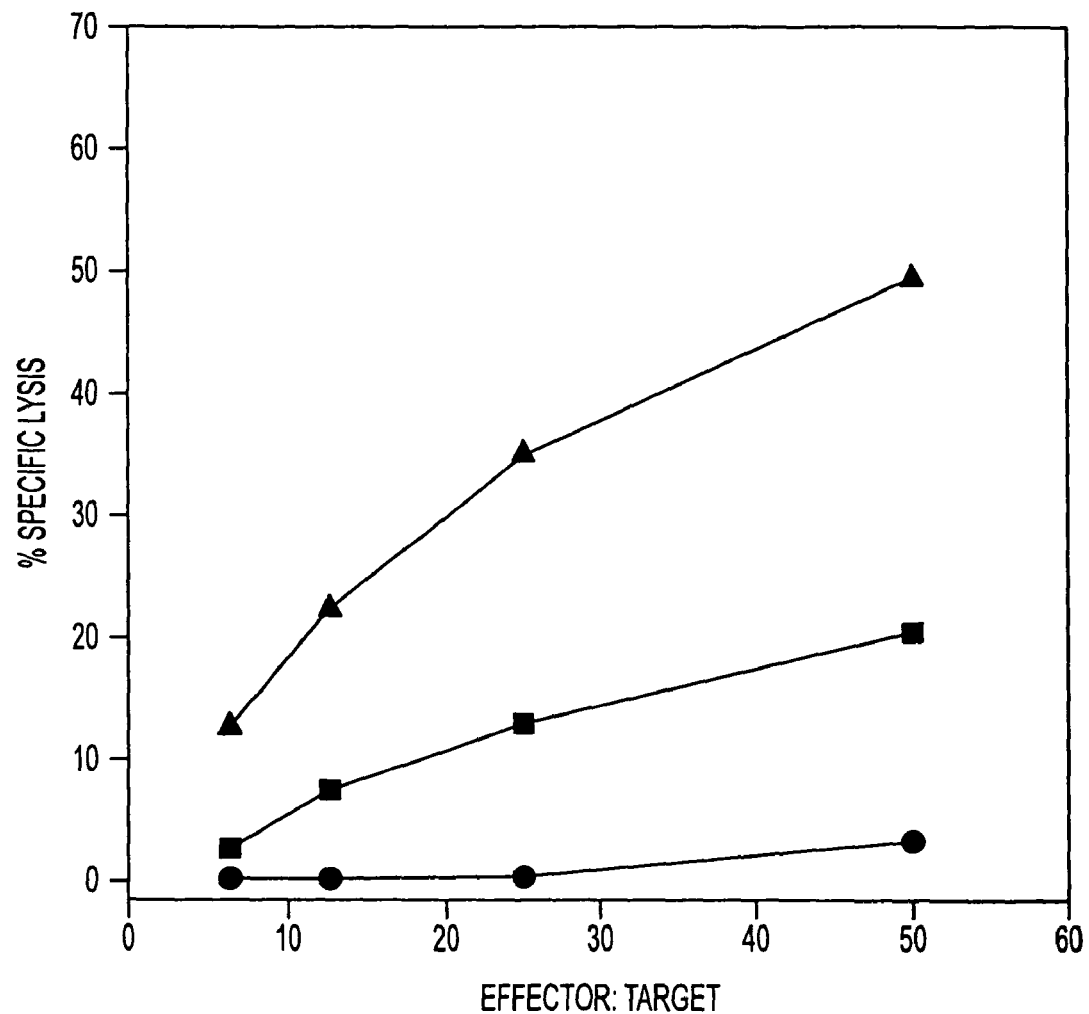
FIG. 30 is a graph showing tumor specific CTL response elicited by immunization with tumor derived hsp110. Mice were injected with 5×10⁵ irradiated (9,000 rad) CT26-empty vector and CT26-hsp 110 cells subcutaneously. Two weeks later, splenocytes were isolated as effector cells and re-stimulated with irradiated Colon 26 in vitro for 5 days. The lymphocytes were analyzed for cytotoxic activity using $^{51}$Cr-labeled Colon 26 as target cells. Meth A tumor cells were also used as target in the experiment, and no cell lysis was observed. Results are plotted as percent specific lysis as a function of effector:target ratio for control (circles), irradiated CT26 cells (squares), and irradiated CT26-hsp110 cells (triangles).

FIG. 30 is a graph showing tumor specific CTL response elicited by immunization with tumor derived hsp110. Mice were injected with 5×10⁵ irradiated (9,000 rad) CT26-empty vector and CT26-hsp 110 cells subcutaneously. Two weeks later, splenocytes were isolated as effector cells and re-stimulated with irradiated Colon 26 in vitro for 5 days. The lymphocytes were analyzed for cytotoxic activity using $^{51}$Cr-labeled Colon 26 as target cells. Meth A tumor cells were also used as target in the experiment, and no cell lysis was observed. Results are plotted as percent specific lysis as a function of effector:target ratio for control (circles), irradiated CT26 cells (squares), and irradiated CT26-hsp110 cells (triangles).

Figure 31:
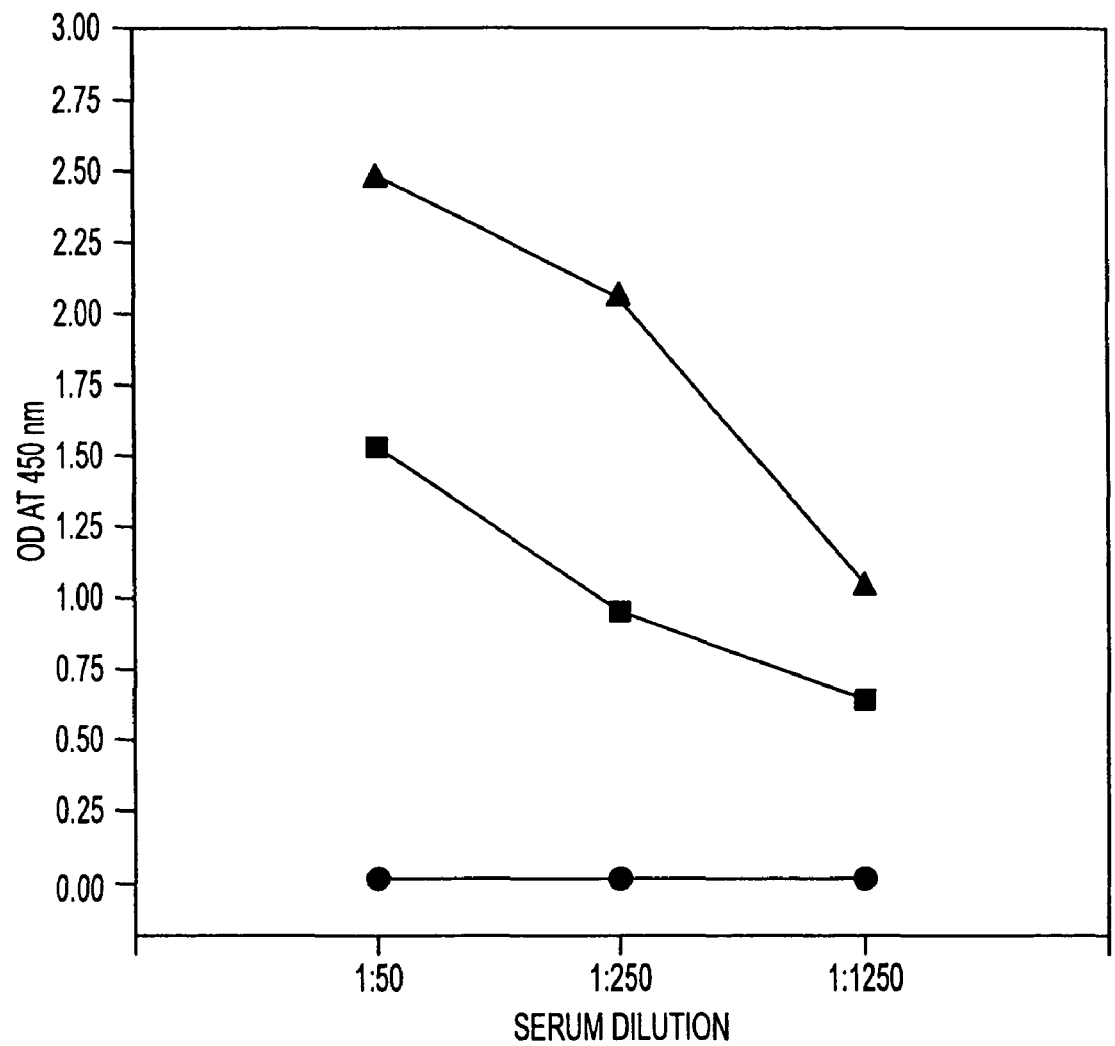
FIG. 31 is a graph showing antibody response against CT26 cells following immunization with irradiated hsp110-overexpressing cells. Mice were injected with 5×10⁵ irradiated (9,000 rad) CT26 empty vector and CT26-hsp110 cells subcutaneously. Two weeks later, serum was collected and assayed for antibody response using ELISA. Results are plotted as OD at 450 nm as a function of serum dilution for control (circles), CT26-empty vector (squares), and CT26-hsp110 (triangles).

FIG. 31 is a graph showing antibody response against CT26 cells following immunization with irradiated hsp110-overexpressing cells. Mice were injected with 5×10⁵ irradiated (9,000 rad) CT26 empty vector and CT26-hsp110 cells subcutaneously. Two weeks later, serum was collected and assayed for antibody response using ELISA. Results are plotted as OD at 450 nm as a function of serum dilution for control (circles), CT26-empty vector (squares), and CT26-hsp110 (triangles).

Example 14

GM-CSF-Secreting Cells Enhance Protective Effect of CT26-Hsp110 Cells

This example demonstrates that cells transfected with a GM-CSF gene, when co-injected with CT26-hsp110 cells, provide enhanced protection against tumor challenge that leaves all mice treated with the combined therapy free of tumors.

Figure 32:
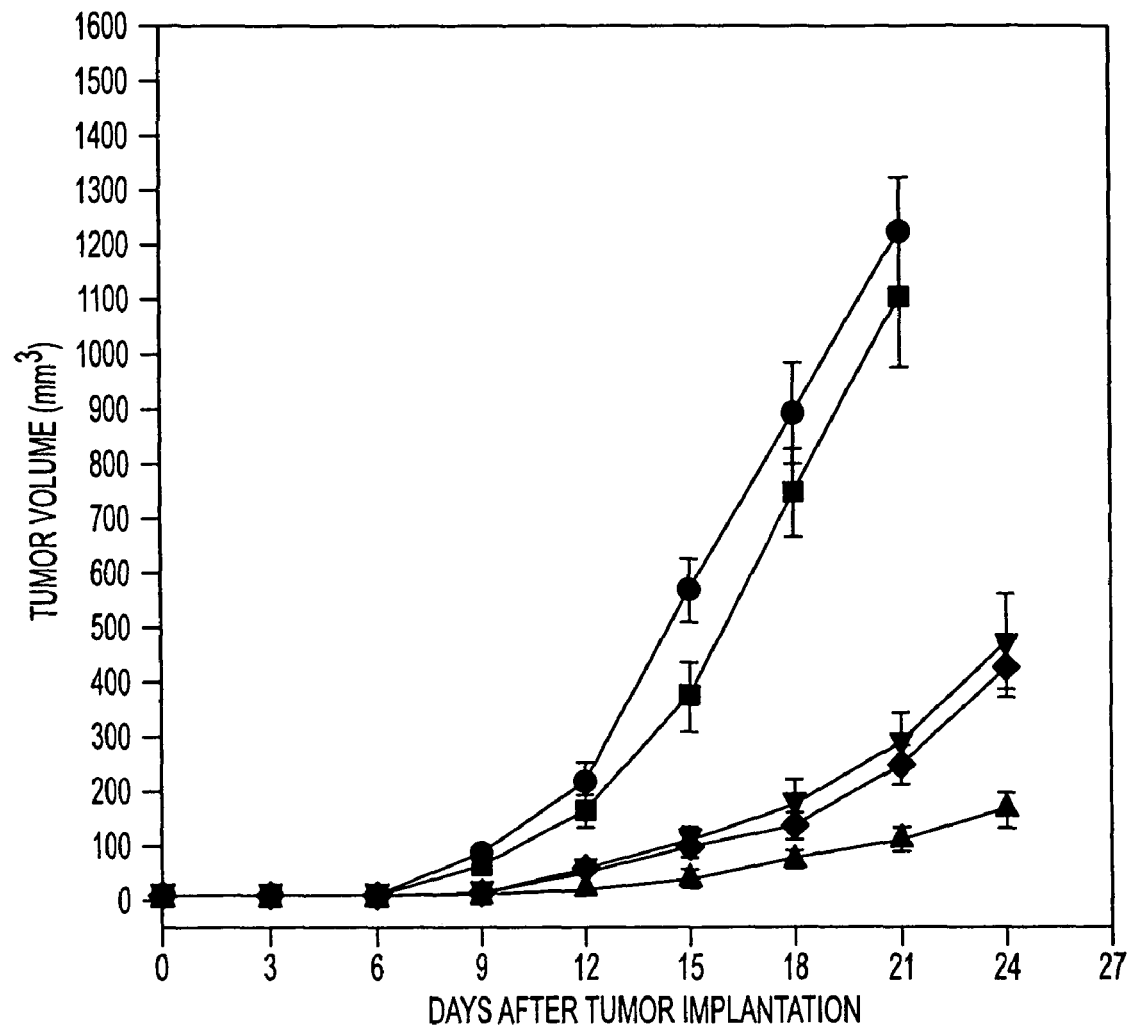
FIG. 32 is a graph showing the effect of GM-CSF from bystander cells on the growth of hsp110 overexpressing cells. Mice were injected subcutaneously with 5×10⁴ live tumor cells as follows: CT26-empty vector cells (circles), CT26-vector cells plus irradiated B78H1GM-CSF cells (2:1 ratio; squares), CT26-hsp110 cells plus irradiated B78H1GM CSF cells (2:1 ratio; upward triangles), CT26-hsp110 cells (downward triangles), CT26-hsp110 plus irradiated B78H1 cells (2:1 ratio; diamonds). The B78H1GM-CSF are B16 cells transfected with CM-CSF gene, while B78H1 are wild type cells. Tumor growth was recorded by measuring the size of tumor, and is plotted as tumor volume in cubic mm as a function of days after implantation.

FIG. 32 is a graph showing the effect of GM-CSF from bystander cells on the growth of hsp110 overexpressing cells. Mice were injected subcutaneously with 5×10⁴ live tumor cells as follows: CT26-empty vector cells (circles), CT26-vector cells plus irradiated B78H1GM-CSF cells (2:1 ratio; squares), CT26-hsp110 cells plus irradiated B78H1GM CSF cells (2:1 ratio; upward triangles), CT26-hsp110 cells (downward triangles), CT26-hsp110 plus irradiated B78H1 cells (2:1 ratio; diamonds). The B78H1GM-CSF are B16 cells transfected with CM-CSF gene, while B78H1 are wild type cells. Tumor growth was recorded by measuring the size of tumor, and is plotted as tumor volume in cubic mm as a function of days after implantation.

Figure 33:
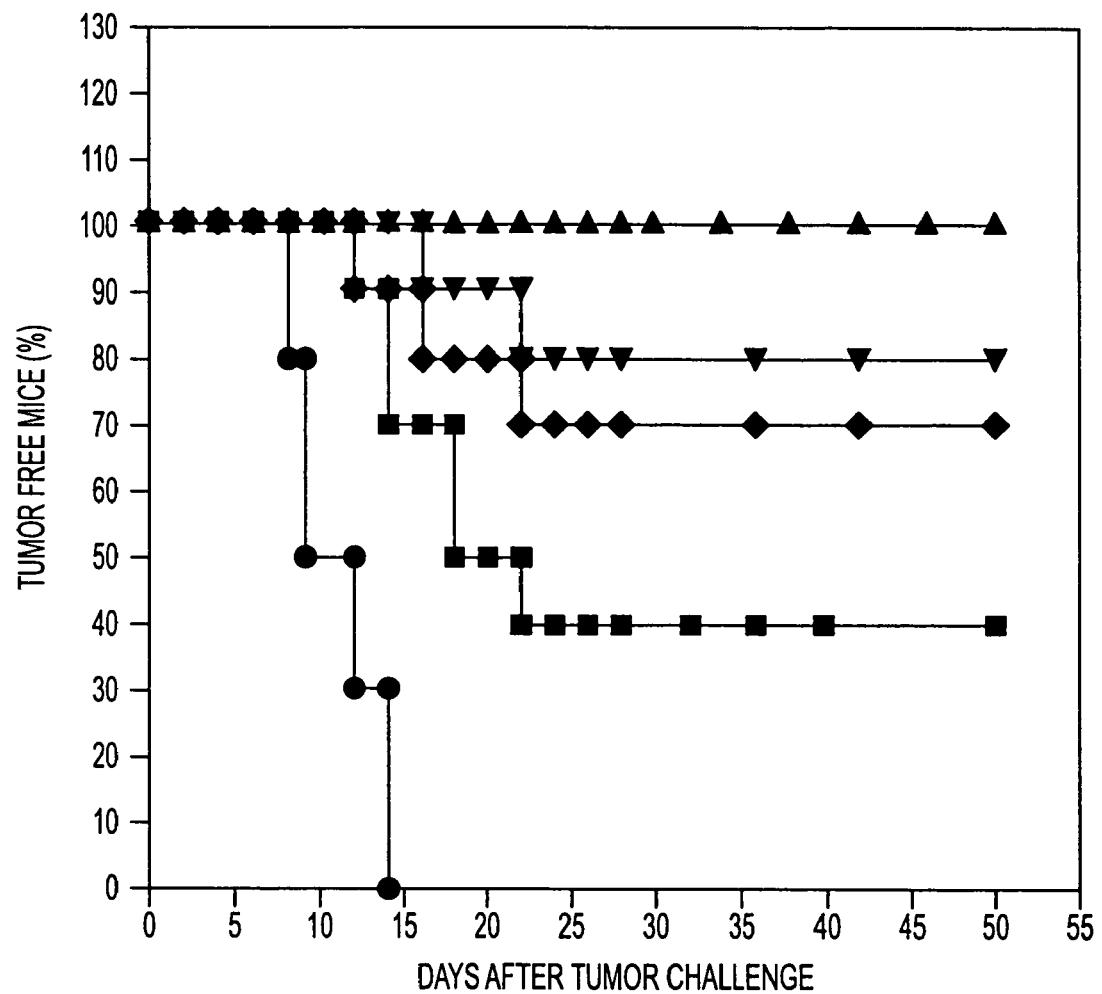
FIG. 33 is a graph showing the effect of co-injecting irradiated hsp110-overexpressing tumor vaccine and GM-CSF-secreting bystander cells on the response to wild-type CT26 tumor cell challenge. Mice were immunized subcutaneously with irradiated 5×10⁵ tumor cells as follows: CT26-empty vector cells, CT26-vector cells plus B78H1GM-CSF cells (2:1 ratio; squares), CT26-hsp110 cells plus B78H1GM-CSF cells (2:1; upward triangles), CT26-hsp110 cells (downward triangles), CT26-hsp110 plus B78H1 cells (2:1; diamonds). Also shown are results for mice immunized only with PBS (circles). Mice were challenged at a separate site with CT26 wild-type cells and monitored every other day for the tumor development. Results are plotted as percent tumor free mice at the indicated number of days after tumor challenge.

FIG. 33 is a graph showing the effect of co-injecting irradiated hsp110-overexpressing tumor vaccine and GM-CSF-secreting bystander cells on the response to wild-type CT26 tumor cell challenge. Mice were immunized subcutaneously with irradiated 5×10⁵ tumor cells as follows: CT26-empty vector cells, CT26-vector cells plus B78H1GM-CSF cells (2:1 ratio; squares), CT26-hsp110 cells plus B78H1GM-CSF cells (2:1; upward triangles), CT26-hsp110 cells (downward triangles), CT26-hsp110 plus B78H1 cells (2:1; diamonds). Also shown are results for mice immunized only with PBS (circles). Mice were challenged at a separate site with CT26 wild-type cells and monitored every other day for the tumor development. Results are plotted as percent tumor free mice at the indicated number of days after tumor challenge.

Example 15

Immunization With Tumor-Derived Stress Protein Complexes Stimulates Cellular Immunity and Inhibits Metastatic Tumor Growth This example demonstrates that tumor-derived stress protein complexes of the invention can be used to stimulate cellular immunity and inhibit metastatic tumor growth. Interferon-gamma secretion was stimulated by immunization with colon 26 tumor-derived hsp110 and grp170, as well as with B16F10-derived grp170. Immunization with B16F10-derived grp170 was also shown to elicit a tumor-specific CTL response and a reduction in lung metastases.

Figure 34:
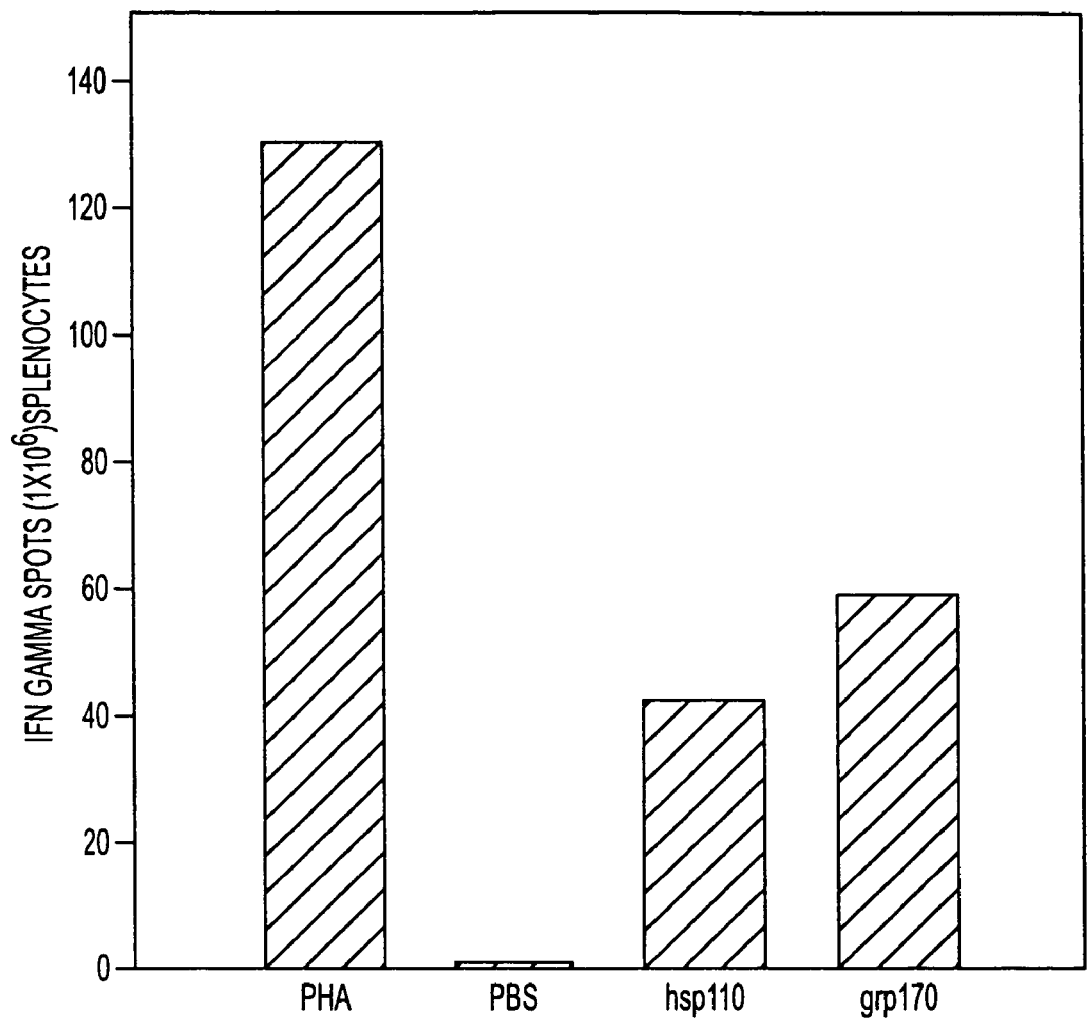
FIG. 34 is a bar graph showing that immunization with colon 26-derived hsp110 or grp170 stimulates interferon (IFN) gamma secretion. A week after mice were immunized with hsp110 or grp170, splenocytes were isolated for ELISPOT assay. Phytohemagglutinin (PHA) treated lymphocytes were used for positive control.

FIG. 34 is a bar graph showing that immunization with colon 26-derived hsp110 or grp170 stimulates interferon (IFN) gamma secretion. A week after mice were immunized with hsp110 or grp170, splenocytes were isolated for ELISPOT assay. Phytohemagglutinin (PHA) treated lymphocytes were used for positive control.

Figure 35:
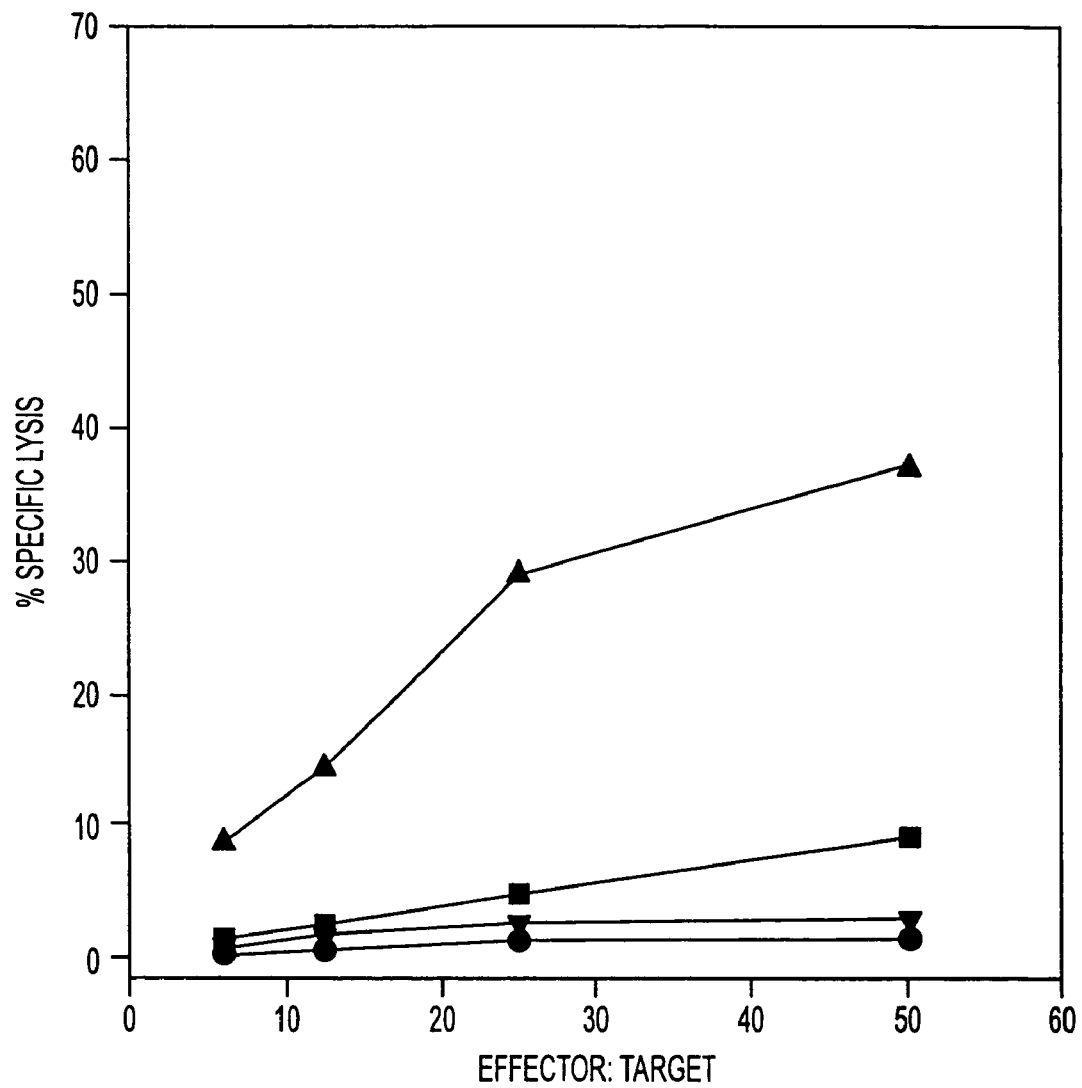
FIG. 35 is a graph showing tumor specific CTL response elicited by immunization with B16F10 tumor derived grp170. Mice were immunized twice with grp170 (40 μg) at weekly intervals. One week after the second immunization, splenocytes were isolated as effector cells and restimulated with irradiated B16F10 cells in vitro for 5 days. The lymphocytes were analyzed for cytotoxic activity using $^{51}$Cr-labeled B16F10 or Meth A cells as target cells. Results are plotted as percent specific lysis as a function of effector:target ratio for controls (circles), liver-derived grp170 (squares), B16F10-derived grp170 (upward triangles), and Meth A-derived grp170 (downward triangles).

FIG. 35 is a graph showing tumor specific CTL response elicited by immunization with B16F10 tumor-derived grp170. Mice were immunized twice with grp170 (40 µg) at weekly intervals. One week after the second immunization, splenocytes were isolated as effector cells and restimulated with irradiated B16F10 cells in vitro for 5 days. The lymphocytes were analyzed for cytotoxic activity using $^{51}$Cr-labeled B16F10 or Meth A cells as target cells. Results are plotted as percent specific lysis as a function of effector:target ratio for controls (circles), liver-derived grp170 (squares), B16F10-derived grp170 (upward triangles), and Meth A-derived grp170 (downward triangles).

Figure 36:
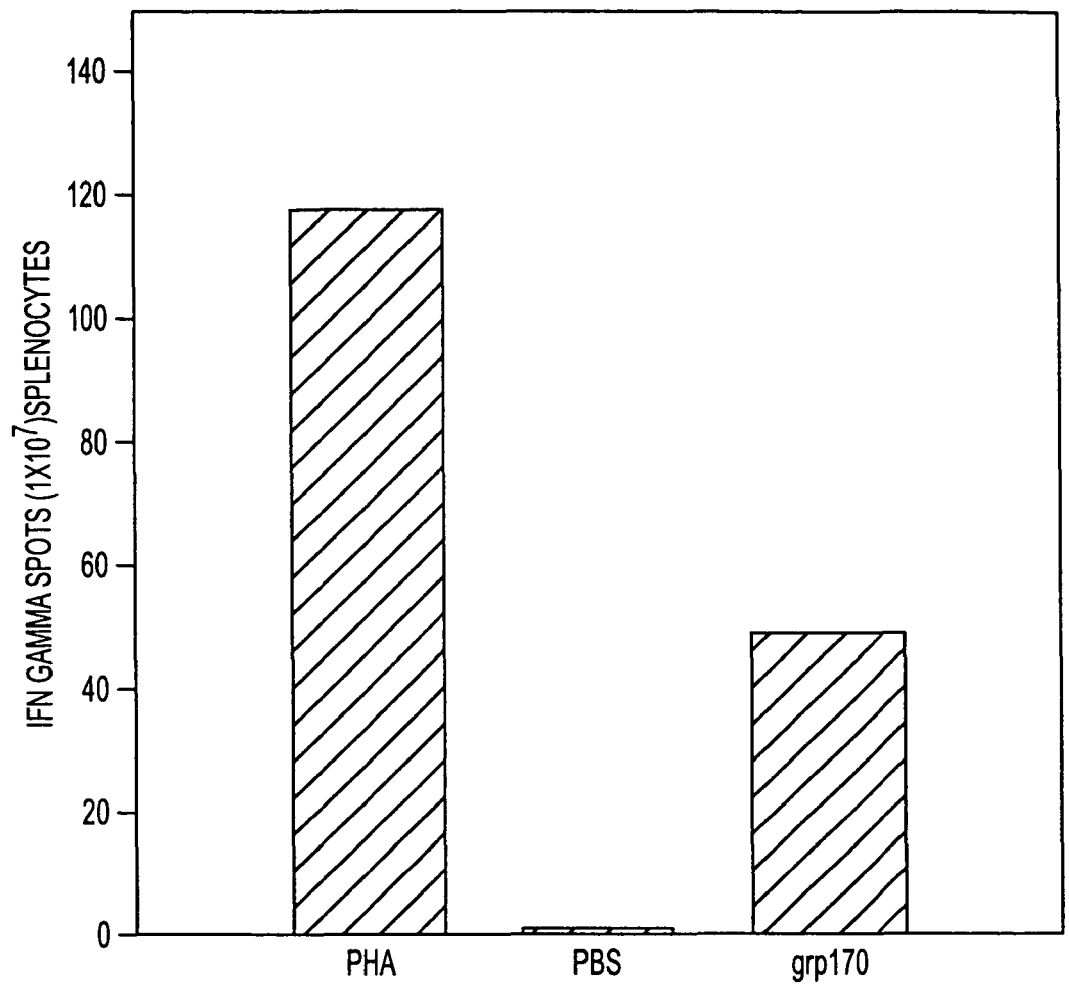
FIG. 36 shows immunization with B16F10-derived grp170 stimulates IFN gamma secretion. A week after mice were immunized with hsp110 or grp170, splenocytes were isolated for ELISPOT assay.

FIG. 36 shows immunization with B16F10-derived grp170 stimulates IFN gamma secretion. A week after mice were immunized with hsp110 or grp170, splenocytes were isolated for ELISPOT assay.

Figure 37:
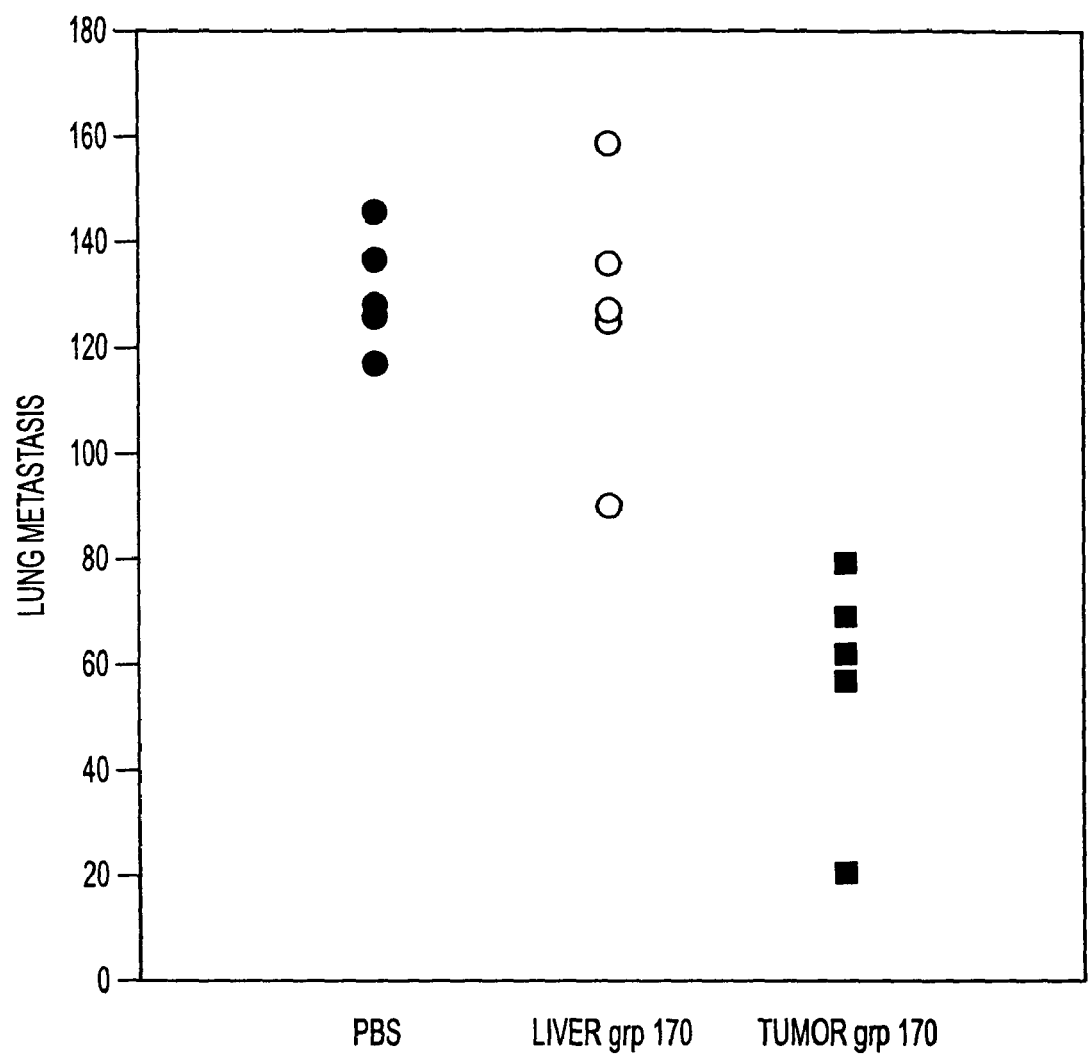
FIG. 37 shows lung metastases for mice in which 1×10⁵ B16F10 cells were inoculated intravenously into the tail vein of each C57BL/6 mouse. 24 hr after tumor cell injection, mice were then treated with PBS (closed circles), liver-derived grp170 (open circles), or tumor-derived grp170 (40 μg). Three treatments were carried out during the whole protocol. The animals were killed 3 weeks after tumor injection, lungs were removed and surface colonies were counted.

FIG. 37 shows lung metastases for mice in which 1×10⁵ B16F10 cells were inoculated intravenously into the tail vein of each C57BL/6 mouse. 24 hr after tumor cell injection, mice were then treated with PBS (closed circles), liver-derived grp170 (open circles), or tumor-derived grp170 (40 µg). Three treatments were carried out during the whole protocol. The animals were killed 3 weeks after tumor injection, lungs were removed and surface colonies were counted.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A pharmaceutical composition comprising an isolated stress protein complex and a physiologically acceptable carrier, wherein the stress protein complex comprises a grp170 polypeptide and an immunogenic polypeptide, wherein the grp170 polypeptide is complexed with the immunogenic polypeptide by non-covalent interaction, and wherein the complex has been heated in vitro to approximately 39° C. to approximately 43° C. so as to enhance binding of the grp170 polypeptide to the immunogenic polypeptide.

2. The pharmaceutical composition of claim 1, wherein the complex is derived from a tumor.

3. The pharmaceutical composition of claim 1, wherein the complex is derived from a cell infected with an infectious agent.

4. The pharmaceutical composition of claim 1, wherein the immunogenic polypeptide comprises a cancer antigen.

5. The pharmaceutical composition of claim 4, wherein the cancer antigen comprises a colon cancer, melanoma or fibrosarcoma antigen.

6. The pharmaceutical composition of claim 1, wherein the immunogenic polypeptide comprises an infectious disease antigen.

7. The pharmaceutical composition of claim 1, wherein the complex has been heated to a temperature of about 39-40° C.

8. The pharmaceutical composition of claim 1, wherein the complex has been heated to a temperature of about 43° C.

9. The pharmaceutical composition of claim 1, wherein the immunogenic polypeptide is produced by recombinant techniques.

10. A pharmaceutical composition comprising an isolated stress protein complex and a physiologically acceptable carrier, wherein the stress protein complex comprises a grp170 polypeptide and an immunogenic polypeptide, wherein the grp170 polypeptide is complexed with the immunogenic polypeptide by non-covalent interaction, wherein the complex has been heated in vitro to approximately 39° C. to approximately 43° C. so as to enhance binding of the grp170 polypeptide to the immunogenic polypeptide, and wherein the stress protein complex further comprises a polypeptide selected from the group consisting of hsp110, hsp70, hsp90, grp78 and grp94.

11. A method of enhancing the immunogenicity of an isolated stress protein complex comprising heating the stress protein complex in vitro to approximately 39° C. to approximately 43° C., wherein the stress protein complex comprises a grp170 stress polypeptide and an immunogenic polypeptide.

12. The method of claim 11, wherein the heating comprises heating the stress protein complex to a temperature of 39-40° C.

13. The method of claim 11, wherein the heating comprises heating the stress protein complex to a temperature of 39° C.

14. The method of claim 11, wherein the immunogenic polypeptide is a cancer antigen or an infectious disease antigen.

15. A method of enhancing the immunogenicity of an isolated stress protein complex comprising heating the stress protein complex in vitro to approximately 43° C. wherein the stress protein complex comprises a grp170 polypeptide and an immunogenic polypeptide, and wherein the immunogenic polypeptide is a cancer antigen or an infectious disease antigen.

16. The method of claim 15, wherein the immunogenic polypeptide is an infectious disease antigen.

17. A method of enhancing an immune response to an antigen administered to a subject comprising administering a grp170 polypeptide and the antigen to the subject, wherein the grp170 polypeptide is complexed with the antigen by non-covalent interaction, and wherein the complex has been heated in vitro to approximately 39° C. to approximately 43° C. so as to enhance binding of the grp170 polypeptide to the immunogenic polypeptide.

18. A method for inhibiting tumor growth in a subject, comprising administering to a patient an effective amount of a pharmaceutical composition of claim 4 to elicit an anti-tumor response, and thereby inhibiting tumor growth in the subject.

* * * * *

UNITED STATES PATENT AND TRADEMARK OFFICE
CERTIFICATE OF CORRECTION

PATENT NO.       : 7,976,846 B2
APPLICATION NO.  : 11/103222
DATED            : July 12, 2011
INVENTOR(S)      : Subjeck et al.

Page 1 of 1

It is certified that error appears in the above-identified patent and that said Letters Patent is hereby corrected as shown below:

Title Page 2, Item (56), second column, under the heading *Other Publications*, delete "Doug et al." and insert --Dong et al.--

In Claim 1, Column 47, line 62, after approximately, delete "39° C." and insert --39 °C--
In Claim 1, Column 47, line 63, after approximately, delete "43° C." and insert --43 °C--
In Claim 10, Column 49, line 15, after approximately, delete "39°C." and insert --39 °C--
In Claim 10, Column 49, line 16, after approximately, delete "43°C." and insert --43 °C--
In Claim 11, Column 49, line 23, after approximately, delete "39°C." and insert --39 °C--
In Claim 11, Column 49, line 24, after approximately, delete "43°C." and insert --43 °C--
In Claim 15, Column 50, line 8, after approximately, delete "43°C." and insert --39 °C to approximately 43 °C--

In Claim 17, Column 50, lines 21-22, after approximately, delete "39° C. to approxtimately 43° C." and insert --39 °C to approximately 43 °C--

Signed and Sealed this
Eighteenth Day of October, 2011

David J. Kappos
*Director of the United States Patent and Trademark Office*

SEQUENCE LISTING

<160> NUMBER OF SEQ ID NOS: 6

<210> SEQ ID NO 1
<211> LENGTH: 33
<212> TYPE: DNA
<213> ORGANISM: Artificial Sequence
<220> FEATURE:
<223> OTHER INFORMATION: Primer -continued

```
<400> SEQUENCE: 1
gctagaggat cctgtgcatt gcagtgtgca att                           33

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
cagcgcaagc ttactagtcc aggtccatat tga                           33

<210> SEQ ID NO 3
<211> LENGTH: 32
<212> TYPE: DNA
<213> ORGANISM: Artificial Sequence
<220> FEATURE:
<223> OTHER INFORMATION: Primer

<400> SEQUENCE: 3
gacgacggat cctctgtcga ggcagacatg ga                            32

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
cagcgcaagc ttactagtcc aggtccatat tga                           33

<210> SEQ ID NO 5
<211> LENGTH: 10
<212> TYPE: PRT
<213> ORGANISM: Homo Sapiens

<400> SEQUENCE: 5

Val Leu Gln Gly Leu Pro Arg Glu Tyr Val
 1               5                  10

<210> SEQ ID NO 6
<211> LENGTH: 9
<212> TYPE: PRT
<213> ORGANISM: Homo Sapiens

<400> SEQUENCE: 6

Lys Ile Phe Gly Ser Leu Ala Phe Leu
 1               5
```